US009918825B2

(12) United States Patent
Shalev et al.

(10) Patent No.: US 9,918,825 B2
(45) Date of Patent: Mar. 20, 2018

(54) VASCULAR PROSTHESIS FOR TREATING ANEURYSMS

(71) Applicant: ENDOSPAN LTD., Herzilyia Pituach (IL)

(72) Inventors: Alon Shalev, Ra'anana (IL); Raphael Benary, Tel Aviv (IL)

(73) Assignee: ENDOSPAN LTD., Herzilyia Pituach (IL)

( * ) Notice: Subject to any disclaimer, the term of this patent is extended or adjusted under 35 U.S.C. 154(b) by 275 days.

(21) Appl. No.: 14/518,542

(22) Filed: Oct. 20, 2014

(65) Prior Publication Data

US 2015/0039074 A1 Feb. 5, 2015

Related U.S. Application Data

(63) Continuation of application No. 13/380,278, filed as application No. PCT/IB2010/052861 on Jun. 23, 2010, now Pat. No. 8,870,938.

(Continued)

(51) Int. Cl.
*A61F 2/07* (2013.01)
*A61F 2/954* (2013.01)
(Continued)

(52) U.S. Cl.
CPC ............... *A61F 2/07* (2013.01); *A61F 2/856* (2013.01); *A61F 2/954* (2013.01); *A61F 2/958* (2013.01);
(Continued)

(58) Field of Classification Search
CPC .................... A61F 2/07; A61F 2/954; A61F 2002/072–2002/077; A61F 2002/823
See application file for complete search history.

(56) References Cited

U.S. PATENT DOCUMENTS

| | | |
|---|---|---|
| 4,180,613 A | 12/1979 | Vassiliou |
| 4,355,426 A | 10/1982 | MacGregor |

(Continued)

FOREIGN PATENT DOCUMENTS

| | | |
|---|---|---|
| CA | 2497704 | 3/2004 |
| CN | 2453960 | 10/2001 |

(Continued)

OTHER PUBLICATIONS

"Aortic Aneurysm" O'Gara, Patrick T. Circulation. 2003; 107: e43-e45.*

(Continued)

*Primary Examiner* — Shaun L David
(74) *Attorney, Agent, or Firm* — Sughrue Mion, PLLC

(57) ABSTRACT

An endovascular stent-graft is provided that includes a structural member, which includes structural stent elements, at least a portion of which define a stent body when the stent-graft assumes a radially-expanded state; and a fluid flow guide. When the stent-graft assumes the radially-expanded state, (a) a first subset of the structural stent elements are configured to cause the stent body and the fluid flow guide to define a bulge that extends radially outward and has a greatest cross-sectional area that is equal to at least 120% of a cross-sectional area of a narrowest portion of the stent-graft rostral to the bulge, and (b) a second subset of the structural stent elements are not configured to cause the fluid flow guide to define the bulge. The structural stent elements of the first subset at least partially overlap the structural stent elements of the second subset lengthwise along the stent body.

37 Claims, 41 Drawing Sheets

Related U.S. Application Data

(60) Provisional application No. 61/219,758, filed on Jun. 23, 2009, provisional application No. 61/221,074, filed on Jun. 28, 2009.

(51) Int. Cl.
  *A61F 2/958*  (2013.01)
  *A61F 2/856*  (2013.01)
  *A61F 2/06*   (2013.01)
  *A61F 2/848*  (2013.01)
  *A61F 2/89*   (2013.01)

(52) U.S. Cl.
  CPC .............. *A61F 2/06* (2013.01); *A61F 2/848* (2013.01); *A61F 2/89* (2013.01); *A61F 2002/061* (2013.01); *A61F 2002/065* (2013.01); *A61F 2002/068* (2013.01); *A61F 2002/075* (2013.01); *A61F 2002/8483* (2013.01); *A61F 2220/0016* (2013.01); *A61F 2220/0075* (2013.01); *A61F 2230/001* (2013.01); *A61F 2230/005* (2013.01); *A61F 2230/0054* (2013.01); *A61F 2230/0067* (2013.01); *A61F 2230/0093* (2013.01)

(56) References Cited

U.S. PATENT DOCUMENTS

| | | |
|---|---|---|
| 4,505,767 A | 3/1985 | Quin |
| 4,562,596 A | 1/1986 | Kornberg |
| 4,577,631 A | 3/1986 | Kreamer |
| 4,617,932 A | 10/1986 | Kornberg |
| 4,665,906 A | 5/1987 | Jervis |
| 4,739,762 A | 4/1988 | Palmaz |
| 4,787,899 A | 11/1988 | Lazarus |
| 4,878,906 A | 11/1989 | Lindemann et al. |
| 4,886,062 A | 12/1989 | Wiktor |
| 4,938,740 A | 7/1990 | Melbin |
| 4,969,458 A | 11/1990 | Wiktor |
| 5,042,707 A | 8/1991 | Taheri |
| 5,064,435 A | 11/1991 | Porter |
| 5,104,404 A | 4/1992 | Wolff |
| 5,122,136 A | 6/1992 | Guglielmi et al. |
| 5,129,910 A | 7/1992 | Phan et al. |
| 5,133,732 A | 7/1992 | Wiktor |
| 5,192,256 A | 3/1993 | Ryan |
| 5,192,286 A | 3/1993 | Phan et al. |
| 5,234,448 A | 8/1993 | Wholey et al. |
| 5,383,926 A | 1/1995 | Lock et al. |
| 5,425,739 A | 6/1995 | Jessen |
| 5,456,694 A | 10/1995 | Marin et al. |
| 5,486,183 A | 1/1996 | Middleman et al. |
| 5,507,769 A | 4/1996 | Marin et al. |
| 5,509,923 A | 4/1996 | Middleman et al. |
| 5,522,880 A | 6/1996 | Barone et al. |
| 5,527,322 A | 6/1996 | Klein et al. |
| 5,549,662 A | 8/1996 | Fordenbacher |
| 5,554,181 A | 9/1996 | Das |
| 5,556,413 A | 9/1996 | Lam |
| 5,562,724 A | 10/1996 | Vorwerk et al. |
| 5,575,818 A | 11/1996 | Pinchuk |
| 5,607,445 A | 3/1997 | Summers |
| 5,613,974 A | 3/1997 | Andreas et al. |
| 5,632,746 A | 5/1997 | Middleman et al. |
| 5,632,763 A | 5/1997 | Glastra |
| 5,632,772 A | 5/1997 | Alcime et al. |
| 5,639,278 A | 6/1997 | Dereume et al. |
| 5,643,340 A | 7/1997 | Nunokawa |
| 5,653,743 A | 8/1997 | Martin |
| 5,676,696 A | 10/1997 | Marcade |
| 5,676,697 A | 10/1997 | McDonald |
| 5,693,084 A | 12/1997 | Chuter |
| 5,728,134 A | 3/1998 | Barak |
| 5,749,879 A | 5/1998 | Middleman et al. |
| 5,755,770 A | 5/1998 | Ravenscroft |
| 5,755,771 A | 5/1998 | Penn et al. |
| 5,755,777 A | 5/1998 | Chuter |
| 5,755,781 A | 5/1998 | Jayaraman |
| 5,769,882 A | 6/1998 | Fogarty et al. |
| 5,769,884 A | 6/1998 | Solovay |
| 5,782,903 A | 7/1998 | Wiktor |
| 5,782,906 A | 7/1998 | Marshall et al. |
| 5,824,040 A | 10/1998 | Cox et al. |
| 5,824,055 A | 10/1998 | Spiridigliozzi et al. |
| 5,827,321 A | 10/1998 | Roubin et al. |
| 5,843,170 A | 12/1998 | Ahn |
| 5,855,600 A | 1/1999 | Alt |
| 5,860,991 A | 1/1999 | Klein et al. |
| 5,876,432 A | 3/1999 | Lau et al. |
| 5,906,641 A | 5/1999 | Thompson et al. |
| 5,921,994 A | 7/1999 | Andreas et al. |
| 5,925,076 A | 7/1999 | Inoue |
| 5,944,750 A | 8/1999 | Tanner et al. |
| 5,948,018 A | 9/1999 | Dereume et al. |
| 5,968,091 A | 10/1999 | Pinchuk et al. |
| 5,980,552 A | 11/1999 | Pinchasik et al. |
| 5,984,955 A | 11/1999 | Wisselink |
| 6,015,431 A | 1/2000 | Thornton et al. |
| 6,016,810 A | 1/2000 | Ravenscroft |
| 6,030,414 A | 2/2000 | Taheri |
| 6,033,435 A | 3/2000 | Penn et al. |
| 6,036,723 A | 3/2000 | Anidjar et al. |
| 6,036,725 A | 3/2000 | Avellanet |
| 6,049,824 A | 4/2000 | Simonin |
| 6,051,021 A | 4/2000 | Frid |
| 6,059,824 A | 5/2000 | Taheri |
| 6,099,497 A | 8/2000 | Adams et al. |
| 6,099,548 A | 8/2000 | Taheri |
| 6,117,145 A | 9/2000 | Wood et al. |
| 6,129,738 A | 10/2000 | Lashinski et al. |
| 6,132,457 A | 10/2000 | Chobotov |
| 6,156,064 A | 12/2000 | Chouinard |
| 6,159,228 A | 12/2000 | Frid et al. |
| 6,176,875 B1 | 1/2001 | Lenker et al. |
| 6,179,878 B1 | 1/2001 | Duerig et al. |
| 6,200,339 B1 | 3/2001 | Leschinsky et al. |
| 6,206,893 B1 | 3/2001 | Klein et al. |
| 6,270,524 B1 | 8/2001 | Kim |
| 6,283,991 B1 | 9/2001 | Cox et al. |
| 6,287,335 B1 | 9/2001 | Drasler et al. |
| 6,290,720 B1 | 9/2001 | Khosravi et al. |
| 6,296,661 B1 | 10/2001 | Davila et al. |
| 6,312,458 B1 | 11/2001 | Golds |
| 6,325,819 B1 | 12/2001 | Pavcnik et al. |
| 6,325,823 B1 | 12/2001 | Horzewski et al. |
| 6,344,056 B1 | 2/2002 | Dehdashtian |
| 6,395,018 B1 | 5/2002 | Castaneda |
| 6,406,420 B1 | 6/2002 | McCarthy et al. |
| 6,428,565 B1 | 8/2002 | Wisselink |
| 6,451,051 B2 | 9/2002 | Drasler et al. |
| 6,471,722 B1 | 10/2002 | Inoue |
| 6,506,211 B1 | 1/2003 | Skubitz et al. |
| 6,520,988 B1 | 2/2003 | Colombo et al. |
| 6,544,279 B1 | 4/2003 | Hopkins et al. |
| 6,576,009 B2 | 6/2003 | Ryan et al. |
| 6,613,078 B1 | 9/2003 | Barone |
| 6,635,083 B1 | 10/2003 | Cheng et al. |
| 6,645,242 B1 | 11/2003 | Quinn |
| 6,648,911 B1 | 11/2003 | Sirhan et al. |
| 6,652,567 B1 | 11/2003 | Deaton |
| 6,652,571 B1 | 11/2003 | White et al. |
| 6,656,214 B1 | 12/2003 | Fogarty et al. |
| 6,673,080 B2 | 1/2004 | Reynolds et al. |
| 6,692,520 B1 | 2/2004 | Gambale et al. |
| 6,695,833 B1 | 2/2004 | Frantzen |
| 6,695,875 B2 | 2/2004 | Stelter et al. |
| 6,699,277 B1 | 3/2004 | Freidberg et al. |
| 6,716,238 B2 | 4/2004 | Elliott |
| 6,729,356 B1 | 5/2004 | Baker et al. |
| 6,733,523 B2 | 5/2004 | Shaolian et al. |
| 6,743,195 B2 | 6/2004 | Zucker |
| 6,752,826 B2 | 6/2004 | Holloway et al. |
| 6,776,794 B1 | 8/2004 | Hong et al. |
| 6,808,534 B1 | 10/2004 | Escano |

(56) References Cited

U.S. PATENT DOCUMENTS

| | | |
|---|---|---|
| 6,814,749 B2 | 11/2004 | Cox et al. |
| 6,814,752 B1 | 11/2004 | Chuter |
| 6,824,560 B2 | 11/2004 | Pelton |
| 6,843,803 B2 | 1/2005 | Ryan et al. |
| 6,846,321 B2 | 1/2005 | Zucker |
| 6,860,900 B2 | 3/2005 | Clerc et al. |
| 6,907,285 B2 | 6/2005 | Denker et al. |
| 6,908,477 B2 | 6/2005 | McGuckin, Jr. et al. |
| 6,929,660 B1 | 8/2005 | Ainsworth et al. |
| 6,942,691 B1 | 9/2005 | Chuter |
| 6,964,679 B1 | 11/2005 | Marcade et al. |
| 6,986,774 B2 | 1/2006 | Middleman et al. |
| 7,008,441 B2 | 3/2006 | Zucker |
| 7,018,400 B2 | 3/2006 | Lashinski et al. |
| 7,022,131 B1 | 4/2006 | Derowe et al. |
| 7,044,962 B2 | 5/2006 | Elliott |
| 7,105,015 B2 | 9/2006 | Goshgarian |
| 7,105,020 B2 | 9/2006 | Greenberg et al. |
| 7,112,217 B1 | 9/2006 | Kugler et al. |
| 7,115,127 B2 | 10/2006 | Lindenbaum et al. |
| 7,122,052 B2 | 10/2006 | Greenhalgh |
| 7,131,991 B2 | 11/2006 | Zarins et al. |
| 7,144,421 B2 | 12/2006 | Carpenter et al. |
| 7,160,318 B2 | 1/2007 | Greenberg et al. |
| 7,175,651 B2 | 2/2007 | Kerr |
| 7,198,638 B2 | 4/2007 | Dong |
| 7,201,772 B2 | 4/2007 | Schwammenthal et al. |
| 7,220,274 B1 | 5/2007 | Quinn |
| 7,223,266 B2 | 5/2007 | Lindenbaum et al. |
| 7,270,675 B2 | 9/2007 | Chun et al. |
| 7,279,003 B2 | 10/2007 | Berra et al. |
| 7,294,145 B2 | 11/2007 | Ward |
| 7,294,147 B2 | 11/2007 | Hartley |
| 7,306,623 B2 | 12/2007 | Watson |
| 7,341,598 B2 | 3/2008 | Davidson et al. |
| 7,393,357 B2 | 7/2008 | Stelter et al. |
| 7,396,363 B2 | 7/2008 | Frid |
| 7,407,509 B2 | 8/2008 | Greenberg et al. |
| 7,413,573 B2 | 8/2008 | Hartley et al. |
| 7,425,219 B2 | 9/2008 | Quadri |
| 7,429,269 B2 | 9/2008 | Schwammenthal et al. |
| 7,438,721 B2 | 10/2008 | Doig et al. |
| 7,442,204 B2 | 10/2008 | Schwammenthal et al. |
| 7,473,272 B2 | 1/2009 | Pryor |
| 7,491,231 B2 | 2/2009 | Nazzaro et al. |
| 7,537,606 B2 | 5/2009 | Hartley et al. |
| 7,537,609 B2 | 5/2009 | Davidson et al. |
| 7,540,881 B2 | 6/2009 | Meyer et al. |
| 7,544,160 B2 | 6/2009 | Gross |
| 7,575,590 B2 | 8/2009 | Watson |
| 7,637,939 B2 | 12/2009 | Tischler |
| 7,645,298 B2 | 1/2010 | Hartley et al. |
| 7,655,036 B2 | 2/2010 | Goodson |
| 7,662,161 B2 | 2/2010 | Briganti et al. |
| 7,662,168 B2 | 2/2010 | McGuckin, Jr. et al. |
| 7,670,369 B2 | 3/2010 | Schaeffer |
| 7,678,141 B2 | 3/2010 | Greenan et al. |
| 7,699,885 B2 | 4/2010 | Leonhardt et al. |
| 7,708,704 B2 | 5/2010 | Mitelberg et al. |
| 7,722,626 B2 | 5/2010 | Middleman et al. |
| 7,731,732 B2 | 6/2010 | Ken |
| 7,766,955 B2 | 8/2010 | Vardi et al. |
| 7,771,465 B2 | 8/2010 | Zukowski |
| 7,789,903 B2 | 9/2010 | Spiridigliozzi et al. |
| 7,803,178 B2 | 9/2010 | Whirley et al. |
| 7,806,923 B2 | 10/2010 | Moloney |
| 7,815,673 B2 | 10/2010 | Bloom et al. |
| 7,833,259 B2 | 11/2010 | Boatman |
| 7,846,194 B2 | 12/2010 | Hartley et al. |
| 7,850,725 B2 | 12/2010 | Vardi et al. |
| 7,867,270 B2 | 1/2011 | Hartley et al. |
| 7,887,575 B2 | 2/2011 | Kujawski |
| 7,914,572 B2 | 3/2011 | Hartley et al. |
| 7,955,373 B2 | 6/2011 | Sowinski et al. |
| 7,955,374 B2 | 6/2011 | Erickson et al. |
| 7,959,662 B2 | 6/2011 | Erbel et al. |
| 7,959,669 B2 | 6/2011 | Chalekian et al. |
| 7,998,186 B2 | 8/2011 | Hartley |
| 7,998,187 B2 | 8/2011 | Hartley et al. |
| 8,012,193 B2 | 9/2011 | Hartley et al. |
| 8,021,412 B2 | 9/2011 | Hartley et al. |
| 8,021,418 B2 | 9/2011 | Gerberding et al. |
| 8,021,419 B2 | 9/2011 | Hartley et al. |
| 8,043,365 B2 | 10/2011 | Thramann |
| 8,048,139 B2 | 11/2011 | Frid et al. |
| 8,048,140 B2 | 11/2011 | Purdy |
| 8,048,147 B2 | 11/2011 | Adams |
| 8,052,736 B2 | 11/2011 | Doig et al. |
| 8,052,741 B2 | 11/2011 | Bruszewski et al. |
| 8,066,755 B2 | 11/2011 | Zacharias et al. |
| 8,080,053 B2 | 12/2011 | Satasiya et al. |
| 8,100,960 B2 | 1/2012 | Bruszewski |
| 8,118,854 B2 | 2/2012 | Bowe |
| 8,133,267 B2 | 3/2012 | Leonhardt et al. |
| 8,157,810 B2 | 4/2012 | Case et al. |
| 8,157,852 B2 | 4/2012 | Bloom et al. |
| 8,167,926 B2 | 5/2012 | Hartley et al. |
| 8,172,892 B2 | 5/2012 | Chuter et al. |
| 8,172,895 B2 | 5/2012 | Anderson et al. |
| 8,197,475 B2 | 6/2012 | Bruszewski et al. |
| 8,197,533 B2 | 6/2012 | Kujawski |
| 8,211,158 B2 | 7/2012 | Wolf |
| 8,216,298 B2 | 7/2012 | Wright et al. |
| 8,221,494 B2 | 7/2012 | Schreck et al. |
| 8,226,706 B2 | 7/2012 | Hartley et al. |
| 8,236,040 B2 | 8/2012 | Mayberry et al. |
| 8,251,963 B2 | 8/2012 | Chin et al. |
| 8,257,423 B2 | 9/2012 | Kerr |
| 8,262,719 B2 | 9/2012 | Erickson et al. |
| 8,273,115 B2 | 9/2012 | Hamer et al. |
| 8,287,586 B2 | 10/2012 | Schaeffer et al. |
| 8,292,885 B2 | 10/2012 | Bruszewski et al. |
| 8,292,941 B2 | 10/2012 | Muzslay |
| 8,292,949 B2 | 10/2012 | Berra et al. |
| 8,292,951 B2 | 10/2012 | Muzslay |
| 8,333,800 B2 | 12/2012 | Bruszewski et al. |
| 8,337,546 B2 | 12/2012 | Bruszewski |
| 8,353,898 B2 | 1/2013 | Lutze et al. |
| 8,357,192 B2 | 1/2013 | Mayberry et al. |
| 8,361,134 B2 | 1/2013 | Hartley et al. |
| 8,394,136 B2 | 3/2013 | Hartley et al. |
| 8,425,585 B2 | 4/2013 | Melsheimer et al. |
| 8,470,018 B2 | 6/2013 | Hartley et al. |
| 8,475,513 B2 | 7/2013 | Sithian |
| 8,480,726 B2 | 7/2013 | Cunningham et al. |
| 8,486,131 B2 | 7/2013 | Shalev |
| 8,491,646 B2 | 7/2013 | Schreck |
| 8,506,622 B2 | 8/2013 | Bruszewski et al. |
| 8,870,938 B2 | 10/2014 | Shalev et al. |
| 2001/0000188 A1 | 4/2001 | Lenker et al. |
| 2001/0004705 A1 | 6/2001 | Killion et al. |
| 2001/0014823 A1 | 8/2001 | Ressemann et al. |
| 2001/0034550 A1 | 10/2001 | Buirge et al. |
| 2001/0037142 A1 | 11/2001 | Stelter et al. |
| 2001/0044647 A1 | 11/2001 | Pinchuk et al. |
| 2001/0044651 A1 | 11/2001 | Steinke et al. |
| 2001/0044652 A1 | 11/2001 | Moore |
| 2001/0047198 A1 | 11/2001 | Drasler et al. |
| 2001/0049550 A1 | 12/2001 | Martin et al. |
| 2001/0053930 A1 | 12/2001 | Kugler et al. |
| 2002/0040236 A1 | 4/2002 | Lau et al. |
| 2002/0052643 A1 | 5/2002 | Wholey et al. |
| 2002/0052644 A1 | 5/2002 | Shaolian et al. |
| 2002/0072790 A1 | 6/2002 | McGuckin, Jr. et al. |
| 2002/0099438 A1 | 7/2002 | Furst |
| 2002/0099441 A1 | 7/2002 | Dehdashtian |
| 2002/0107564 A1 | 8/2002 | Cox et al. |
| 2002/0111667 A1 | 8/2002 | Girton et al. |
| 2002/0123791 A1 | 9/2002 | Harrison |
| 2002/0156495 A1 | 10/2002 | Brenneman et al. |
| 2002/0156517 A1 | 10/2002 | Perouse |
| 2002/0173809 A1 | 11/2002 | Fleischman et al. |
| 2002/0183783 A1 | 12/2002 | Shadduck |
| 2002/0193864 A1 | 12/2002 | Khosravi et al. |

(56) References Cited

U.S. PATENT DOCUMENTS

| | | |
|---|---|---|
| 2002/0198585 A1 | 12/2002 | Wisselink |
| 2003/0033005 A1 | 2/2003 | Houser et al. |
| 2003/0040791 A1 | 2/2003 | Oktay |
| 2003/0065386 A1 | 4/2003 | Weadock |
| 2003/0068296 A1 | 4/2003 | Ricci et al. |
| 2003/0074055 A1 | 4/2003 | Haverkost |
| 2003/0093145 A1 | 5/2003 | Lawrence-Brown et al. |
| 2003/0125796 A1 | 7/2003 | Dong |
| 2003/0130720 A1 | 7/2003 | DePalma et al. |
| 2003/0144725 A1 | 7/2003 | Lombardi |
| 2003/0153944 A1 | 8/2003 | Phung et al. |
| 2003/0153968 A1 | 8/2003 | Geis et al. |
| 2003/0171771 A1 | 9/2003 | Anderson et al. |
| 2003/0191523 A1 | 10/2003 | Hojeibane |
| 2003/0199967 A1 | 10/2003 | Hartley et al. |
| 2003/0199968 A1 | 10/2003 | Ainsworth et al. |
| 2003/0204236 A1 | 10/2003 | Letort |
| 2003/0204242 A1 | 10/2003 | Zarins et al. |
| 2003/0204243 A1 | 10/2003 | Shiu |
| 2003/0212449 A1 | 11/2003 | Cox |
| 2003/0233117 A1 | 12/2003 | Adams et al. |
| 2003/0236567 A1 | 12/2003 | Elliot |
| 2004/0015227 A1 | 1/2004 | Vardi et al. |
| 2004/0015229 A1 | 1/2004 | Fulkerson et al. |
| 2004/0098091 A1 | 5/2004 | Erbel et al. |
| 2004/0106972 A1 | 6/2004 | Deaton |
| 2004/0106978 A1 | 6/2004 | Greenberg et al. |
| 2004/0117003 A1 | 6/2004 | Ouriel et al. |
| 2004/0133266 A1 | 7/2004 | Clerc et al. |
| 2004/0138735 A1 | 7/2004 | Shaolian et al. |
| 2004/0162606 A1 | 8/2004 | Thompson |
| 2004/0171978 A1 | 9/2004 | Shalaby |
| 2004/0181149 A1 | 9/2004 | Langlotz et al. |
| 2004/0215319 A1 | 10/2004 | Berra et al. |
| 2004/0215320 A1 | 10/2004 | Machek |
| 2004/0215327 A1 | 10/2004 | Doig et al. |
| 2004/0215332 A1 | 10/2004 | Frid |
| 2004/0260383 A1 | 12/2004 | Stelter et al. |
| 2005/0010246 A1 | 1/2005 | Streeter et al. |
| 2005/0033406 A1 | 2/2005 | Barnhart et al. |
| 2005/0049678 A1 | 3/2005 | Cocks et al. |
| 2005/0059923 A1 | 3/2005 | Gamboa |
| 2005/0065545 A1 | 3/2005 | Wallace |
| 2005/0085900 A1 | 4/2005 | Case et al. |
| 2005/0102018 A1 | 5/2005 | Carpenter et al. |
| 2005/0102021 A1 | 5/2005 | Osborne |
| 2005/0131517 A1 | 6/2005 | Hartley et al. |
| 2005/0137682 A1 | 6/2005 | Justino |
| 2005/0149166 A1 | 7/2005 | Schaeffer et al. |
| 2005/0154448 A1 | 7/2005 | Cully et al. |
| 2005/0159803 A1 | 7/2005 | Lad et al. |
| 2005/0165480 A1 | 7/2005 | Jordan et al. |
| 2005/0171598 A1 | 8/2005 | Schaeffer |
| 2005/0171599 A1 | 8/2005 | White |
| 2005/0177132 A1 | 8/2005 | Lentz et al. |
| 2005/0203606 A1 | 9/2005 | VanCamp |
| 2005/0216018 A1 | 9/2005 | Sennett |
| 2005/0222667 A1 | 10/2005 | Hunt |
| 2005/0222668 A1 | 10/2005 | Schaeffer et al. |
| 2005/0222669 A1 | 10/2005 | Purdy |
| 2005/0228480 A1 | 10/2005 | Douglas et al. |
| 2005/0234542 A1 | 10/2005 | Melsheimer |
| 2005/0266042 A1 | 12/2005 | Tseng |
| 2005/0273155 A1 | 12/2005 | Bahler et al. |
| 2005/0283188 A1 | 12/2005 | Loshakove et al. |
| 2006/0015170 A1 | 1/2006 | Jones et al. |
| 2006/0030921 A1 | 2/2006 | Chu |
| 2006/0052799 A1 | 3/2006 | Middleman et al. |
| 2006/0069426 A1 | 3/2006 | Weinberger |
| 2006/0095114 A1 | 5/2006 | Hartley et al. |
| 2006/0100684 A1 | 5/2006 | Elliott |
| 2006/0106406 A1 | 5/2006 | Weinberger |
| 2006/0116748 A1 | 6/2006 | Kaplan et al. |
| 2006/0149360 A1 | 7/2006 | Schwammenthal et al. |
| 2006/0155358 A1 | 7/2006 | LaDuca et al. |
| 2006/0155359 A1 | 7/2006 | Watson |
| 2006/0155366 A1 | 7/2006 | LaDuca et al. |
| 2006/0167476 A1 | 7/2006 | Burdulis, Jr. et al. |
| 2006/0173530 A1 | 8/2006 | Das |
| 2006/0190070 A1 | 8/2006 | Dieck et al. |
| 2006/0193892 A1 | 8/2006 | Furst et al. |
| 2006/0212113 A1 | 9/2006 | Shaolian et al. |
| 2006/0229709 A1 | 10/2006 | Morris et al. |
| 2006/0241740 A1 | 10/2006 | Vardi et al. |
| 2006/0271166 A1 | 11/2006 | Thill et al. |
| 2006/0276882 A1 | 12/2006 | Case et al. |
| 2006/0281966 A1 | 12/2006 | Peacock, III |
| 2007/0016281 A1 | 1/2007 | Melsheimer |
| 2007/0021822 A1 | 1/2007 | Boatman |
| 2007/0027526 A1 | 2/2007 | Demetriades et al. |
| 2007/0043425 A1 | 2/2007 | Hartley et al. |
| 2007/0050011 A1 | 3/2007 | Klein et al. |
| 2007/0055326 A1 | 3/2007 | Farley et al. |
| 2007/0055350 A1 | 3/2007 | Erickson et al. |
| 2007/0055358 A1 | 3/2007 | Krolik et al. |
| 2007/0055360 A1 | 3/2007 | Hanson et al. |
| 2007/0060989 A1 | 3/2007 | Deem et al. |
| 2007/0061002 A1 | 3/2007 | Paul, Jr. et al. |
| 2007/0073373 A1 | 3/2007 | Bonsignore |
| 2007/0088425 A1 | 4/2007 | Schaeffer |
| 2007/0112344 A1 | 5/2007 | Keilman |
| 2007/0135677 A1 | 6/2007 | Miller et al. |
| 2007/0142896 A1 | 6/2007 | Anderson et al. |
| 2007/0150051 A1 | 6/2007 | Maxime et al. |
| 2007/0156167 A1 | 7/2007 | Connors et al. |
| 2007/0162104 A1 | 7/2007 | Frid |
| 2007/0167898 A1 | 7/2007 | Peters et al. |
| 2007/0167955 A1 | 7/2007 | Maxime et al. |
| 2007/0168013 A1 | 7/2007 | Douglas |
| 2007/0168018 A1 | 7/2007 | Amplatz et al. |
| 2007/0179598 A1 | 8/2007 | Duerig |
| 2007/0185565 A1 | 8/2007 | Schwammenthal et al. |
| 2007/0207186 A1 | 9/2007 | Scanlon et al. |
| 2007/0208410 A1 | 9/2007 | Berra et al. |
| 2007/0213805 A1 | 9/2007 | Schaeffer et al. |
| 2007/0213807 A1 | 9/2007 | Roubin et al. |
| 2007/0219610 A1 | 9/2007 | Israel |
| 2007/0219627 A1 | 9/2007 | Chu et al. |
| 2007/0225797 A1 | 9/2007 | Krivoruhko |
| 2007/0233229 A1 | 10/2007 | Berra et al. |
| 2007/0237973 A1 | 10/2007 | Purdy et al. |
| 2007/0244542 A1 | 10/2007 | Greenan et al. |
| 2007/0244543 A1 | 10/2007 | Mitchell |
| 2007/0244547 A1 | 10/2007 | Greenan |
| 2007/0250154 A1 | 10/2007 | Greenberg et al. |
| 2007/0255388 A1 | 11/2007 | Rudakov et al. |
| 2008/0002871 A1 | 1/2008 | Gunzert-Marx et al. |
| 2008/0015673 A1 | 1/2008 | Chuter |
| 2008/0058918 A1 | 3/2008 | Watson |
| 2008/0109058 A1 | 5/2008 | Greenberg et al. |
| 2008/0109066 A1 | 5/2008 | Quinn |
| 2008/0114444 A1 | 5/2008 | Yu |
| 2008/0114445 A1 | 5/2008 | Melsheimer et al. |
| 2008/0147173 A1 | 6/2008 | Mciff et al. |
| 2008/0167704 A1 | 7/2008 | Wright et al. |
| 2008/0195190 A1 | 8/2008 | Bland et al. |
| 2008/0195191 A1 | 8/2008 | Luo et al. |
| 2008/0215134 A1 | 9/2008 | Lawrence-Brown |
| 2008/0249598 A1 | 10/2008 | Sherry |
| 2008/0262595 A1 | 10/2008 | Chu et al. |
| 2008/0269789 A1 | 10/2008 | Eli |
| 2008/0275540 A1 | 11/2008 | Wen |
| 2008/0275542 A1 | 11/2008 | LaDuca et al. |
| 2008/0288044 A1 | 11/2008 | Osborne |
| 2008/0294234 A1 | 11/2008 | Hartley et al. |
| 2008/0300665 A1 | 12/2008 | Lootz et al. |
| 2008/0319528 A1 | 12/2008 | Yribarren et al. |
| 2009/0012597 A1 | 1/2009 | Doig et al. |
| 2009/0012602 A1 | 1/2009 | Quadri |
| 2009/0030497 A1 | 1/2009 | Metcalf et al. |
| 2009/0030502 A1 | 1/2009 | Sun et al. |
| 2009/0048663 A1 | 2/2009 | Greenberg |
| 2009/0054967 A1 | 2/2009 | Das |
| 2009/0062899 A1 | 3/2009 | Dang et al. |

(56) References Cited

U.S. PATENT DOCUMENTS

| | | |
|---|---|---|
| 2009/0069881 A1 | 3/2009 | Chalekian et al. |
| 2009/0069882 A1 | 3/2009 | Venturelli et al. |
| 2009/0082841 A1 | 3/2009 | Zacharias et al. |
| 2009/0082847 A1 | 3/2009 | Zacharias et al. |
| 2009/0099640 A1 | 4/2009 | Weng |
| 2009/0099647 A1 | 4/2009 | Glimsdale et al. |
| 2009/0099648 A1 | 4/2009 | Yu |
| 2009/0099649 A1 | 4/2009 | Chobotov et al. |
| 2009/0099650 A1 | 4/2009 | Bolduc et al. |
| 2009/0105809 A1 | 4/2009 | Lee et al. |
| 2009/0112233 A1 | 4/2009 | Xiao |
| 2009/0125096 A1 | 5/2009 | Chu et al. |
| 2009/0138067 A1 | 5/2009 | Pinchuk et al. |
| 2009/0149877 A1 | 6/2009 | Hanson et al. |
| 2009/0164001 A1 | 6/2009 | Biggs et al. |
| 2009/0171437 A1 | 7/2009 | Brocker et al. |
| 2009/0192587 A1 | 7/2009 | Frid |
| 2009/0227997 A1 | 9/2009 | Wang et al. |
| 2009/0240316 A1 | 9/2009 | Bruszewski |
| 2009/0248134 A1 | 10/2009 | Dierking et al. |
| 2009/0254170 A1 | 10/2009 | Hartley et al. |
| 2009/0259290 A1 | 10/2009 | Bruszewski et al. |
| 2009/0287145 A1 | 11/2009 | Cragg et al. |
| 2010/0004728 A1 | 1/2010 | Rao et al. |
| 2010/0029608 A1 | 2/2010 | Finley et al. |
| 2010/0063575 A1 | 3/2010 | Shalev et al. |
| 2010/0070019 A1 | 3/2010 | Shalev |
| 2010/0082091 A1 | 4/2010 | Berez et al. |
| 2010/0161025 A1 | 6/2010 | Kuppurathanam et al. |
| 2010/0161026 A1 | 6/2010 | Brocker et al. |
| 2010/0168838 A1 | 6/2010 | Hartley et al. |
| 2010/0211159 A1 | 8/2010 | Schmid et al. |
| 2010/0256725 A1 | 10/2010 | Rasmussen |
| 2010/0274187 A1 | 10/2010 | Argentine |
| 2010/0292774 A1 | 11/2010 | Shalev |
| 2010/0318171 A1 | 12/2010 | Porter et al. |
| 2011/0022153 A1 | 1/2011 | Schreck et al. |
| 2011/0040366 A1 | 2/2011 | Goetz et al. |
| 2011/0093002 A1 | 4/2011 | Rucker et al. |
| 2011/0125251 A1 | 5/2011 | Cottone et al. |
| 2011/0208289 A1 | 8/2011 | Shalev |
| 2011/0208296 A1 | 8/2011 | Duffy et al. |
| 2011/0208297 A1 | 8/2011 | Tuval et al. |
| 2011/0208298 A1 | 8/2011 | Tuval et al. |
| 2011/0218604 A1 | 9/2011 | Arbefeuille et al. |
| 2011/0218609 A1 | 9/2011 | Chobotov et al. |
| 2011/0218617 A1 | 9/2011 | Nguyen et al. |
| 2011/0257720 A1 | 10/2011 | Peterson et al. |
| 2011/0264184 A1 | 10/2011 | Heltai |
| 2011/0288622 A1 | 11/2011 | Chan et al. |
| 2011/0301702 A1 | 12/2011 | Rust et al. |
| 2011/0319983 A1 | 12/2011 | Zhu et al. |
| 2012/0150274 A1 | 6/2012 | Shalev et al. |
| 2012/0172929 A1 | 7/2012 | Shalev |
| 2012/0179236 A1 | 7/2012 | Benary et al. |
| 2012/0185031 A1 | 7/2012 | Ryan et al. |
| 2012/0271401 A1 | 10/2012 | Bruszewski et al. |
| 2012/0310324 A1 | 12/2012 | Benary et al. |
| 2012/0316634 A1 | 12/2012 | Shalev et al. |
| 2012/0323305 A1 | 12/2012 | Benary et al. |
| 2012/0330399 A1 | 12/2012 | Shalev et al. |
| 2013/0013050 A1 | 1/2013 | Shalev et al. |
| 2013/0013051 A1 | 1/2013 | Benary |
| 2013/0035751 A1 | 2/2013 | Shalev |
| 2013/0090722 A1 | 4/2013 | Shalev et al. |
| 2013/0116773 A1 | 5/2013 | Roeder et al. |
| 2013/0131783 A1 | 5/2013 | Shalev et al. |
| 2013/0204343 A1 | 8/2013 | Shalev |
| 2013/0261994 A1 | 10/2013 | Raz et al. |
| 2013/0289587 A1 | 10/2013 | Shalev |
| 2013/0297005 A1 | 11/2013 | Shalev |
| 2014/0052236 A1 | 2/2014 | Shalev |
| 2014/0172072 A1 | 6/2014 | Shalev |
| 2014/0288635 A1 | 9/2014 | Shalev |
| 2014/0324154 A1 | 10/2014 | Shalev |

FOREIGN PATENT DOCUMENTS

| | | |
|---|---|---|
| CN | 2817770 | 9/2006 |
| CN | 201058061 | 5/2008 |
| EP | 1177780 | 2/2002 |
| EP | 1325716 | 7/2003 |
| EP | 1470797 | 10/2004 |
| EP | 1759666 | 3/2007 |
| EP | 1961401 | 8/2008 |
| EP | 2266509 | 12/2010 |
| EP | 2298248 | 3/2011 |
| EP | 2702964 A1 | 3/2014 |
| JP | 2002253682 | 9/2002 |
| WO | 9639104 A1 | 12/1996 |
| WO | 9934748 | 7/1999 |
| WO | 9951165 A1 | 10/1999 |
| WO | 00/42949 A2 | 7/2000 |
| WO | 2002083038 | 10/2002 |
| WO | 2003099108 | 12/2003 |
| WO | 2004017868 | 3/2004 |
| WO | 2005002466 | 1/2005 |
| WO | 2005037138 | 4/2005 |
| WO | 2005041781 | 5/2005 |
| WO | 2005041783 | 5/2005 |
| WO | 2005046524 | 5/2005 |
| WO | 2006007389 | 1/2006 |
| WO | 2006028925 | 3/2006 |
| WO | 2006070372 | 7/2006 |
| WO | 2006088905 A1 | 8/2006 |
| WO | 2006130755 A2 | 12/2006 |
| WO | 2007022495 | 2/2007 |
| WO | 2007039587 | 4/2007 |
| WO | 2007084547 | 7/2007 |
| WO | 2007144782 | 12/2007 |
| WO | 2008008291 | 1/2008 |
| WO | 2008035337 | 3/2008 |
| WO | 2008042266 | 4/2008 |
| WO | 2008047092 | 4/2008 |
| WO | 2008047354 | 4/2008 |
| WO | 2008051704 A1 | 5/2008 |
| WO | 2008053469 | 5/2008 |
| WO | 2008066923 | 6/2008 |
| WO | 2008107885 | 9/2008 |
| WO | 2008140796 | 11/2008 |
| WO | 2009078010 | 6/2009 |
| WO | 2009116041 | 9/2009 |
| WO | 2009116042 | 9/2009 |
| WO | 2009118733 | 10/2009 |
| WO | 2010/027704 | 3/2010 |
| WO | 2010024869 | 3/2010 |
| WO | 2010024879 | 3/2010 |
| WO | 2010031060 | 3/2010 |
| WO | 2010042210 A1 | 4/2010 |
| WO | 2010045238 | 4/2010 |
| WO | 2010062355 | 6/2010 |
| WO | 2010088776 | 8/2010 |
| WO | 2010128162 | 11/2010 |
| WO | 2010150208 | 12/2010 |
| WO | 2011004374 | 1/2011 |
| WO | 2011007354 | 1/2011 |
| WO | 2011055364 | 5/2011 |
| WO | 2011064782 | 6/2011 |
| WO | 2011067764 | 6/2011 |
| WO | 2011070576 | 6/2011 |
| WO | 2011080738 | 7/2011 |
| WO | 2011095979 | 8/2011 |
| WO | 2011106532 | 9/2011 |
| WO | 2011106533 | 9/2011 |
| WO | 2011106544 | 9/2011 |
| WO | 2012049679 | 4/2012 |
| WO | 2012104842 | 8/2012 |
| WO | 2012111006 | 8/2012 |
| WO | 2012117395 | 9/2012 |
| WO | 2012176187 | 12/2012 |
| WO | 2013005207 | 1/2013 |
| WO | 2013030818 | 3/2013 |
| WO | 2013030819 | 3/2013 |
| WO | 2013065040 | 5/2013 |
| WO | 2013084235 | 6/2013 |

(56) References Cited

FOREIGN PATENT DOCUMENTS

| WO | 2013171730 | 11/2013 |
|---|---|---|
| WO | 2014020609 | 2/2014 |
| WO | 2014108895 | 7/2014 |
| WO | 2014141232 | 9/2014 |
| WO | 2014188412 | 11/2014 |

OTHER PUBLICATIONS

European Search Report dated May 23, 2016, which issued during the prosecution of Applicant's European App No. 10832752.9.
An Office Action dated Jul. 22, 2016, which issued during the prosecution of Chinese Patent Application No. 201480012648.9.
An Office Action dated Aug. 3, 2016, which issued during the prosecution of U.S. Appl. No. 14/241,793.
A non-final Office Action dated Feb. 28, 2014 in U.S. Appl. No. 13/512,778.
An International Preliminary Report on Patentability dated Jan. 7, 2014, which issued during the prosecution of Applicant's PCT/IL2012/000269.
An International Preliminary Report on Patentability dated Jan. 4, 2012, which issued during the prosecution of Applicant's PCT/IB2010/052861.
An International Preliminary Report on Patentability dated Dec. 23, 2013, which issued during the prosecution of Applicant's PCT/IL2012/000241.
An International Preliminary Report on Patentability dated Aug. 6, 2013, which issued during the prosecution of Applicant's PCT/IL2012/000060.
An English translation of an Office Action dated Oct. 8, 2014, which issued during the prosecution of Chinese Patent Application No. 201080036970.7.
An English translation of an Office Action dated Nov. 28, 2013, which issued during the prosecution of Chinese Patent Application No. 200880126889.0.
An English translation of an Office Action dated May 16, 2014, which issued during the prosecution of Chinese Patent Application No. 200880126889.0.
An English translation of an Office Action dated Aug. 25, 2011, which issued during the prosecution of Chinese Patent Application No. 200880014919.9.
An English translation of an Office Action dated Feb. 16, 2013, which issued during the prosecution of Chinese Patent Application No. 200880126889.0.
An International Preliminary Report on Patentability dated Jan. 10, 2012, which issued during the prosecution of Applicant's PCT/IL2010/000549.
An International Preliminary Report on Patentability dated Jan. 17, 2012, which issued during the prosecution of Applicant's PCT/IL2010/000564.
A Notice of Allowance dated Aug. 2, 2012, which issued during the prosecution of U.S. Appl. No. 12/529,936.
An Advisory Action dated Feb. 13, 2014, which issued during the prosecution of Applicant's U.S. Appl. No. 13/807,880.
An International Preliminary Report on Patentability dated Jun. 5, 2012, which issued during the prosecution of Applicant's PCT/IL2010/000999.
An International Preliminary Report on Patentability dated Jun. 5, 2012, which issued during the prosecution of Applicant's PCT/IL2010/001018.
An International Preliminary Report on Patentability dated Jun. 10, 2014, which issued during the prosecution of Applicant's PCT/IL2012/050506.
A Notice of Allowance issued in U.S. Appl. No. 13/807,906 dated Oct. 10, 2014.
A Restriction Requirement dated Jan. 29, 2014, which issued during the prosecution of U.S. Appl. No. 13/519,971.
An International Preliminary Report on Patentability dated Jun. 12, 2012, which issued during the prosecution of Applicant's PCT/IL2010/001037.
An International Preliminary Report on Patentability dated Mar. 4, 2014, which issued during the prosecution of Applicant's PCT/IL2012/000300.
An International Preliminary Report on Patentability dated May 6, 2014, which issued during the prosecution of Applicant's PCT/IL2012/050424.
An International Preliminary Report on Patentability dated May 8, 2012, which issued during the prosecution of Applicant's PCT/IL2010/000917.
An International Preliminary Report on Patentability dated Nov. 18, 2014, which issued during the prosecution of Applicant's PCT/IL2012/000190.
An International Search Report and a Written Opinion both dated Apr. 18, 2011, which issued during the prosecution of Applicant's PCT/IL2010/001037.
An International Search Report and a Written Opinion both dated Aug. 4, 2011, which issued during the prosecution of Applicant's PCT/IL2010/000999.
An International Search Report and a Written Opinion both dated Aug. 31, 2012, which issued during the prosecution of Applicant's PCT/IL2012/000148.
An International Search Report and a Written Opinion both dated Dec. 3, 2010, which issued during the prosecution of Applicant's PCT/IL2010/000564.
An International Search Report and a Written Opinion both dated Feb. 4, 2011, which issued during the prosecution of Applicant's PCT/IB2010/052861.
An International Search Report and a Written Opinion both dated Jul. 13, 2012, which issued during the prosecution of Applicant's PCT/IL2012/000083.
An International Search Report and a Written Opinion both dated Jul. 17, 2012, which issued during the prosecution of Applicant's PCT/IL2012/000095.
An International Search Report and a Written Opinion both dated Jun. 14, 2013, which issued during the prosecution of Applicant's PCT/IL2012/050506.
An International Search Report and a Written Opinion both dated Jun. 28, 2011, which issued during the prosecution of Applicant's PCT/IL2011/000135.
An International Search Report and a Written Opinion both dated Jun. 30, 2009, which issued during the prosecution of Applicant's PCT/IL2008/001621.
An International Search Report and a Written Opinion both dated Mar. 10, 2011, which issued during the prosecution of Applicant's PCT/IL2010/000917.
An International Search Report and a Written Opinion both dated Mar. 11, 2009, which issued during the prosecution of Applicant's PCT/IL2007/001312.
An International Search Report and a Written Opinion both dated Mar. 15, 2013, which issued during the prosecution of Applicant's PCT/IL2012/050424.
An International Preliminary Report on Patentability dated Sep. 3, 2013, which issued during the prosecution of Applicant's PCT/IL2012/000095.
An International Search Report and a Written Opinion both dated Mar. 30, 2011, which issued during the prosecution of Applicant's PCT/IL2010/001018.
An International Search Report and a Written Opinion both dated May 23, 2011, which issued during the prosecution of Applicant's PCT/IL2010/001087.
An International Search Report and a Written Opinion both dated Nov. 5, 2010, which issued during the prosecution of Applicant's PCT/IL2010/000549.
An International Search Report and a Written Opinion both dated Nov. 27, 2012, which issued during the prosecution of Applicant's PCT/IL2012/000300.
An International Search Report and a Written Opinion both dated Oct. 1, 2012, which issued during the prosecution of Applicant's PCT/IL2012/000241.
An International Search Report and a Written Opinion both dated Oct. 4, 2012, which issued during the prosecution of Applicant's PCT/IL2012/000269.

(56) References Cited

OTHER PUBLICATIONS

An International Search Report and a Written Opinion both dated Sep. 6, 2012, which issued during the prosecution of Applicant's PCT/IL2012/000190.
An International Search Report and a Written Opinion both dated Apr. 28, 2014, which issued during the prosecution of Applicant's PCT/IL2014/050019.
An International Search Report dated Jul. 30, 2014, which issued during the prosecution of Applicant's PCT/IL2014/050174.
An International Search Report and a Written Opinion both dated Sep. 24, 2012, which issued during the prosecution of Applicant's PCT/IL2012/000060.
An International Search Report and a Written Opinion both dated Sep. 29, 2008, which issued during the prosecution of Applicant's PCT/IL2008/000287.
An International Search Report dated Nov. 28, 2013, which issued during the prosecution of Applicant's PCT/IL2013/050656.
Notice of allowance dated Jun. 24, 2014, which issued during the prosecution of Applicant's U.S. Appl. No. 13/380,278.
An International Search Report dated Nov. 28, 2014, which issued during the prosecution of Applicant's PCT/IL2014/050434.
An Interview Summary dated Feb. 28, 2012, which issued during the prosecution of U.S. Appl. No. 12/529,936.
An Office Action dated Apr. 10, 2014, which issued during the prosecution of Applicant's U.S. Appl. No. 13/807,906.
An Office Action dated Apr. 24, 2014, which issued during the prosecution of Applicant's U.S. Appl. No. 13/380,278.
An Office Action dated Dec. 2, 2013, which issued during the prosecution of U.S. Appl. No. 13/807,880.
An office Action dated Feb. 25. 2013, which issued during the prosecution of U.S. Appl. No. 13/031,871.
An Office Action dated Feb. 27, 2013, which issued during the prosecution of U.S. Appl. No. 12/808,037.
An Office Action dated Jul. 24, 2014, which issued during the prosecution of Canadian Patent Application No. 2768228.
An Office Action dated Jul. 28, 2014, which issued during the prosecution of U.S. Appl. No. 13/031,871.
An Office Action dated Jun. 19, 2012, which issued during the prosecution of U.S. Appl. No. 12/808,037.
An Office Action dated Mar. 24, 2011, which issued during the prosecution of U.S. Appl. No. 12/529,936.
An Office Action dated Mar. 28, 2014, which issued during the prosecution of Applicant's U.S. Appl. No. 13/519,971.
An Office Action dated Apr. 27, 2011, which issued during the prosecution of U.S. Appl. No. 12/447,684.
An Office Action dated Apr. 28, 2014, which issued during the prosecution of Applicant's U.S. Appl. No. 13/939,798.
An Office Action dated May 20, 2013, which issued during the prosecution of U.S. Appl. No. 13/807,880.
An Office Action dated Nov. 12, 2010, which issued during the prosecution of U.S. Appl. No. 12/447,684.
An Office Action dated Nov. 3, 2014, which issued during the prosecution of Canadian Patent Application No. 2767596.
An Office Action dated Nov. 19, 2013, which issued during the prosecution of U.S. Appl. No. 13/663,117.
An Office Action dated Oct. 11, 2012, which issued during the prosecution of U.S. Appl. No. 13/031,871.
U.S. Appl. No. 61/219,758, filed Jun. 23, 2009.
U.S. Appl. No. 61/221,074, filed Jun. 28, 2009.
U.S. Appl. No. 61/496,613, filed Jun. 14, 2011.
An Office Action dated Oct. 28, 2011, which issued during the prosecution of U.S. Appl. No. 12/529,936.
U.S. Appl. No. 61/505,132, filed Jul. 7, 2011.
U.S. Appl. No. 61/678,182, filed Aug. 1, 2012.
U.S. Appl. No. 61/529,931, filed Sep. 1, 2011.
U.S. Appl. No. 61/553,209, filed Oct. 30, 2011.
U.S. Appl. No. 61/499,195, filed Jun. 21, 2011.
U.S. Appl. No. 61/749,965, filed Jan. 8, 2013.
Notice of Allowance dated Jun. 18, 2013, which issued during the prosecution of U.S. Appl. No. 13/523,296.
Office Action dated Oct. 27, 2014 in Canadian Patent Application No. 2,785,953.
Ryhanen J., in "Biocompatibility evaluation of nickel-titanium shape memory metal alloy," Academic Dissertation, Faculty of Medicine, Department of Surgery, University of Oulu, Finland (May 1999).
Supplementary European Search Report dated Dec. 13, 2012, which issued during the prosecution of Applicant's European App No. 08719912.1.
Supplementary European Search Report dated Jun. 23, 2014, which issued during the prosecution of Applicant's European App No. 12741804.4.
Written Opinion dated Nov. 26, 2013, which issued during the prosecution of Applicant's PCT/IL2013/050656.
"E-vita open plus" product brochure (JOTEC GmbH, Hechingen, Germany), 2010.
An Office action dated Sep. 4, 2014, from the U.S. Patent and Trademark Office in counterpart U.S. Appl. No. 13/519,971.
European Office Action dated Dec. 17, 2014 in European Patent Application No. 12803376.8.
An Office action dated Feb. 5, 2015, from the U.S. Patent and Trademark Office in counterpart U.S. Appl. No. 13/384,075.
European Search Report dated Feb. 24, 2014 in European Patent Application No. 12803376.8.
Fattori et al., Degenerative aneurysm of the descending aorta. Endovascular Treatment. pp. 1-11, 2007, European Association for Cardio-Thoracic Surgery.
International Preliminary Report on Patentability dated Jan. 12, 2010 in corresponding International Application No. PCT/IL2008/000287.
Fonseca A et al., "Intravascular ultrasound assessment of the novel AngioSculpt scoring balloon catheter for the treatment of complex coronary lesions," J Invasive Cardiol 20(1):21-7 (Jan. 2008).
Van Prehn J et al., "Oversizing of aortic stent grafts for abdominal aneurysm repair: a systematic review of the benefits and risks," Eur J Vasc Endovasc Surg. Jul. 2009;38(I):42-53. Epub May 9, 2009 (abstract only).
Invitation to Pay Additional Fees dated May 13, 2014, which issued during the prosecution of Applicant's PCT/IL2014/050019.
Invitation to Pay Additional Fees dated May 8, 2014, which issued during the prosecution of Applicant's PCT/IL2014/50174.
Khlif H et al., "Contribution to the Improvement of Textile Vascular Prostheses Crimping," Trends in Applied Sciences Research 6(9):1019-1027 (2011).
U.S. Appl. No. 61/775,964, filed Mar. 11, 2013.
U.S. Appl. No. 61/826,544, filed May 23, 2013.
U.S. Appl. No. 61/906,014, filed Nov. 19, 2013.
U.S. Appl. No. 61/926,533, filed Jan. 13, 2014.
U.S. Appl. No. 61/528,242, filed Aug. 28, 2011.
An Office Action dated Aug. 15, 2014, which issued during the prosecution of Applicant's U.S. Appl. No. 13/939,798.
U.S. Appl. No. 61/566,654, filed Dec. 4, 2011.
An English translation of an Office Action dated Mar. 19, 2015, which issued during the prosecution of Chinese Patent Application No. 201080036970.7.
A Notice of Allowance dated Jan. 20, 2015, which issued during the prosecution of U.S. Appl. No. 13/383,128.
A Notice of Allowance dated Nov. 7, 2014, which issued during the prosecution of U.S. Appl. No. 13/512,778.
An Office Action dated Aug. 15, 2014, which issued during the prosecution of U.S. Appl. No. 13/512,778.
An International Search Report and a Written Opinion both dated Mar. 18, 2015, which issued during the prosecution of Applicant's PCT/IL2014/050973.
An Office Action dated Apr. 14, 2015, which issued during the prosecution of U.S. Appl. No. 14/130,213.
An International Preliminary Report on Patentability dated Feb. 3, 2015, which issued during the prosecution of Applicant's PCT/IL2013/050656.
A Notice of Allowance dated Jan. 7, 2014, which issued during the prosecution of U.S. Appl. No. 13/663,117.
An Office Action dated Mar. 26, 2015, which issued during the prosecution of U.S. Appl. No. 13/514,240.

(56) References Cited

OTHER PUBLICATIONS

Supplementary European Search Report dated Oct. 31, 2014, which issued during the prosecution of Applicant's European App No. 12752054.2.
An Office Action dated Sep. 2, 2014, which issued during the prosecution of U.S. Appl. No. 12/447,684.
U.S. Appl. No. 61/448,199, filed Mar. 2, 2011.
U.S. Appl. No. 61/014,031, filed Dec. 15, 2007.
An Examiner Interview Summary dated Dec. 13, 2010, which issued during the prosecution of U.S. Appl. No. 12/447,684.
An Office Action dated Mar. 21, 2012, which issued during the prosecution of U.S. Appl. No. 12/808,037.
An Office Action dated May 22, 2013, which issued during the prosecution of U.S. Appl. No. 12/808,037.
U.S. Appl. No. 60/863,373, filed Oct. 29, 2006.
An International Preliminary Report on Patentability dated Aug. 21, 2013, which issued during the prosecution of Applicant's PCT/IL2012/000083.
A non-final office action issued in U.S. Appl. No. 14/241,793, dated Feb. 1, 2016.
A final office action issued in U.S. Appl. No. 14/240,600, dated Mar. 7, 2016.
A non-final office action issued in U.S. Appl. No. 14/362,194, dated Mar. 28, 2016.
Scurr et al., "Fenestrated Aortic Stent Grafts", Seminars in Interventional Radiology, vol. 24 No. 2, Jun. 2007, pp. 211-220.
An International Search Report and Written Opinion in PCT/IL2016/051207, dated Jan. 19, 2017.
An extended European search report in European Appl. 10791726.2, dated Mar. 15, 2017.

\* cited by examiner

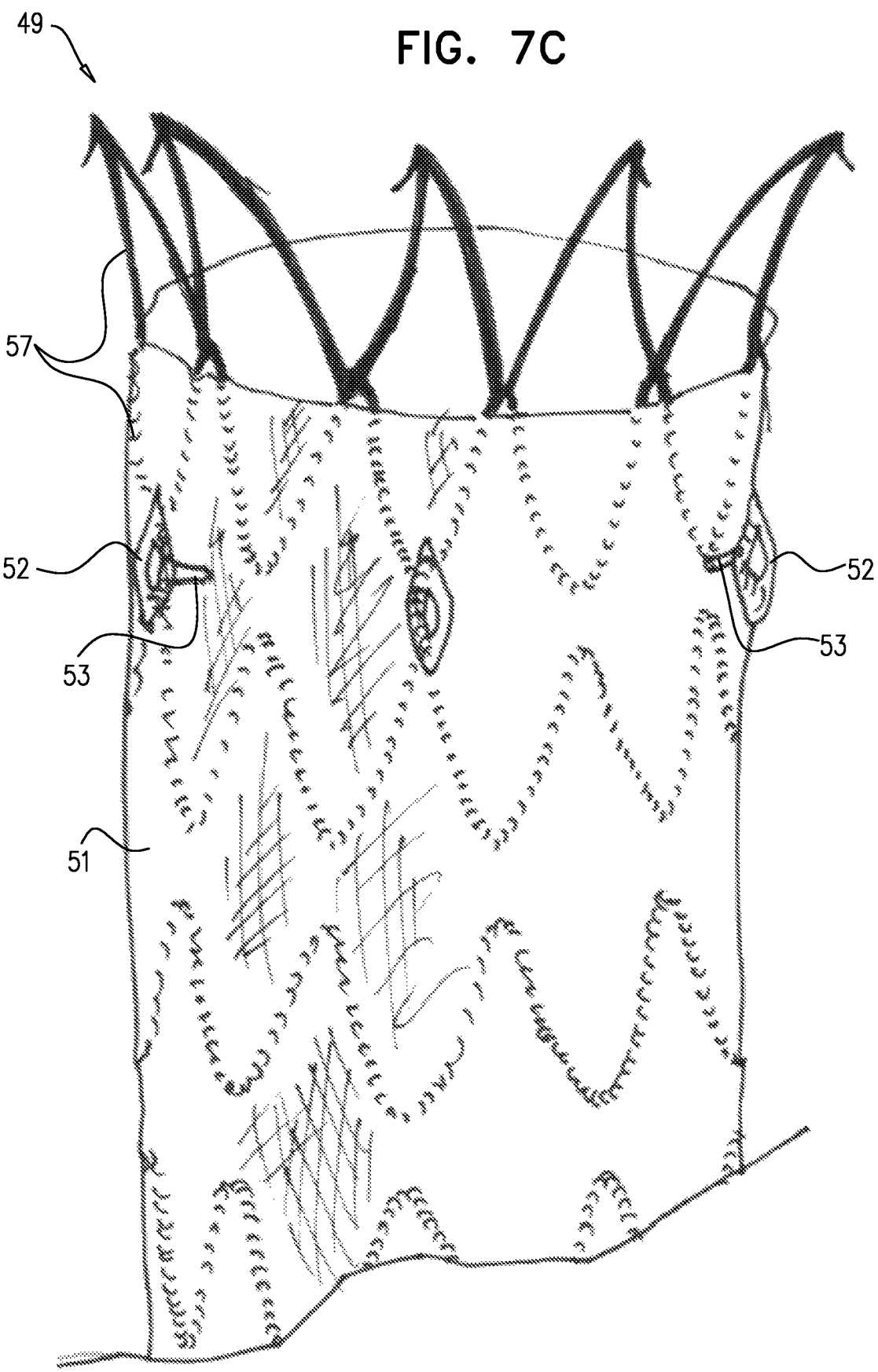

FIG. 15A
FIG. 15B
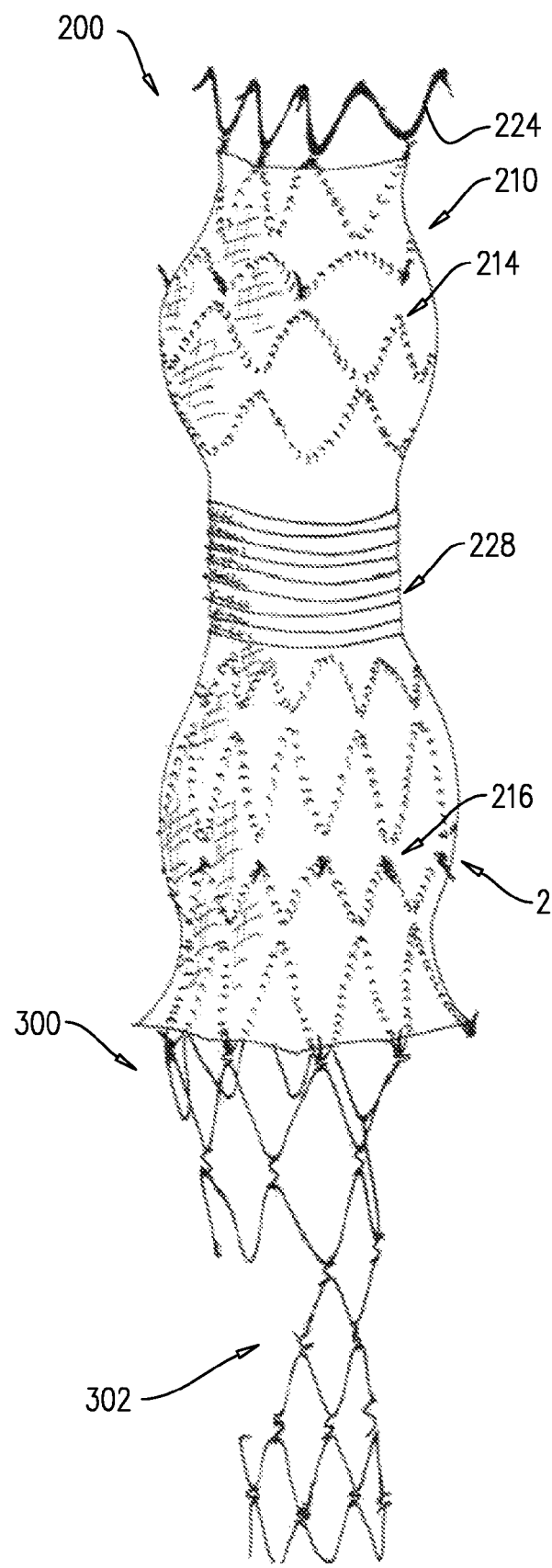
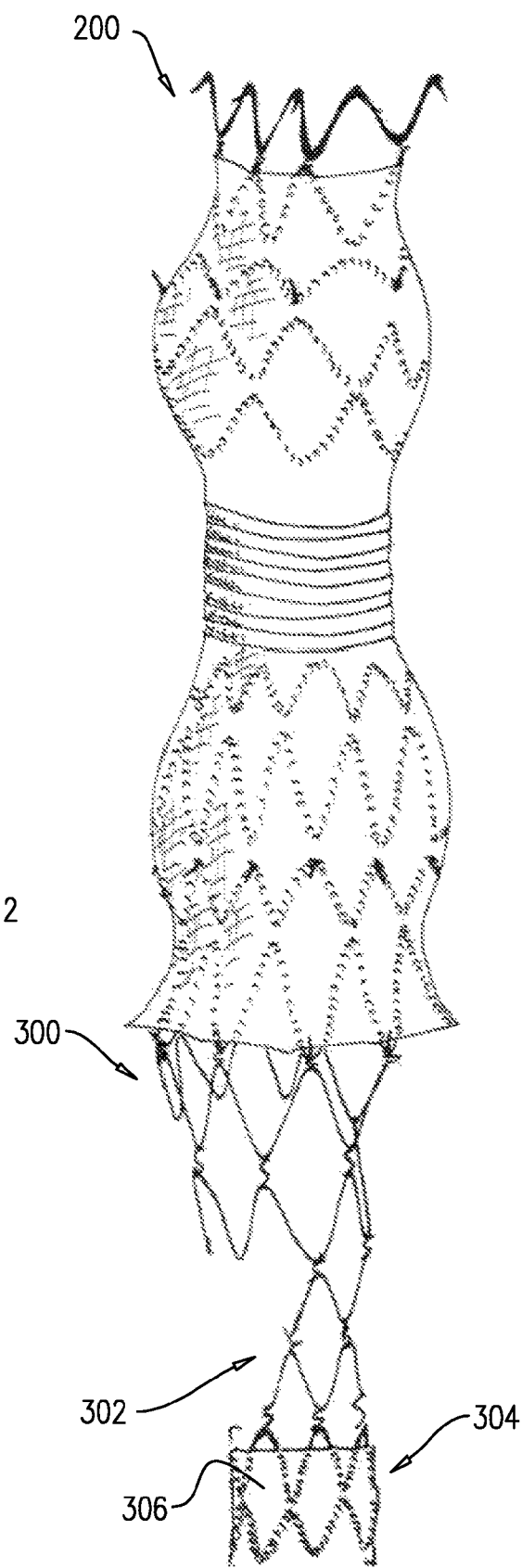

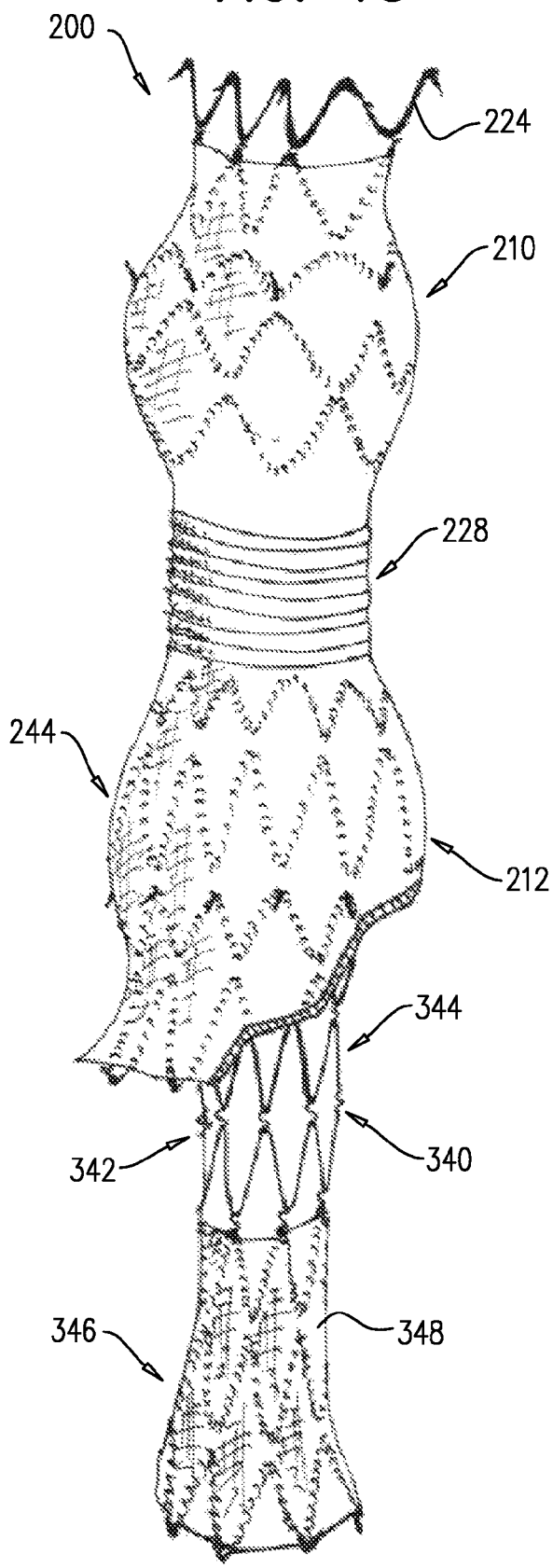
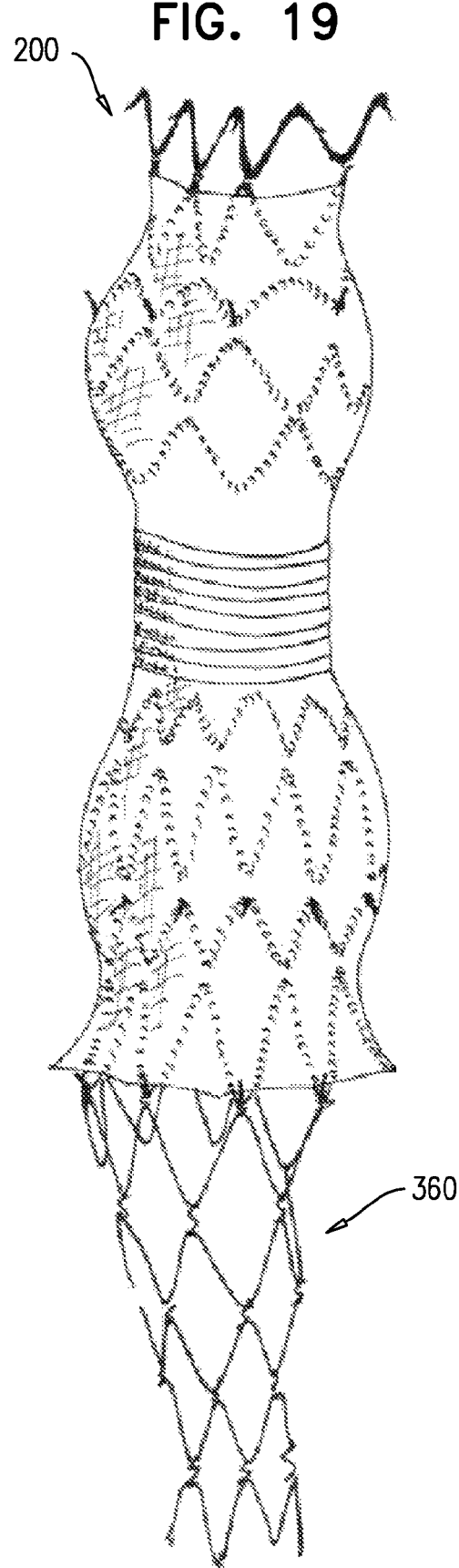
FIG. 18
FIG. 19

VASCULAR PROSTHESIS FOR TREATING ANEURYSMS

CROSS-REFERENCE TO RELATED APPLICATIONS

The present patent application is a continuation of U.S. application Ser. No. 13/380,278, filed Mar. 1, 2012, now U.S. Pat. No. 8,870,938, which is the U.S. national stage of PCT/IB2010/052861, filed Jun. 23, 2010, which published as PCT Publication WO 2010/150208 and which claims priority from: (a) U.S. Provisional Application 61/219,758, filed Jun. 23, 2009, entitled, "Vascular prostheses with improved sealing mechanisms and methods of using such devices," and (b) U.S. Provisional Application 61/221,074, filed Jun. 28, 2009, entitled, "A unilumen based system for endovascular abdominal aneurysm repair and methods for using the same." Both of these provisional applications are incorporated herein by reference.

FIELD OF THE APPLICATION

This present application relates generally to prostheses and surgical methods, and specifically to tubular prostheses, including endovascular grafts and stent-grafts, and surgical techniques for using the prostheses to maintain patency of body passages such as blood vessels, and treating aneurysms.

BACKGROUND OF THE APPLICATION

Endovascular prostheses are sometimes used to treat aortic aneurysms. Such treatment includes implanting a stent or stent-graft within the diseased vessel to bypass the anomaly. An aneurysm is a sac formed by the dilation of the wall of the artery. Aneurysms may be congenital, but are usually caused by disease or, occasionally, by trauma. Aortic aneurysms which commonly form between the renal arteries and the iliac arteries are referred to as abdominal aortic aneurysms ("AAAs"). Other aneurysms occur in the aorta, such as thoracic aortic aneurysms ("TAAs") and aortic uni-iliac ("AUI") aneurysms.

"Endoleak" is the persistent flow of blood into the aneurismal sac after implantation of an endovascular prosthesis. The management of some types of endoleak remains controversial, although most can be successfully occluded with surgery, further stent implantation, or embolization. Four types of endoleaks have been defined, based upon their proposed etiology, as described below.

A type I endoleak, which occurs in up to 10 percent of endovascular aortic aneurysm repairs, is due to an incompetent seal at either the proximal or distal attachment sites of the vascular prosthesis, resulting in blood flow at the end of the prosthesis into the aneurismal sac. Etiologies include undersizing of the diameter of the endograft at the attachment site and ineffective attachment to a vessel wall that is heavily calcified or surrounded by thick thrombus. Type I failures have also been found to be caused by a continual expansion of the aneurysm neck (the portion of the aorta extending cephalad or caudad from the aneurysm, and is not dilated). This expansion rate has been estimated to be about one millimeter per year. Because the aneurysm neck expands beyond the natural resting diameter of the prosthesis, one or more passageways are defined about the prosthesis in communication with the aneurismal sac. Additionally, Type I endoleaks may be caused when circular prostheses are implanted in non-circular aortic lumens, which may be caused by irregular vessel formation and/or calcified topography of the lumen of the aorta.

Type I endoleaks may occur immediately after placement of the prosthesis, or may be delayed. A delayed type I endoleak may be seen during follow-up studies if the prosthesis is deployed into a diseased segment of aorta that dilates over time, leading to a breach in the seal at the attachment site.

Type I endoleaks must be repaired as soon as they are discovered, because the aneurismal sac remains exposed to systemic pressure, predisposing to aneurysmal rupture, and spontaneous closure of the leak is rare. If discovered at the time of initial placement, repair may consist of reversal of anticoagulation and reinflation of the deployment balloon for an extended period of time. These leaks may also be repaired with small extension grafts that are placed over the affected end. These methods are usually sufficient to exclude the aneurysm. Conversion to an open surgical repair may be needed in the rare situation in which the leak is refractory to percutaneous treatment.

Type II endoleaks are the most prevalent type, occurring in 10 to 25 percent of endovascular aortic aneurysm repairs, and are characterized by flow into and out of the aneurismal sac from patent branch vessels. These endoleaks are most often identified on the post procedural CT, in which these leaks appear as collections of contrast outside of the endograft, but within the aneurismal sac. The most frequent sources of type II endoleaks are collateral backflow through patent lumbar arteries and a patent inferior mesenteric artery. Because the sac fills through a collateral network, the endoleak may not be visualized on the arterial phase of CT scanning; delayed imaging is thus required.

Type III and type IV endoleaks are much less common. Type III endoleaks represent flow into the aneurismal sac from separation between components of a modular system, or tears in the endograft fabric. Type IV endoleaks are due to egress of blood through the pores in the fabric. Type IV leaks heal spontaneously, while type III leaks are repaired with an additional endograft to eliminate systemic flow and pressure in the aneurysm.

As can be readily appreciated, even with the successful implantation of an endovascular prosthesis, failures may occur thereafter. It has been found that type I failures may affect up to 5-10% of all implanted prostheses. Accordingly, there is a clear need for an endovascular prosthesis which can reduce the likelihood of, and ideally eliminate, type I failures.

U.S. Pat. No. 7,044,962 to Elliott describes an implantable prosthesis with a radially-expandable tubular body and at least one skirt extending therefrom. The skirt in his invention terminates in a peripheral edge. At least portions of the peripheral edge are free and displaceable to a greater diameter of the tubular body. Thus, with the implantable prosthesis being a stent-graft used to treat an aortic aneurysm (e.g., AAA), the skirt may be used to inhibit type I endoleaks upon its selective displacement in response to irregular aortic shaping and/or aneurysm neck expansion. The skirt may actively inhibit type I endoleaks by forming a physical barrier against flow between the tubular body and the aortic wall. In addition, the skirt may passively inhibit endoleak formation by sufficiently restricting blood flow to allow coagulation and clot formation, which would act as a barrier against endoleakage.

U.S. Pat. No. 4,938,740 to Melbin describes a technique in which diseased portions of a blood vessel, such as with an aneurysm, are ablated and replaced with a prosthetic member. This technique, however, requires open surgery. As an improvement over this technique, endovascular emplacement techniques have been developed to implant grafts and stent-grafts into a vessel from a remote puncture site, thereby obviating the need for open surgery. For example, an endovascular prosthesis (stent or stent-graft) is positioned to bypass the aneurysm with the ends of the prosthesis being in contiguous contact with healthy portions of the aorta, the prosthesis having been introduced endovascularly (e.g., with a catheter). Accordingly, if the aneurysm were to rupture, blood flow through the aorta would be uninterrupted, and internal bleeding generally avoided.

PCT Publication WO 2008/107885 to Shalev et al., and US Patent Application Publication 2010/0063575 to Shalev et al. in the US national stage thereof, which are incorporated herein by reference, describe a multiple-component expandable endoluminal system for treating a lesion at a bifurcation, including a self expandable tubular root member having a side-looking engagement aperture, and a self expandable tubular trunk member comprising a substantially blood impervious polymeric liner secured therealong. Both have a radially-compressed state adapted for percutaneous intraluminal delivery and a radially-expanded state adapted for endoluminal support.

The following references may be of interest:
U.S. Pat. No. 5,824,040 to Cox et al.
US Patent Application Publication 2006/0229709 to Morris et al.
US Patent Application Publication 2006/0241740 to Vardi et al.
US Patent Application Publication 2008/0109066 to Quinn

SUMMARY OF APPLICATIONS

Some applications of the present invention provide an endovascular stent-graft, which comprises a structural member and a fluid flow guide. When the stent-graft assumes a radially-expanded state upon being deployed from a delivery catheter, the fluid flow guide is shaped so as to define radially-diverging and radially-converging portions, which together define a bulge that extends radially outward. When the stent-graft is deployed in an aneurysmatic abdominal aorta, the bulge extends radially outward against a rostral portion of the aortic aneurysm, thereby helping prevent a current or a future type I endoleak.

Typically, the stent-graft is configured such that the bulge expands radially as the rostral end of the aneurysm enlarges, in order to maintain a tight seal with the wall of the aorta, thereby preventing current or future type I endoleaks. At the same time, the stent-graft is configured to apply a radially-outward force that is sufficient to cause the bulge to expand with the aortic wall, but insufficient to itself cause expansion of the aortic wall. The crossing profile of the stent-graft when it assumes a radially-compressed state is less than the crossing profile would be if the bulge were instead provided by a separate skirt. Use of a separate skirt would necessitate additional, overlapping material of the fluid flow guide, and additional structural stent elements.

For some applications, a rostral-most first portion of the structural member defines a plurality of anchoring elements that extend radially outwardly, and, optionally, rostrally, when the stent-graft assumes the radially-expanded state. The anchoring elements anchor the stent-graft to the vascular wall, helping prevent dislodgement. A second portion of the structural member defines a stent body when the stent-graft assumes the radially-expanded state.

In some applications of the present invention, an endovascular stent-graft comprises a foldable skirt. The stent-graft comprises a structural member, a fluid flow guide, a rostrally-positioned foldable skirt. A rostral-most first portion of the structural member defines a plurality of anchoring elements that extend radially outwardly and rostrally when the stent-graft assumes the radially-expanded state. A second portion of the structural member defines a tubular body when the stent-graft assumes the radially-expanded state. The skirt extends from the structural member at a circumferential juncture between the anchoring elements and the tubular body, and terminates in a peripheral edge. The peripheral edge has a greater circumference than that of the circumferential juncture when the stent-graft assumes the radially-expanded state.

The skirt extends rostrally from the circumferential juncture, radially surrounding the anchoring elements, when the stent-graft is initially positioned in a delivery catheter, and retains this position initially upon being deployed from the catheter. This rostrally-extending position facilitates low-profile mounting of the endovascular stent-graft in the radially-compressed state within the delivery catheter. Upon application of a caudally-directed force to the peripheral edge of the skirt after deployment of the stent-graft from the delivery catheter, the skirt extends caudally from the circumferential juncture, in order to facilitate sealing of blood leakage around the stent-graft.

In some application of the present invention, an endovascular prosthesis comprises a structural member, which in part defines a stent body; a plurality of circumferentially disposed tissue engagement members; and a plurality of communicating members that respectively connect the structural member to the tissue engagement members. For some applications, the prosthesis further comprises a fluid flow guide. The tissue engagement members are disposed externally to the stent body when the prosthesis assumes the radially-expanded state. The communicating members are generally radially-oriented when the prosthesis assumes the radially-expanded state. Typically, the tissue engagement members are blunt. As a result, the tissue engagement members cause low trauma to the wall of the aorta, and typically do not pierce the wall. Typically, several weeks after placement of the prosthesis, the tissue engagement members become embedded in the wall of the aorta, thereby helping hold the prosthesis in place. Typically, each of the tissue engagement members extends in one or more directions generally parallel to a surface of the stent body.

For some applications, the tissue engagement members are generally circumferentially arcuate and extend laterally around the stent body. For other applications, the tissue engagement members are generally linear and extend axially along the stent body. For still other applications, the tissue engagement members are polygonal, e.g., diamond-shaped, similar to the shape of standard stent closed cells.

In some applications of the present invention, a doubly-flared endovascular stent-graft prosthesis comprises a structural member. When the prosthesis assumes a radially-expanded state, the structural member is shaped so as to define: (a) a flared rostral portion, which flares radially outward in a rostral direction, (b) a flared caudal portion, which flares radially outward in a caudal direction, and, optionally, (c) a generally constant-diameter body portion, which is disposed longitudinally between the flared rostral and caudal portions.

For some applications, a spring coefficient of the flared caudal portion is (a) at least 20% less than a spring coefficient of the body portion, and/or (b) at least 20% less than a spring coefficient of the flared rostral portion. The low spring coefficient helps the flared caudal portion to maintain a tight seal with the wall of the aorta, thereby preventing current or future type I endoleaks. At the same time, flared caudal portion is configured to apply a radially-outward force that is sufficient to expand with the aortic wall, but insufficient to itself cause expansion of the aortic wall.

For some applications, the prosthesis further comprises a stent-engagement member, which, when the prosthesis assumes the radially-expanded state, is generally tubular. The stent-engagement member is configured to be sealingly coupled to a primary stent-graft. The stent-engagement member is disposed at least partially within at least one portion selected from the group consisting of: the flared caudal portion, and the body portion. Typically, the prosthesis further comprises a biologically-compatible substantially fluid-impervious flexible sheet, which at least partially covers the stent-engagement member.

The prosthesis is typically transvascularly introduced into the aorta, and positioned such that the flared caudal portion is disposed in rostral end of an abdominal aortic aneurysm. The flare of the caudal portion seals the prosthesis to the rostral end of the aneurysm, thereby reducing a current or future risk for type I endoleak.

In some applications of the present invention, a self-expanding lumen-engagement prosthesis member, which is generally tubular when the prosthesis member assumes a radially-expanded state, comprises a plurality of support members distributed around a circumference of the prosthesis member. The support members are shaped so as to define respective curves having concavities that face radially outward. The prosthesis member further comprises a plurality of rostral barbs and a plurality of caudal barbs, disposed more caudally than the rostral barbs. When the prosthesis member assumes the radially-expanded state, the rostral barbs extend caudally and radially outwardly from respective ones of support members, and the caudal barbs extend rostrally and radially outward from respective ones of the support members. The rostral barbs are typically only slightly caudally oriented, and the caudal barbs are typically only slightly rostrally oriented. Typically, the rostral and caudal barbs are disposed at rostral and caudal ends of the support members, respectively.

The oppositely-oriented rostral and caudal barbs axially pinch tissue of the aorta between the barbs, thereby anchoring the prosthesis member to the aorta. The concavity of the support members generally increases the axial forces applied by the barbs. For some applications, the prosthesis member is configured to longitudinally shorten as the prosthesis member transitions from a radially-compressed state to the radially-expanded state, thereby bringing the rostral and caudal ends of the support members closer to each other, as an average diameter of the structural member increases. For some applications, the prosthesis member is mounted at a rostral end of an endovascular stent-graft.

In some applications of the present invention, a self-expandable endovascular sealing stent-graft comprises a structural member and a fluid flow guide, which is coupled to at least a portion of structural member. The structural member has a generally tubular shape, and is shaped so as to define at least two elongated indentations. Each of the elongated indentations extends rostrally to a rostral end of the structural member, and is tapered in a caudal direction until the indentation converges with the generally tubular shape of the structural member. The fluid flow guide covers at least a portion of each of the elongated indentations. The elongated indentations serve to direct blood flow toward the renal arteries. The structural member typically provides an outwardly-directed radial force against the aorta other than at the elongated indentations, which serves to anchor the stent-graft in the aorta and/or to push the fluid flow guide sealingly against the aorta, thereby preventing current or future type I endoleaks.

In some applications of the present invention, a unilumen endovascular stent-graft comprises rostral and caudal body portions, which comprise rostral and caudal structural members, respectively. The stent-graft also comprises a middle body portion, disposed longitudinally between the rostral and caudal body portions. The stent-graft further comprises a unilumen fluid flow guide. For some applications, the middle body portion comprises a middle structural member, which is integrally joined to the rostral and caudal structural members. Typically, at least a portion of the middle structural member is configured to be axially expandable. Alternatively, the middle body portion is not structurally supported. For some applications, when the stent-graft assumes the radially-expanded state, the caudal structural member is flared radially outward at a caudal end thereof.

The unilumen fluid flow guide defines a single, non-bifurcated lumen, so as to define a single fluid flow path through the stent-graft. The single lumen is configured to entirely span the abdominal aorta between the renal arteries and the aorto-iliac bifurcation, and not to substantially extend into the aorto-iliac bifurcation, i.e., to extend into the aorto-iliac bifurcation less than 1 cm, or not at all.

Typically, at least a portion of the middle portion of the fluid flow guide is axially expandable. For example, the portion may be pleated, e.g., accordion-pleated, or may comprise a longitudinally elastic material.

For some applications, when the stent-graft assumes the radially-expanded state, a rostral portion of the fluid flow guide that at least partially covers the rostral structural member is shaped so as to define rostral radially-diverging and radially-converging portions, which portions together define a rostral bulge that extends radially outward. When the stent-graft assumes the radially-expanded state, a caudal portion of the fluid flow guide that at least partially covers the caudal structural member is shaped so as to define caudal radially-diverging and radially-converging portions, which portions together define a caudal bulge that extends radially outward. The rostral and caudal bulges help to prevent a current or a future type I endoleak at a rostral end and a caudal end of an aortic aneurysm, respectively.

Typically, the stent-graft is configured such that the bulges expand radially as the rostral end and caudal end of the aneurysm enlarge, respectively, in order to maintain a tight seal with the wall of the aorta, thereby preventing current or future type I endoleaks. At the same time, the stent-graft is configured to apply a radially-outward force that is sufficient to cause the bulges to expand with the aortic wall, but insufficient to itself cause expansion of the aortic wall.

For some applications, a uni-iliac self-expandable extension stent is provided for use with the unilumen stent-graft. A rostral end of the uni-iliac extension stent is coupled to a caudal end of the caudal body portion of the stent-graft along a portion of a circumference of the caudal end. The uni-iliac extension stent is shaped such that a rostral portion thereof defines a lateral opening therethrough, defined by a discontinuity of stent cells along a portion of the circumference of the extension stent. After deployment of the stent-graft in the aorta and the uni-iliac stent in one of the iliac arteries, a bi-iliac stent is advanced through the iliac artery in which uni-iliac stent is positioned, passed through the opening, and then into the other iliac artery. The bi-iliac stent and uni-iliac stent help hold the stent-graft anchored in place. For some applications, a portion of the uni-iliac stent-graft caudal to the opening comprises a fluid flow guide, which may help treat an iliac aneurysm.

For some applications, the unilumen stent-graft further comprises a plurality of circumferentially-disposed, axially-oriented engagement members, coupled to a caudal end of the caudal structural member. The engagement members are configured to prevent down-migration of the stent-graft through the aorto-iliac bifurcation, which might obstruct the bifurcation.

For some applications, the unilumen stent-graft further comprises a self-expandable uni-iliac extension stent. A rostral end of the uni-iliac extension stent is coupled within the caudal body portion of the stent-graft, typically at or near a caudal end of the caudal bulge, such that the rostral end of the uni-iliac extension stent passes through the caudal end of the caudal body portion and into an interior of the caudal body portion. The uni-iliac extension stent may help anchor the stent-graft in place in the aorta, as well as treat an iliac aneurysm. The stent-graft and the iliac extension stent serve in combination as an aorto-uni-iliac stent-graft.

For some applications, a rostral portion of the uni-iliac extension stent is shaped so as to provide a lateral opening therethrough, defined by a discontinuity of stent cells along a portion of the circumference of the aorto-uni-iliac stent. After deployment of the stent-graft in the aorta and the uni-iliac extension stent in one of the iliac arteries, a bi-iliac stent is advanced through the iliac artery in which the uni-iliac stent is positioned, passed through the opening, and then into the other iliac artery. The bi-iliac stent and the aorto-uni-iliac stent help hold the stent-graft anchored in place. For some applications, a caudal portion of the uni-iliac extension stent comprises a fluid flow guide, which may help treat an iliac aneurysm.

For some applications, the unilumen stent-graft further comprises at least two (e.g., exactly two) iliac engagement members. The iliac engagement members are coupled to a caudal end of the caudal structural member, typically on opposites sides of the caudal end. A self-expandable bi-iliac stent is further provided. The bi-iliac stent is (a) advanced through one of the iliac arteries, (b) passed through the iliac engagement members, such that the engagement members and the bi-iliac stent-body engage each other (e.g., interlock with each other), and then (c) into the other iliac artery. The bi-iliac stent helps hold the stent-graft anchored in place.

There is therefore provided, in accordance with an application of the present invention, apparatus for use with a delivery catheter, the apparatus including an endovascular stent-graft, which is configured to initially be positioned in the delivery catheter in a radially-compressed state, and to assume a radially-expanded state upon being deployed from the delivery catheter, and which includes:

a structural member, which includes a plurality of structural stent elements, at least a portion of which structural stent elements define a stent body when the stent-graft assumes the radially-expanded state; and a fluid flow guide, which includes at least one biologically-compatible substantially fluid-impervious flexible sheet, and which is coupled to the stent body, wherein, when the stent-graft assumes the radially-expanded state, the fluid flow guide is shaped so as to define radially-diverging and radially-converging portions, which together define a bulge that extends radially outward, which bulge has a greatest cross-sectional area that is equal to at least 120% of a cross-sectional area of a narrowest portion of the stent-graft rostral to the bulge.

For some applications, the apparatus further includes the delivery catheter.

For some applications, a site on the bulge that has the greatest cross-section area is within 5 cm of a rostral end of the fluid flow guide, when the stent-graft assumes the radially-expanded state.

For some applications, the at least a portion of the structural stent elements is a first portion of the structural stent elements, and a rostral-most second portion of the structural stent elements define a plurality of anchoring elements that extend radially outwardly when the stent-graft assumes the radially-expanded state. For some applications, the structural member is configured such that the bulge applies a radially-outward force that is less than a radially-outward force applied by the anchoring elements, when the stent-graft assumes the radially-expanded state. For example, the radially-outward force applied by the bulge may be between 25% and 50% of the radially-outward force applied by the anchoring elements.

For some applications, a first subset of the structural stent elements of the stent body are configured to cause the fluid flow guide to define the bulge, when the stent-graft assumes the radially-expanded state. For some applications, (a) a second subset of the structural stent elements of the stent body are not configured to cause the fluid flow guide to define the bulge, when the stent-graft assumes the radially-expanded state, and (b) the structural stent elements of the first subset at least partially overlap the structural stent elements of the second subset lengthwise along the stent body. For some applications, the structural stent elements include a metal, and the structural stent elements of the first subset contact at least a portion of the structural stent elements of the second subset, when the stent-graft assumes the radially-compressed state.

For some applications, a spring coefficient of the first subset, measured during application of a radial force at a first point of the first subset that is furthest from a central longitudinal axis of the stent-graft, is at least 20% less than a spring coefficient of the second subset, measured at a second point of the second subset that is axially aligned with the first point.

For some applications, the structural stent elements of the second subset are shaped so as to define a substantially tubular structure, when the stent-graft assumes the radially-expanded state. For some applications, the substantially tubular structure is a constant diameter cylinder, when the stent-graft assumes the radially-expanded state. For some applications, the substantially tubular structure is a flared cylinder, when the stent-graft assumes the radially-expanded state.

For some applications, when the stent-graft assumes the radially-expanded state, the structural stent elements of the first subset are shaped so as to define a plurality of arms that extend radially outward, and are configured to cause the fluid flow guide to define the bulge. For some applications, the arms extend radially outward in a caudal direction, when the stent-graft assumes the radially-expanded state.

For some applications, the structural stent elements of the second subset define an internal structural lumen, and the structural stent elements of the first subset define an external structural lumen, which is disposed radially outward of the internal structural lumen when the stent-graft assumes the radially-expanded state.

For some applications, the first and second subsets are mutually exclusive. Alternatively, the first and second subsets share at least one of the structural stent elements. For some applications, the structural stent elements of the first subset are interconnected. Alternatively or additionally, the structural stent elements of the second subset are interconnected. For some applications, a third subset of the structural stent elements of the stent body connect the structural stent elements of the first subset with the structural stent elements of the second subset. For some applications, the structural stent elements of the third subset are substantially radially oriented, when the stent-graft assumes the radially-expanded state.

For some applications, the structural stent elements of the first subset are concentric with the structural stent elements of the second subset, when the stent-graft assumes the radially-expanded state.

For some applications, the structural stent elements of the first subset radially converge with the structural elements of the second subset at respective rostral ends of the first and second subsets. Alternatively or additionally, the structural stent elements of the first subset radially converge with the structural elements of the second subset at respective caudal ends of the first and second subsets.

For some applications, when the stent-graft assumes the radially-expanded state, the structural stent elements of the first subset are grouped into a plurality of axially-disposed arrays of the structural stent elements, each of the arrays generally circumscribing at least a 360-degree arc, each of the arrays being substantially morphologically deformable independently of the axially adjacent arrays. For some applications, at least a portion of the arrays are structurally connected to the axially adjacent arrays. For some applications, at least a portion of the arrays are not structurally connected to the axially adjacent arrays.

For some applications, a caudal end of the structural member and a caudal end of the fluid flow guide together define a single lumen, when the stent-graft assumes the radially-expanded state. Alternatively, a caudal end of the structural member and a caudal end of the fluid flow guide together define a bifurcated lumen, when the stent-graft assumes the radially-expanded state.

For some applications, the bulge is adapted to apply an axial force vector in a rostral direction.

For some applications, the structural member includes a self-expanding material. For some applications, the structural member includes a super-elastic alloy, such as Nitinol.

There is further provided, in accordance with an application of the present invention, apparatus including an endovascular stent-graft system, which includes:

an endovascular stent-graft delivery tool, which includes a delivery catheter; and an endovascular stent-graft, which is configured to initially be positioned in the delivery catheter in a radially-compressed state, and to assume a radially-expanded state upon being deployed from the delivery catheter, and which includes:

a structural member, which includes a plurality of structural stent elements, at least a portion of which structural stent elements define a stent body when the stent-graft assumes the radially-expanded state; and a fluid flow guide, which includes at least one biologically-compatible substantially fluid-impervious flexible sheet, and which is coupled to the stent body, wherein, when the stent-graft assumes the radially-expanded state, the fluid flow guide is shaped so as to define radially-diverging and radially-converging portions, which together define a bulge that extends radially outward, which has a greatest cross-sectional area that is equal to at least 120% of a cross-sectional area of a narrowest portion of the stent-graft rostral to the bulge.

There is still further provided, in accordance with an application of the present invention, a method including:

providing an endovascular stent-graft, which is configured to assume a radially-compressed state and a radially-expanded state, and which includes (a) a structural member, which includes a plurality of structural stent elements, at least a portion of which structural stent elements define a stent body when the stent-graft assumes the radially-expanded state, and (b) a fluid flow guide, which includes at least one biologically-compatible substantially fluid-impervious flexible sheet, and which is coupled to the stent body, wherein, when the stent-graft assumes the radially-expanded state, the fluid flow guide is shaped so as to define radially-diverging and radially-converging portions, which together define a bulge that extends radially outward, which has a greatest cross-sectional area that is equal to at least 120% of a cross-sectional area of a narrowest portion of the stent-graft rostral to the bulge;

transvascularly introducing the stent-graft into an aorta of a human subject, while the stent-graft is positioned in a delivery catheter in the radially-compressed state; and deploying the stent-graft from the delivery catheter at least partially in the aorta such that the bulge extends radially outward against and sealingly contacts a rostral portion of an abdominal aortic aneurysm in the aorta when the stent-graft assumes the radially-expanded state.

For some applications, the method further includes identifying the subject as suffering from the aortic aneurysm, and introducing includes transvascularly introducing the stent-graft responsively to the identifying.

For some applications, the endovascular stent-graft is one of two endovascular stent grafts, the structural member is one of two structural members, and the fluid flow guide is one of two fluid flow guides, the endovascular stent-grafts include the structural members and the fluid flow guides, respectively, and introducing and deploying includes introducing and deploying a first one of the stent-grafts, and further including:

transvascularly introducing a second one of the stent-grafts, while the second stent-graft is in the radially-compressed state, into the aorta, adjacent to an aorto-iliac bifurcation, such that the second stent-graft is oriented in an axial direction opposite to that of the first stent graft; and deploying the second stent-graft at least partially in the aorta such that the bulge of the second stent-graft extends radially outward against a caudal portion of the abdominal aortic aneurysm in the aorta when the second stent-graft assumes the radially-expanded state, and such that an end of one of the stent-grafts is deployed within an end of the other of the stent-grafts, in order to provide fluid-tight coupling of the stent-grafts with each other when the stent-grafts assume the radially-expanded state.

For some applications, the structural member of the second stent-graft is shaped so as to define a plurality of anchoring elements, and deploying the second stent-graft includes positioning the anchoring elements to engage an aorta-iliac bifurcation.

For some applications, a first subset of the structural stent elements of the stent body are configured to cause the fluid flow guide to define the bulge, when the stent-graft assumes the radially-expanded state.

There is additionally provided, in accordance with an application of the present invention, apparatus for use with a delivery catheter, the apparatus including an endovascular stent-graft, which is configured to initially be positioned in the delivery catheter in a radially-compressed state, and to assume a radially-expanded state upon being deployed from the delivery catheter, and which includes:

a structural member, which includes a plurality of structural stent elements, a rostral-most first portion of which members define a plurality of anchoring elements that extend radially outwardly and rostrally when the stent-graft assumes the radially-expanded state, and a second portion of which members define a tubular body when the stent-graft assumes the radially-expanded state;

a fluid flow guide, which includes at least one biologically-compatible substantially fluid-impervious flexible sheet, and which is coupled to the tubular body; and at least one skirt, which includes at least one biologically-compatible substantially fluid-impervious flexible sheet, and which extends from the structural member at a circumferential juncture between the anchoring elements and the tubular body, and which terminates in a peripheral edge that has a greater circumference than that of the circumferential juncture when the stent-graft assumes the radially-expanded state, wherein the skirt extends rostrally from the juncture when the stent-graft is initially positioned in the delivery catheter in the radially-compressed state, and wherein, upon application of a caudally-directed force to the peripheral edge of the skirt after deployment of the stent-graft from the delivery catheter, the skirt extends caudally from the juncture.

For some applications, the apparatus further includes the delivery catheter.

For some applications, the circumference of the peripheral edge of the skirt is greater than a circumference of all other elements of the stent-graft, when the stent-graft assumes the radially-expanded state.

For some applications, the skirt is sealingly coupled to a rostral end of the fluid flow guide around the entire circumferential juncture.

For some applications, the skirt further includes a scaffold, which at least partially supports the flexible sheet. For some applications, the scaffold extends from at least a portion of the juncture to at least a portion of the peripheral edge of the skirt. For some applications, the juncture includes a pivot, to which the scaffold is rotatably coupled so as to allow the skirt to transition from extending rostrally to extending caudally. For some applications, the scaffold includes a self-expanding material. For some applications, the scaffold includes a super-elastic alloy, such as Nitinol.

There is yet additionally provided, in accordance with an application of the present invention, apparatus including an endovascular stent-graft system, which includes:

an endovascular stent-graft delivery tool, which includes a delivery catheter; and an endovascular stent-graft, which is configured to initially be positioned in the delivery catheter in a radially-compressed state, and to assume a radially-expanded state upon being deployed from the delivery catheter, and which includes:

a structural member, which includes a plurality of structural stent elements, a rostral-most first portion of which members define a plurality of anchoring elements that extend radially outwardly and rostrally when the stent-graft assumes the radially-expanded state, and a second portion of which members define a tubular body when the stent-graft assumes the radially-expanded state;

a fluid flow guide, which includes at least one biologically-compatible substantially fluid-impervious flexible sheet, and which is coupled to the tubular body; and at least one skirt, which includes at least one biologically-compatible substantially fluid-impervious flexible sheet, and which extends from the structural member at a circumferential juncture between the anchoring elements and the tubular body, and which terminates in a peripheral edge that has a greater circumference than that of the circumferential juncture when the stent-graft assumes the radially-expanded state, wherein the skirt extends rostrally from the juncture when the stent-graft is initially positioned in the delivery catheter in the radially-compressed state, and wherein, upon application of a caudally-directed force to the peripheral edge of the skirt after deployment of the stent-graft from the delivery catheter, the skirt extends caudally from the juncture.

There is also provided, in accordance with an application of the present invention, a method including:

providing an endovascular stent-graft, which is configured to assume a radially-compressed state and a radially-expanded state, and which includes (a) a structural member, which includes a plurality of structural stent elements, a first rostral-most portion of which members define a plurality of anchoring elements, and a second portion of which members define a tubular body when the stent-graft assumes the radially-expanded state, (b) a fluid flow guide, which includes at least one biologically-compatible substantially fluid-impervious flexible sheet, and which is coupled to the tubular body, and (c) at least one skirt, which includes at least one biologically-compatible substantially fluid-impervious flexible sheet, and which extends from the structural member at a circumferential juncture between the anchoring elements and the tubular body, and which terminates in a peripheral edge that has a greater circumference than that of the circumferential juncture when the stent-graft assumes the radially-expanded state;

transvascularly introducing the stent-graft into an aorta of a human subject, while the stent-graft is positioned in a delivery catheter in the radially-compressed state such that the skirt extends rostrally from the juncture;

at least partially deploying the stent-graft from the delivery catheter in the aorta such that the skirt at least partially radially expands, thereby bringing the peripheral edge of the skirt into contact with a wall of the aorta caudal to renal arteries of the subject, and such that the anchoring elements extend radially outwardly and rostrally; and inverting the skirt such that the skirt extends caudally from the juncture, by applying a caudally-directed force to the peripheral edge of the skirt after at least partially deploying the stent-graft from the delivery catheter, in order to facilitate sealing of blood leakage around the stent-graft when it assumes the radially-expanded state.

For some applications, the method further includes identifying the subject as suffering from an aortic aneurysm, and introducing includes transvascularly introducing the stent-graft responsively to the identifying.

For some applications, applying the caudally-directed force includes advancing the stent-graft rostrally such that a wall of the aorta applies the caudally-directed force to the peripheral edge of the skirt.

For some applications, the skirt further includes a scaffold, which at least partially supports the flexible sheet, and the juncture includes a pivot, to which the scaffold is rotatably coupled, and inverting the skirt includes rotating the skirt around on the pivot to transition the skirt from extending rostrally to extending caudally.

There is further provided, in accordance with an application of the present invention, apparatus for use with a delivery catheter and a primary stent-graft, the apparatus including a doubly-flared endovascular stent-graft, which is configured to initially be positioned in the delivery catheter in a radially-compressed state, and to assume a radially-expanded state upon being deployed from the delivery catheter, and which includes:

a structural member, which includes a plurality of structural stent elements, and which, when the doubly-flared endovascular stent-graft assumes the radially-expanded state, is shaped so as to define (a) a flared rostral portion, which flares radially outward in a rostral direction, and (b) a flared caudal portion, which flares radially outward in a caudal direction;

at least one biologically-compatible substantially fluid-impervious flexible sheet, which is coupled to at least the flared caudal portion; and a stent-engagement member, which is generally tubular when the doubly-flared endovascular stent-graft assumes the radially-expanded state, which is disposed at least partially within the flared caudal portion, and which is configured to be sealingly coupled to the primary stent-graft.

For some applications, the apparatus further includes the primary stent-graft.

For some applications, the apparatus further includes the delivery catheter.

For some applications, the structural member, when the doubly-flared endovascular stent-graft assumes the radially-expanded state, is shaped so as to further define a body portion, disposed longitudinally between the flared rostral and caudal portions, and having a diameter that varies by less than 15% along an entire length of the body portion.

For some applications, a spring coefficient of the flared caudal portion, measured during application of a radial force at a first point on the flared caudal portion that is furthest from a central longitudinal axis of the doubly-flared endovascular stent-graft, is at least 20% less than at least one spring coefficient selected from the group consisting of: (a) a spring coefficient of the body portion, measured during application of the radial force at a second point on the body portion that is furthest from the axis, and (b) a spring coefficient of the flared rostral portion, measured during application of the radial force at a third point on the flared rostral portion that is furthest from the axis.

For some applications, the flared rostral portion defines a plurality of anchoring elements that extend radially outwardly, when the doubly-flared endovascular stent-graft assumes the radially-expanded state.

For some applications, the at least one flexible sheet of the fluid flow guide is a first at least flexible sheet, and the doubly-flared endovascular stent-graft further includes at least a second biologically-compatible substantially fluid-impervious flexible sheet, which at least partially covers the stent-engagement member.

For some applications, the stent engagement member includes a scaffold. For some applications, the scaffold includes a self-expanding material. For some applications, the scaffold includes a super-elastic alloy, such as Nitinol.

For some applications, an axial length of the flared caudal portion varies around a circumference of the flared caudal portion.

For some applications, the caudal end of the structural member is internally curved.

For some applications, the flared caudal portion is externally convex.

For some applications, the flared caudal portion includes a rostral sub-portion that is externally concave and a more caudal sub-portion that is externally convex.

For some applications, the structural member includes a self-expanding material. For some applications, the structural member includes a super-elastic alloy, such as Nitinol. For some applications, the structural member is woven. For some applications, the structural member is braided.

There is still further provided, in accordance with an application of the present invention, a method including:

providing a doubly-flared endovascular stent-graft, which is configured to assume a radially-compressed state and a radially-expanded state, and which includes (i) a structural member, which includes a plurality of structural stent elements, and which, when the doubly-flared endovascular stent-graft assumes the radially-expanded state, is shaped so as to define (a) a flared rostral portion, which flares radially outward in a rostral direction, and (b) a flared caudal portion, which flares radially outward in a caudal direction, and (ii) a fluid flow guide, which includes at least one biologically-compatible substantially fluid-impervious flexible sheet, and which is coupled to at least the flared caudal portion;

transvascularly introducing the doubly-flared endovascular stent-graft into an aorta of a human subject, while the doubly-flared endovascular stent-graft is positioned in a delivery catheter in the radially-compressed state; and transitioning the doubly-flared endovascular stent-graft to the radially-expanded state by deploying the doubly-flared endovascular stent-graft from the delivery catheter in the aorta, such that the flared caudal portion is positioned caudal to both of anastomoses of renal arteries, and the flared rostral portion is positioned rostral to both of the anastomoses of the renal arteries.

For some applications, the method further includes identifying the subject as suffering from an aortic aneurysm, and introducing includes transvascularly introducing the doubly-flared endovascular stent-graft responsively to the identifying.

For some applications, the structural member, when the doubly-flared endovascular stent-graft assumes the radially-expanded state, is shaped so as to further define a body portion, disposed longitudinally between the flared rostral and caudal portions, and having a diameter that varies by less than 15% along an entire length thereof, and deploying includes deploying the doubly-flared endovascular stent-graft such that the body portion spans both the anastomoses of the renal arteries.

For some applications, providing the doubly-flared endovascular stent-graft includes providing the doubly-flared endovascular stent-graft having a diameter of the body portion that is at least 15% less than a diameter of the aorta between the renal arteries, and having a diameter of a caudal end of the structural member that is at least 20% larger than a diameter of the aorta immediately caudal to a more caudal one of the renal arteries.

For some applications, the doubly-flared endovascular further includes a stent-engagement member, which is generally tubular when the doubly-flared endovascular stent-graft assumes the radially-expanded state, and which is disposed at least partially within the flared caudal portion, and further including transvascularly delivering a primary stent-graft to the aorta, and sealingly coupling the primary stent-graft to the stent-engagement member.

For some applications, the method further includes:

providing an additional endovascular stent-graft that has a single-lumen rostral end and a bifurcated caudal end;

transvascularly introducing the single-lumen rostral end of the additional stent-graft into the aorta, and sealingly coupling the rostral end to a lumen defined by the fluid flow guide;

deploying the bifurcated caudal end of the additional stent-graft into both iliac arteries.

There is additionally provided, in accordance with an application of the present invention, apparatus including a self-expanding lumen-engagement prosthesis member, which is adjustable between a radially-expanded state and a radially-compressed state, which is generally tubular, and which includes:

a plurality of support members, which, when the prosthesis member assumes the radially-expanded state, are distributed around a circumference of the prosthesis member, and are shaped so as to define respective curves having concavities that face radially outward;

a plurality of rostral barbs, which extend caudally and radially outwardly from respective ones of the support members when the prosthesis member assumes the radially-expanded state; and a plurality of caudal barbs, which extend rostrally and radially outward from respective ones of the support members when the prosthesis member assumes the radially-expanded state, and which are disposed more caudally than the rostral barbs.

For some applications, the rostral barbs are disposed at respective rostral ends of the support members.

For some applications, the caudal barbs are disposed at respective caudal ends of the support members.

For some applications, the rostral barbs extend caudally at an angle of between 50 and 70 degrees with respect to a central longitudinal axis of the prosthesis member.

For some applications, the caudal barbs extend rostrally at an angle of between 50 and 70 degrees with respect to a central longitudinal axis of the prosthesis member.

For some applications, the apparatus further includes a stent-graft, a rostral end of which is coupled to a caudal end of the prosthesis member. For some applications, the stent-graft includes a fluid flow guide, which includes at least one biologically-compatible substantially fluid-impervious flexible sheet.

For some applications, the prosthesis member includes a self-expanding material. For some applications, the prosthesis member includes a super-elastic alloy, such as Nitinol. For some applications, the prosthesis member includes a braided material. For some applications, the prosthesis member includes a woven material.

For some applications, the prosthesis member is configured to longitudinally shorten as the prosthesis member transitions from the radially-compressed state to the radially-expanded state, thereby bringing the rostral and caudal ends of the structural member closer to each other.

For some applications, the apparatus further includes an endovascular stent-graft system, configured to endoluminally treat an aortic aneurysm, the system including the lumen-engagement prosthesis member.

There is yet additionally provided, in accordance with an application of the present invention, a method including:

providing a lumen-engagement prosthesis member, which is adjustable between a radially-expanded state and a radially-compressed state, and which includes (a) a structural member, which has rostral and caudal ends and a central longitudinal axis, and which is generally tubular and externally concave when the prosthesis member assumes the radially-expanded state, (b) a plurality of rostral barbs, which extend caudally and radially outwardly from the central longitudinal axis when the prosthesis member assumes the radially-expanded state, and (c) a plurality of caudal barbs, which extend rostrally and radially outward from the central longitudinal axis when the prosthesis member assumes the radially-expanded state;

transvascularly introducing the prosthesis member into an aorta of a human subject, while the prosthesis member is positioned in a delivery catheter in the radially-compressed state; and transitioning the prosthesis member to the radially-expanded state by deploying the prosthesis member from the delivery catheter in the aorta within 2 cm of renal arteries of the subject, such that the prosthesis member engages a wall of the aorta.

For some applications, the method further includes identifying the subject as suffering from an aortic aneurysm, and introducing includes transvascularly introducing the prosthesis member responsively to the identifying.

For some applications, deploying includes deploying the prosthesis member such that the prosthesis member engages the aortic wall rostral to the renal arteries.

For some applications, deploying includes deploying the prosthesis member such that the prosthesis member engages the aortic wall caudal to the renal arteries.

For some applications, providing the prosthesis member includes providing the prosthesis member sized such that a diameter of the structural member when the prosthesis member assumes the radially-expanded state is greater than a diameter of the aorta at sites at which the prosthetic member engages the aortic wall.

For some applications, transitioning the prosthesis includes causing the prosthesis member to longitudinally shorten as the prosthesis member transitions from the radially-compressed state to the radially-expanded state, thereby bringing the rostral and caudal ends of the structural member closer to each other.

There is also provided, in accordance with an application of the present invention, apparatus for use with a delivery catheter, the apparatus including an endovascular sealing stent-graft, which is configured to initially be positioned in the delivery catheter in a radially-compressed state, and to assume a radially-expanded state upon being deployed from the delivery catheter, and which includes:

a structural member, which includes a plurality of structural stent elements, and which, when the stent-graft assumes the radially-expanded state, has a generally tubular shape, and is shaped so as to define at least two elongated indentations, each of which extends rostrally to a rostral end of the structural member, and is tapered in a caudal direction until the indentation converges with the generally tubular shape of the structural member, and each of which has an axial length of at least 2 cm; and a fluid flow guide, which includes at least one biologically-compatible substantially fluid-impervious flexible sheet, and which is coupled to at least a portion of the structural member, and covers at least a portion of each of the elongated indentations.

For some applications, the apparatus further includes the delivery catheter.

For some applications, a rostral end of the fluid flow guide is disposed within 4 cm of the rostral end of the structural member.

For some applications, a caudal end of the fluid flow guide is disposed within 2 cm of a caudal end of the structural member.

For some applications, the stent-graft further includes a plurality of anchoring elements, which are generally radially oriented when the stent-graft assumes the radially-expanded state.

For some applications, a rostral end of each of the elongated indentations spans an arc of between 10 and 40 degrees.

For some applications, centers of two of the elongated indentations are offset by an angle of between 70 and 220 degrees, as measured with respect to a central longitudinal axis of the structural member. For some applications, the angle is between 150 and 170 degrees.

For some applications, a diameter of the structural member is between 2.5 and 3 cm, when the stent-graft assumes the radially-expanded state.

For some applications, an axial length of the structural member is between 4 and 7 cm, when the stent-graft assumes the radially-expanded state.

For some applications, the axial length of each of the elongated indentations no more than 4 cm, when the stent-graft assumes the radially-expanded state.

For some applications, a rostral end of each of the elongated indentations is indented between 0.5 and 1 cm from the generally tubular shape of the structural member, when the stent-graft assumes the radially-expanded state.

For some applications, the structural member includes a self-expanding material. For some applications, the structural member includes a super-elastic alloy, such as Nitinol.

There further provided, in accordance with an application of the present invention, a method including:

providing an endovascular sealing stent-graft, which is configured to assume a radially-compressed state and a radially-expanded state, and which includes (a) a structural member, which includes a plurality of structural stent elements, and which, when the stent-graft assumes the radially-expanded state, has a generally tubular shape, and is shaped so as to define at least two elongated indentations, each of which extends rostrally to a rostral end of the structural member, and is tapered in a caudal direction until the indentation converges with the generally tubular shape of the structural member, and each of which has an axial length of at least 2 cm, and (b) a fluid flow guide, which includes at least one biologically-compatible substantially fluid-impervious flexible sheet, and which is coupled to at least a portion of the structural member, and covers at least a portion of the elongated indentations;

transvascularly introducing the stent-graft into an aorta of a human subject, in a vicinity of renal arteries of the subject, while the stent-graft is positioned in a delivery catheter in the radially-compressed state;

transitioning the stent-graft to the radially-expanded state by deploying the stent-graft from the delivery catheter in the aorta, such that two of the elongated indentations are radially aligned with the renal arteries, with rostral ends of the elongated indentations rostral to the renal arteries, respectively, and caudal ends of the elongated indentations caudal to the renal arteries, respectively.

For some applications, the method further includes identifying the subject as suffering from an aortic aneurysm, and introducing includes transvascularly introducing the stent-graft responsively to the identifying.

For some applications, the stent-graft is one of a plurality of stent-grafts having different, respective angles of offset between two of the elongated indentations, and providing the stent-graft includes: assessing an angle between the renal arteries; and selecting one of the stent-grafts having an angle of offset closest to the assessed angle between the renal arteries.

There is still further provided, in accordance with an application of the present invention, apparatus for use with a delivery catheter, the apparatus including an endovascular prosthesis, which is configured to initially be positioned in the delivery catheter in a radially-compressed state, and to assume a radially-expanded state upon being deployed from the delivery catheter, and which includes:

a structural member, which includes a plurality of structural stent elements, at least a portion of which structural stent elements define a stent body when the prosthesis assumes the radially-expanded state;

a plurality of blunt tissue engagement members, which are disposed externally to the stent body when the prosthesis assumes the radially-expanded state; and a plurality of communicating members, which respectively connect the tissue engagement members to the stent body, the communicating members being generally radially-oriented when the prosthesis assumes the radially-expanded state.

For some applications, the apparatus further includes the delivery catheter.

For some applications, the endovascular prosthesis further includes a fluid flow guide, which includes at least one biologically-compatible substantially fluid-impervious flexible sheet, and which is coupled to the stent body.

For some applications, each of at least a portion of the tissue engagement members has surface area of at least 0.5 mm2.

For some applications, each of at least a portion of the tissue engagement members extends in one or more directions generally parallel to a surface of the stent body.

For some applications, respective distances between a surface of the stent body and all locations of each of at least a portion of the tissue engagement member vary by less than 30%.

For some applications, the tissue engagement members are arranged as a circumferential array around the stent body.

For some applications, the tissue engagement members are arranged as an axial array along the stent body.

For some applications, the apparatus further includes a plurality of connecting elements, which couple at least a portion of the tissue engagement members to respective adjacent ones of the tissue engagement members.

For some applications, when the prosthesis assumes the radially-expanded state, a spring coefficient of each of the communicating members, measuring during application of a radial force, is at least 20% less than a spring coefficient of the stent body, measured during application of the radial force at a point on the stent body at which the communicating member is connected.

For some applications, the tissue engagement members radially protrude a distance of between 1 and 4 mm from the stent body, when the prosthesis assumes the radially-expanded state.

For some applications, the at least a portion of the structural stent elements is a first portion of the structural stent elements, and a rostral-most second portion of the structural stent elements define a plurality of anchoring elements that extend radially outwardly when the prosthesis assumes the radially-expanded state.

For some applications, the tissue engagement members are arcuate, and extend laterally around the stent body. For some applications, the tissue engagement members are generally linear, and extend axially along the stent body. For some applications, the tissue engagement members are polygonal.

For some applications, the structural member includes a self-expanding material. For some applications, the structural member includes a super-elastic alloy, such as Nitinol.

There is additionally provided, in accordance with an application of the present invention, apparatus including an endovascular prosthetic system, which includes:

an endovascular prosthesis delivery tool, which includes a delivery catheter; and an endovascular prosthesis, which is configured to initially be positioned in the delivery catheter in a radially-compressed state, and to assume a radially-expanded state upon being deployed from the delivery catheter, and which includes:

a structural member, which includes a plurality of structural stent elements, at least a portion of which structural stent elements define a stent body when the prosthesis assumes the radially-expanded state;

a plurality of non-barbed tissue engagement members, which are disposed externally to the stent body when the prosthesis assumes the radially-expanded state; and a plurality of communicating members, which respectively connect the tissue engagement members to the stent body, the communicating members being generally radially-oriented when the prosthesis assumes the radially-expanded state.

There is yet additionally provided, in accordance with an application of the present invention, a method including:

providing an endovascular prosthesis, which is configured to assume a radially-compressed state and a radially-expanded state, and which includes (a) a structural member, which includes a plurality of structural stent elements, at least a portion of which structural stent elements define a stent body when the prosthesis assumes the radially-expanded state, (b) a plurality of non-barbed tissue engagement members, which are disposed externally to the stent body when the prosthesis assumes the radially-expanded state, and (c) a plurality of communicating members, which respectively connect the tissue engagement members to the stent body, the communicating members being generally radially-oriented when the prosthesis assumes the radially-expanded state;

transvascularly introducing the prosthesis into an aorta of a human subject, while the prosthesis is positioned in a delivery catheter in the radially-compressed state; and at least partially deploying the prosthesis from the delivery catheter in the aorta such that the tissue engagement members enter a wall of the aorta.

For some applications, the method further includes identifying the subject as suffering from an aortic aneurysm, and introducing includes transvascularly introducing the prosthesis responsively to the identifying.

For some applications, deploying includes at least partially deploying the prosthesis such that the tissue engagement members do not pass entirely through the aortic wall.

For some applications, providing the prosthesis including providing the prosthesis in which each of at least a portion of the tissue engagement members extends in one or more directions generally parallel to a surface of the stent body.

For some applications, providing the prosthesis including providing the prosthesis in which the tissue engagement members are arranged as a circumferential array around the stent body.

For some applications, providing the prosthesis including providing the prosthesis in which the tissue engagement members are arranged as an axial array along the stent body.

For some applications, providing the prosthesis including providing the prosthesis in which the tissue engagement members are arcuate, and extend laterally around the stent body.

For some applications, providing the prosthesis including providing the prosthesis in which the tissue engagement members are generally linear, and extend axially along the stent body.

For some applications, providing the prosthesis including providing the prosthesis in which the tissue engagement members are polygonal.

There is yet additionally provided, in accordance with an application of the present invention, apparatus for use with a delivery catheter, the apparatus including an endovascular stent-graft, which is configured to initially be positioned in the delivery catheter in a radially-compressed state, and to assume a radially-expanded state upon being deployed from the delivery catheter, and which includes:

rostral and caudal body portions, which include rostral and caudal structural members, respectively, each of which includes a plurality of structural stent elements;

a middle body portion, disposed longitudinally between the rostral and caudal body portions; and a unilumen fluid flow guide, which includes at least one biologically-compatible substantially fluid-impervious flexible sheet shaped so as to define a single, non-bifurcated lumen, and which is coupled to the rostral and caudal structural members, at least partially covers the rostral structural member, at least partially covers the caudal structural member, and includes a middle portion that extends longitudinally along an entire length of the middle body portion, wherein, when the stent-graft assumes the radially-expanded state, a rostral portion of the fluid flow guide that at least partially covers the rostral structural member is shaped so as to define rostral radially-diverging and radially-converging portions, which portions together define a rostral bulge that extends radially outward, which bulge has a greatest cross-sectional area that is equal to at least 120% of a cross-sectional area of a narrowest portion of the rostral body portion rostral to the bulge, and wherein, when the stent-graft assumes the radially-expanded state, a caudal portion of the fluid flow guide that at least partially covers the caudal structural member is shaped so as to define caudal radially-diverging and radially-converging portions, which portions together define a caudal bulge that extends radially outward, which bulge has a greatest cross-sectional area that is equal to at least 120% of a cross-sectional area of a narrowest portion of the caudal body portion caudal to the bulge.

For some applications, the rostral structural member is shaped so as to define a generally cylindrical subportion rostral to the rostral bulge, when the stent-graft assumes the radially-expanded state. For some applications, the rostral structural member is shaped so as to define a generally cylindrical subportion caudal to the rostral bulge, when the stent-graft assumes the radially-expanded state.

For some applications, a spring coefficient of the rostral bulge, measured during application of a radial force at a first point of the rostral bulge that is furthest from a central longitudinal axis of the stent-graft, is at least 20% less than a spring coefficient of the generally cylindrical subportion, measuring during application of the radial force at a second point of the generally cylindrical subportion that is furthest from the axis.

For some applications, the caudal structural member is shaped so as to define a generally cylindrical subportion caudal to the caudal bulge, when the stent-graft assumes the radially-expanded state.

For some applications, the caudal structural member is shaped so as to define a generally cylindrical subportion rostral to the caudal bulge, when the stent-graft assumes the radially-expanded state.

For some applications, a spring coefficient of the caudal bulge, measured during application of a radial force at a first point of the caudal bulge that is furthest from a central longitudinal axis of the stent-graft, is at least 20% less than a spring coefficient of the generally cylindrical subportion, measuring during application of the radial force at a second point of the generally cylindrical subportion that is furthest from the axis.

For some applications, the middle body portion includes a middle structural member, which includes a plurality of structural stent elements, and which is integrally joined to the rostral and caudal structural members.

For some applications, at least a portion of the middle structural member is configured to be axially expandable.

For some applications, the fluid flow guide is sparsely attached to the middle structural member.

For some applications, the middle body portion is not structurally supported by any structural stent elements.

For some applications, at least a portion of the middle portion of the fluid flow guide is axially expandable. For some applications, at least a portion of the middle portion of the fluid flow guide is kink-resistant.

For some applications, the middle portion of the fluid flow guide is generally cylindrical, when the stent-graft assumes the radially-expanded state.

For some applications, the apparatus further includes the delivery catheter.

For some applications, the caudal structural member is flared radially outward at a caudal end thereof, when the stent-graft assumes the radially-expanded state. For some applications, the caudal body portion further includes a first set of circumferentially-disposed barbs that extend radially outwardly and caudally when the stent-graft assumes the radially-expanded state, and the caudal end of the caudal structural member includes a second set of barbs that extend radially outward and rostrally when the stent-graft assumes the radially-expanded state. For some applications, a caudal end of the caudal structural member has a shape selected from the group consisting of: a non-circular ellipse, and a peanut shell shape.

For some applications, stent-graft further includes a plurality of anchoring elements that extend radially outwardly when the stent-graft assumes the radially-expanded state, the anchoring elements disposed rostral to the rostral body portion. For some applications, the rostral body portion is configured such that the rostral bulge applies a radially-outward force that is less than a radially-outward force applied by the anchoring elements, when the stent-graft assumes the radially-expanded state. For some applications, the rostral body portion further includes a first set of circumferentially-disposed barbs that extend radially outwardly and rostrally when the stent-graft assumes the radially-expanded state, and the anchoring elements include a second set of barbs that extend radially outwardly and caudally when the stent-graft assumes the radially-expanded state.

For some applications, a portion of the rostral structural stent elements are configured to cause the fluid flow guide to define the rostral bulge, when the stent-graft assumes the radially-expanded state, and a portion of the caudal structural stent elements are configured to cause the fluid flow guide to define the caudal bulge, when the stent-graft assumes the radially-expanded state.

For some applications, the apparatus further includes an expandable uni-iliac extension stent, a rostral end of which is coupled to a caudal end of the caudal body portion along a portion of a circumference of the caudal end. For some applications, the portion of the circumference is less than 40 degrees of the circumference. For some applications, the apparatus further includes at least one radiopaque marker, disposed on at least one stent selected from the group consisting of: the endovascular stent-graft, and the uni-iliac extension stent, and adapted to aid in achieving a desired rotational orientation of the stent-graft and the uni-iliac extension stent. For some applications, the apparatus further includes the delivery catheter. For some applications, the delivery catheter includes at least one radiopaque marker, adapted to aid in achieving a desired rotational orientation of the stent-graft and the uni-iliac extension stent. For some applications, the apparatus further includes an expandable bi-iliac extension stent, which is configured to be passed through a rostral portion of the uni-iliac extension stent. For some applications, the bi-iliac stent includes a super-elastic alloy, such as Nitinol. For some applications, the bi-iliac extension stent includes an extension fluid flow guide, which includes at least one biologically-compatible substantially fluid-impervious flexible sheet, and covers at least a portion of the bi-iliac extension stent. For some applications, the uni-iliac extension stent includes an extension fluid flow guide, which includes at least one biologically-compatible substantially fluid-impervious flexible sheet, and covers at least a portion of the uni-iliac extension stent. For some applications, the uni-iliac extension stent includes a super-elastic alloy, such as Nitinol.

For some applications, the structural members include a super-elastic alloy, such as Nitinol.

For some applications, the apparatus further includes a plurality of circumferentially-disposed, axially-oriented engagement members, coupled to a caudal end of the caudal structural member. For some applications, the apparatus further includes a self-expandable bi-iliac stent, which includes a bi-iliac stent body, and (a) at least a portion of the circumferentially-disposed, axially-oriented engagement members and (b) the bi-iliac stent body are configured to engage each other. For some applications, the bi-iliac stent further includes a fluid flow guide, which includes at least one biologically-compatible substantially fluid-impervious flexible sheet, and which is coupled to the bi-iliac stent body.

For some applications, the apparatus further includes an uni-iliac extension stent, a rostral end of which is coupled within the caudal body portion, such that the rostral end passes through a caudal end of the caudal body portion. For some applications, the uni-iliac extension stent includes a plurality of stent cells, and a rostral portion of the extension stent is shaped so as to provide a lateral opening therethrough, defined by a discontinuity of the stent cells along a portion of a circumference of the extension stent. For some applications, the portion of the circumference includes more than 320 degrees of the circumference.

For some applications, the stent-graft further includes at least two iliac engagement members, which are coupled to a caudal end of the caudal structural member, and the apparatus further includes a self-expandable bi-iliac stent, which is sized and shaped to be endovascularly introduced and subsequently deployed through iliac engagement members, so as to be coupled to the endovascular stent-graft.

There is also provided, in accordance with an application of the present invention, apparatus for use with a delivery catheter, the apparatus including an endovascular stent-graft, which is configured to initially be positioned in the delivery catheter in a radially-compressed state, and to assume a radially-expanded state upon being deployed from the delivery catheter, and which includes:

rostral and caudal body portions, which include rostral and caudal structural members, respectively, each of which includes a plurality of structural stent elements;

a middle body portion, disposed longitudinally between the rostral and caudal body portions; and a unilumen fluid flow guide, which includes at least one biologically-compatible substantially fluid-impervious flexible sheet shaped so as to define a single, non-bifurcated lumen, and which is coupled to the rostral and caudal structural members, at least partially covers the rostral structural member, at least partially covers the caudal structural member, and includes a middle portion that extends longitudinally along an entire length of the middle body portion, wherein at least a portion of the middle portion of the fluid flow guide is axially expandable.

For some applications, the stent-graft is configured such that an axial length of the stent-graft between a rostral end of the rostral body portion and a caudal end of the caudal body portion is variable between a minimum length and a maximum length, the minimum length between 2 and 5 cm, and the maximum length between 10 and 20 cm.

For some applications, the stent-graft is configured such that an axial length of the axially-expandable portion of the middle portion is variable up to a maximum length change, which maximum length change is between 2 and 20 cm.

For some applications, the stent-graft is configured such that the flow guide, at the rostral body portion, forms a seal with a wall of the aorta caudal to the renal arteries, and, at the caudal body portion, forms a seal with the aortic wall rostral to the iliac arteries.

For some applications, the middle body portion includes a middle structural member, which includes a plurality of structural stent elements, and which is integrally joined to the rostral and caudal structural members.

For some applications, the middle structural member is configured to be axially expandable.

For some applications, the middle body portion does not include any structural stent elements.

For some applications, the apparatus further includes the delivery catheter.

For some applications, stent-graft further includes a plurality of anchoring elements that extend radially outwardly when the stent-graft assumes the radially-expanded state, the anchoring elements disposed rostral to the rostral body portion.

For some applications, the stent-graft further includes a plurality of anchoring elements that extend radially outwardly when the stent-graft assumes the radially-expanded state, the anchoring elements disposed caudal to the caudal body portion.

There is further provided, in accordance with an application of the present invention, a method including:

providing an endovascular stent-graft, which is configured to assume a radially-compressed state and a radially-expanded state, and which includes (a) rostral and caudal body portions, which include rostral and caudal structural members, respectively, each of which includes a plurality of structural stent elements, (b) a middle body portion, disposed longitudinally between the rostral and caudal body portions, and (c) a unilumen fluid flow guide, which includes at least one biologically-compatible substantially fluid-impervious flexible sheet shaped so as to define a single, non-bifurcated lumen, and which is coupled to the rostral and caudal structural members, at least partially covers the rostral structural member, at least partially covers the caudal structural member, and includes a middle portion that extends longitudinally along an entire length of the middle body portion, wherein at least a portion of the middle portion of the fluid flow guide is axially expandable;

transvascularly introducing the stent-graft into an aorta of a human subject, while the stent-graft is positioned in a delivery catheter in the radially-compressed state;

deploying the rostral body portion from the delivery catheter into the aorta in a vicinity of renal arteries of the subject;

deploying the middle body portion from the delivery catheter into the aorta caudal to the renal arteries; and deploying the caudal body portion from the delivery catheter into the aorta in a vicinity of iliac arteries of the subject, such that the axially-expandable portion of the middle portion of the fluid flow guide expands so that the single, non-bifurcated lumen entirely spans an abdominal aorta between the renal arteries and an aorto-iliac bifurcation, without extending into the aorto-iliac bifurcation more than 1 cm.

For some applications, the method further includes identifying the subject as suffering from an aortic aneurysm, and introducing includes transvascularly introducing the stent-graft responsively to the identifying.

For some applications, providing includes providing the stent-graft in which a rostral portion of the fluid flow guide that at least partially covers the rostral structural member is shaped so as to define a rostral bulge that extends radially outward, and a caudal portion of the fluid flow guide that at least partially covers the caudal structural member is shaped so as to define a caudal bulge that extends radially outward, deploying the rostral body portion includes deploying the rostral body portion such that the rostral bulge extends radially outward against and sealingly contacts a rostral portion of an abdominal aortic aneurysm in the aorta when the stent-graft assumes the radially-expanded state, and deploying the caudal body portion includes deploying the caudal body portion such that the caudal bulge extends radially outward against and sealingly contacts a caudal portion of the abdominal aortic aneurysm in the aorta when the stent-graft assumes the radially-expanded state.

For some applications, a portion of the caudal structural member is flared radially outward at a caudal end thereof, when the stent-graft assumes the radially-expanded state, and deploying the caudal body portion includes deploying the caudal body portion such that the flared portion is adjacently caudal to an aorto-iliac bifurcation.

For some applications, the method further includes: introducing via a first iliac artery to a second iliac artery a bi-iliac self-expandable stent in a radially-compressed state so that the bi-iliac stent subtends the aorto-iliac bifurcation; deploying the bi-iliac stent to a radially-expanded state; and introducing and inflating a balloon in the bi-iliac stent.

For some applications, the stent-graft further includes an iliac extension stent, which is connected to an element selected from the group consisting of: a caudal end of the caudal body portion, or the caudal structural member within the caudal body portion, and further including deploying the iliac extension stent in a first one of the iliac arteries after deploying the caudal body portion into the aorta. For some applications, the iliac extension stent is shaped such that a rostral portion thereof defines a lateral opening therethrough, defined by a discontinuity of stents cells of the extension stent, subtending an arc angle of more than 320 degrees. For some applications, the method further includes: introducing a bi-iliac self-expandable stent via the deployed iliac extension stent to a second one of the iliac arteries in a radially-compressed state such that the bi-iliac stent subtends an aorto-iliac bifurcation; deploying the bi-iliac to a radially-expanded state; and introducing and inflating a balloon in the bi-iliac stent.

The present invention will be more fully understood from the following detailed description of embodiments thereof, taken together with the drawings, in which:

BRIEF DESCRIPTION OF THE DRAWINGS

FIGS. 7A-C are schematic illustrations of an endovascular prosthesis comprising a plurality of tissue engagement members, in accordance with respective applications of the present invention;

FIGS. 15A-C are schematic illustrations of the unilumen endovascular stent-graft of FIG. 13 coupled to a uni-iliac self-expandable extension stent, in accordance with respective applications of the present invention;

FIG. 18 is a schematic illustration of a configuration of the unilumen endovascular stent-graft of FIG. 13 further comprising a self-expandable uni-iliac extension stent, in accordance with an application of the present invention;

FIG. 19 is a schematic illustration of the unilumen endovascular stent-graft of FIG. 13 coupled to a uni-iliac self-expandable stent, in accordance with an application of the present invention;

DETAILED DESCRIPTION OF APPLICATIONS

Endovascular Stent-Graft Having a Bulge

Figure 1:
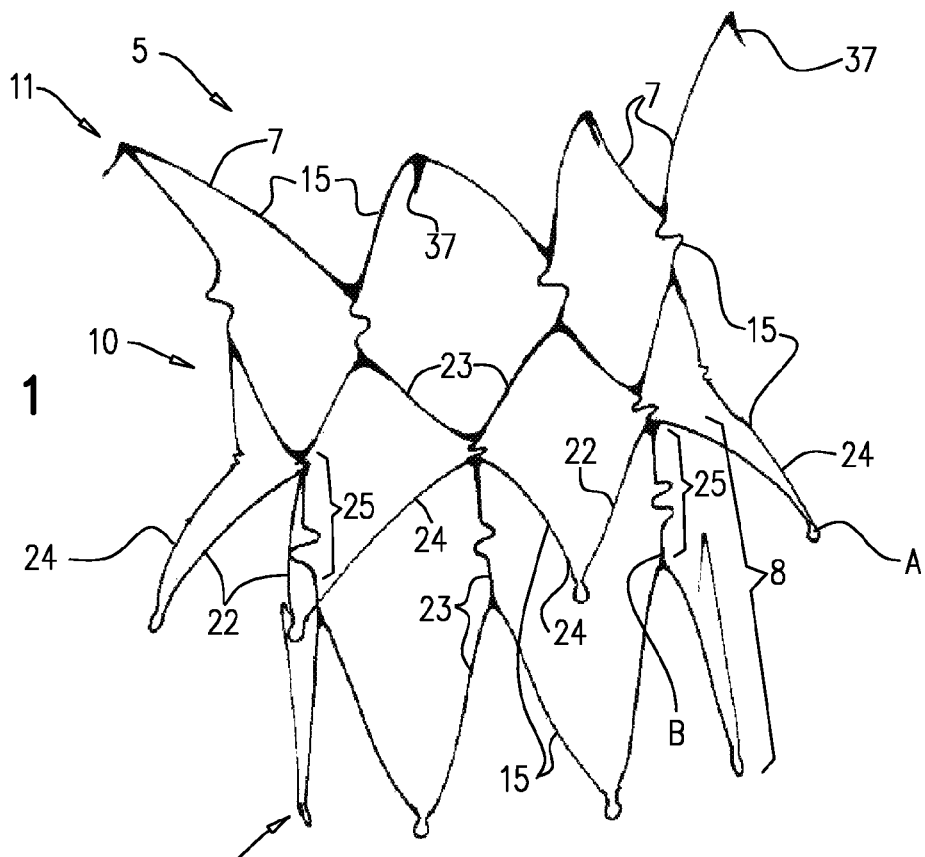
FIGS. 1 and 2 are schematic illustrations of an endovascular stent-graft, in accordance with an application of the present invention.
Figure 2:
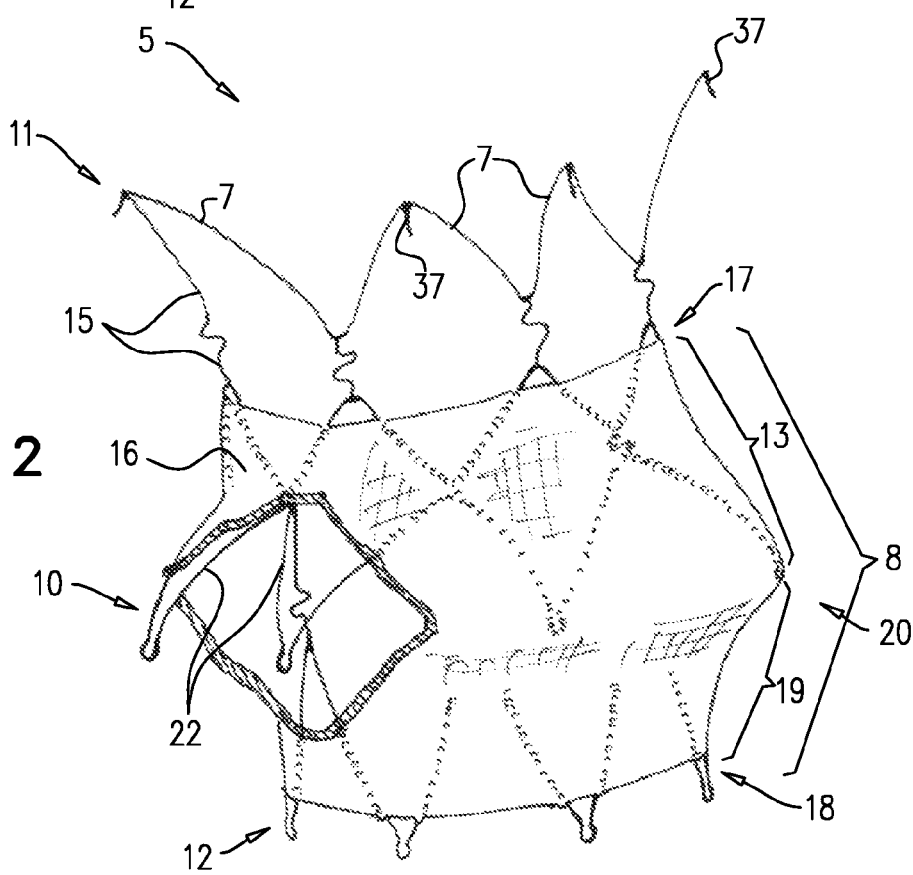

FIGS. 1 and 2 are schematic illustrations of an endovascular stent-graft 5, in accordance with an application of the present invention. Endovascular stent-graft 5 is configured to initially be positioned in a delivery catheter in a radially-compressed state, as described hereinbelow with reference to FIG. 4A, and to assume a radially-expanded state upon being deployed from the delivery catheter, as described hereinbelow with reference to FIGS. 4B-E. FIGS. 1 and 2 show the endovascular stent-graft in the radially-expanded state. For some applications, the stent-graft, and other stent-grafts and prostheses described herein, are heat-set to assume the radially-expanded state.

Stent-graft 5 comprises a structural member 10 and a fluid flow guide 16. FIG. 1 shows only the structural member, while FIG. 2 shows the fluid flow guide fixed to the structural member. Structural member 10 comprises a plurality of structural stent elements 15. For some applications, at least some of, e.g., all of, the structural stent elements are interconnected (as shown in the figures), while for other applications, at least a portion of, e.g., all, of the structural stent elements are not interconnected (configuration not shown). For some applications, a rostral-most first portion of structural stent elements 15 define a plurality of anchoring elements 7 that extend radially outwardly, and, optionally, rostrally, when the stent-graft assumes the radially-expanded state, as shown in FIGS. 1 and 2. The anchoring elements anchor the stent-graft to the vascular wall, helping prevent dislodgement. Optionally, one or more of anchoring elements 7 are shaped so as to define respective barbs 37. (As used in the present application, including in the claims, a "barb" means an element having at least one free sharp end, which is sharp enough to enter the aortic wall. The element does not necessarily define a sharp projection extending backward from the sharp end for preventing easy extraction.) A second portion of structural stent elements 15 define a stent body 8 when the stent-graft assumes the radially-expanded state. The second portion of members 15 are typically coupled to the first portion of members 15, and immediately caudal to the first portion. Structural member 10 has a rostral end 11 and a caudal end 12, between which stent body 8 is positioned. For some applications, structural member 10 comprises a metal. Alternatively or additionally, the structural member comprises a self-expanding material. Alternatively or additionally, the structural member comprises a super-elastic alloy, such as Nitinol.

As shown in FIG. 2, fluid flow guide 16 comprises at least one biologically-compatible substantially fluid-impervious flexible sheet, which is coupled to stent body 8, either outside or within the body, such as by stitching, and covers either an external or an internal surface of at least a portion of the stent body. (FIG. 2 shows a cut-out portion of fluid flow guide 16 to better show structural stent elements 15 within the fluid flow guide.) Fluid flow guide 16 has a rostral end 17 and a caudal end 18. Fluid flow guide 16 typically covers the entire stent body, in order to define a fluid flow path through the body. The flexible sheet may comprise, for example, a polymeric material (e.g., polytetrafluoroethylene), a textile material (e.g., polyethylene terephthalate (PET)), natural tissue (e.g., saphenous vein or collagen), or a combination thereof. Optionally, caudal end 12 of structural member 10 extends beyond a caudal end of stent body 8 and caudal end 18 of fluid flow guide 16, for example, slightly beyond, as shown in FIG. 2; stent body 8 thus does not include a caudal-most portion of structural stent elements 15 that extend caudally beyond caudal end 18 of fluid flow guide 16. For some applications, rostral end 17 of fluid flow guide 16 is disposed within 1-4 cm of rostral end 11 of structural member 10. For some applications, caudal end 18 of the fluid flow guide is disposed within 0.5-2 cm of caudal end 12 of the structural member.

When the stent-graft assumes the radially-expanded state, fluid flow guide 16 is shaped so as to define radially-diverging and radially-converging portions 13 and 19, typically within 10 cm of a rostral end of the stent body. The portions together define a bulge 20 that extends radially outward, which has a greatest cross-sectional area that is equal to at least 120%, e.g., at least 160%, of a cross-sectional area of a narrowest portion 17 of the stent-graft rostral to the bulge (the stent-graft may have an even narrower portion caudal to the bulge). When the stent-graft is deployed in the aorta, bulge 20 extends radially outward against a rostral portion of the aortic aneurysm, thereby helping prevent a current or a future type I endoleak. Typically, when the stent-graft assumes the radially-expanded state, a site on bulge 20 that has the greatest cross-section area is within 5 cm, at least 2 cm from, and/or between 2 and 5 cm of rostral end 17 of fluid flow guide 16.

Typically, the stent-graft is configured such that bulge 20 expands radially as the rostral end of the aneurysm enlarges post-implantation, in order to maintain a tight seal with the wall of the aorta, thereby preventing current or future type I endoleaks. At the same time, the stent-graft is configured to apply a radially-outward force that is sufficient to cause the bulge to expand with the aortic wall, but insufficient to itself cause expansion of the aortic wall. For some applications, structural member 10 is configured such that, when the stent-graft assumes the radially-expanded state, bulge 20 applies a radially-outward force that is less than a radially-outward force applied by anchoring elements 7. For example, the radially-outward force applied by the bulge may be at least 25%, no more than 50%, and/or between 25% and 50% of the radially-outward force applied by the anchoring elements. For example, the anchoring elements may be configured to apply more than half a newton, no more than five newton, or between one half a newton and five newton to the aortic wall (or more generally, if placed within a cylinder having a diameter of 2.5 cm).

Typically, a first subset 22 of structural stent elements 15 of stent body 8 are configured to cause fluid flow guide 16 to define bulge 20, when the stent-graft assumes the radially-expanded state. For some applications, a second subset 23 of structural stent elements 15 of stent body 8 are not configured to cause fluid flow guide 16 to define bulge 20, when the stent-graft assumes the radially-expanded state. The structural stent elements of first subset 22 at least partially overlap the structural stent elements of second subset 23 lengthwise along the stent body, and the structural stent elements of first subset 22 are positioned generally radially outward from the structural stent elements of second subset 23 when the stent-graft assumes the radially-expanded state. For some applications, structural stent elements 15 comprise a metal, and, when the stent-graft assumes the radially-compressed state, structural stent elements 15 of first subset 22 contact at least a portion of structural stent elements 15 of second subset 23. Typically, structural stent elements 15 of first subset 22 are interconnected. Alternatively or additionally, structural stent elements 15 of second subset 23 are interconnected.

For some applications, the structural stent elements of first subset 22 radially converge with the structural stent elements of second subset 23 at respective rostral ends of the subsets (as shown in the figures), and/or at respective caudal ends of the subsets (configuration not shown). For some applications, a third subset 25 of structural stent elements 15 of stent body 8 connect structural stent elements 15 of first subset 22 with the structural stent elements of second subset 23, and thus as communicating support members. Optionally, when the stent-graft assumes the radially-expanded state, structural stent elements 15 of third subset 25 are substantially radially oriented.

For some applications, when the structural member assumes the radially-expanded state, structural stent elements 15 of first subset 22 are concentric with the structural stent elements of second subset 23. For some applications, first and second subsets 22 and 23 are mutually exclusive, i.e., do not contain any common, mutual structural stent elements 15. For other applications, the first and second subsets share at least one of the structural members, i.e., at least one of the structural members is a member of both the first and second subsets. For some applications, third subset 25 is mutually exclusive with both first and second subsets 22 and 23, while for other applications, the third subset shares at least one structural member with the first subset and/or the second subset.

Typically, first subset 22 (which causes fluid flow guide 16 to define bulge 20) has a lower spring coefficient than second subset 23. More specifically, assume a radial force were to be applied by two rigid circular disks to two respective regions on stent body 8, respectively centered at: (1) a point A of first subset 22 that is furthest from a central longitudinal axis of the stent body, and (2) a point B of second subset 23 that is axially aligned with point A, wherein each of the circular disks has a radius equal to 50% of a radius of stent body 8 at point A. For some applications, a spring coefficient of first subset 22, measured during application of the radial force at the region around point A, is at least 20% less than a spring coefficient of second subset 23, measured during application of the radial force at the region around point B. For some applications, a spring coefficient of first subset 22, measured during application of a radial force at the region around point A, is at least 20% less than a spring coefficient of rostral anchoring elements 7, measured during application of the radial force at a region around a point of the anchoring elements that is furthest from the axis of the stent body.

For some applications, when the stent-graft assumes the radially-expanded state, structural stent elements 15 of second subset 23 (which do not cause the fluid flow guide to define the bulge) are shaped so as to define a substantially tubular structure, e.g., a constant diameter cylinder, or a flared cylinder, which is configured to retain a generally constant diameter even as the bulge expands radially outward over time post-implantation. As used in the present application, including in the claims, "tubular" means having the form of an elongated hollow object that defines a conduit therethrough. A "tubular" structure may have varied cross-sections therealong, and the cross-sections are not necessarily circular. For example, one or more of the cross-sections may be generally elliptical but not circular, or circular.

For some applications, when the stent-graft assumes the radially-expanded state, structural stent elements 15 of first subset 22 (which cause fluid flow guide 16 to define bulge 20) are shaped so as to define a plurality of arms 24 that extend radially outward, and are configured to cause fluid flow guide 16 to define bulge 20. Typically, when the stent-graft assumes the radially-expanded state, arms 24 extend radially outward in a caudal direction, as shown in FIGS. 1 and 2. Alternatively, the arms extend radially outward in a rostral direction.

For some applications, structural stent elements 15 of first subset 22 define an external structural lumen, which is disposed radially outward of an internal structural lumen defined by structural stent elements 15 of second subset 23 when the stent-graft assumes the radially-expanded state. The external structural lumen at least partially overlaps the internal structural lumen lengthwise along the stent body. (As used in the present application, including in the claims, a "structural lumen" means a passageway defined by structural stent elements 15, even though the passageway does not necessarily define a fluid flow path.) The diameter of body portion 8 of the external structural lumen is mostly larger than the diameter of the body portion of the internal structural lumen.

For some applications, when the stent-graft assumes the radially-expanded state, structural stent elements 15 of first subset 22 are grouped into a plurality of axially-disposed arrays, each of which arrays generally circumscribes at least a 360-degree arc. Each of the arrays is substantially morphologically deformable independently of the axially adjacent arrays. As a result, deformation of each of the arrays has minimal impact on the axially adjacent arrays, providing the bulge with good surface conformation to the end of the aneurysm, thereby sealing the aneurysm end. For some applications, at least a portion (e.g., all) of the arrays are structurally connected to the axially adjacent arrays, by connecting stent elements. These connections provide some columnar strength to first subset 22. For other applications, at least a portion (e.g., none) of the arrays are not structurally connected to the axially adjacent arrays, such that at least a portion of the arrays serve as bare crowns.

Figure 3:
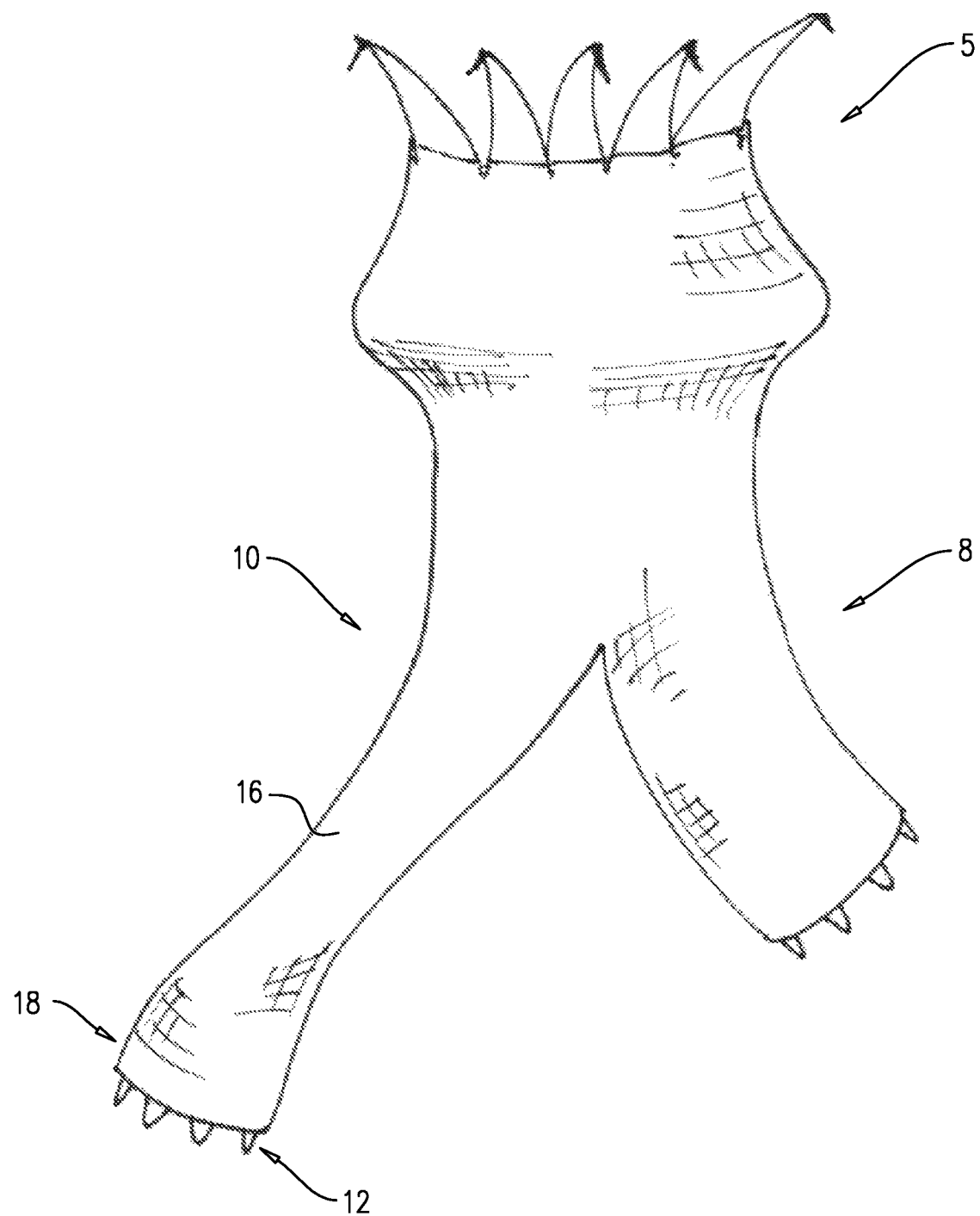
FIG. 3 is a schematic illustration of a bifurcated configuration of the endovascular stent-graft of FIGS. 1 and 2, in accordance with an application of the present invention.

FIG. 3 is a schematic illustration of a bifurcated configuration of stent-graft 5, in accordance with an application of the present invention. In this configuration, stent body 8 is bifurcated, such that the stent body is shaped so as to define two branches, which define respective lumens. (The branches typically have differing lengths, as is known in the art for conventional stent-grafts.) Alternatively, when the stent-graft assumes the radially-expanded state, the caudal end of the structural member and the caudal end of the fluid flow guide together define a single lumen, as shown in FIG. 2.

Figure 4A:
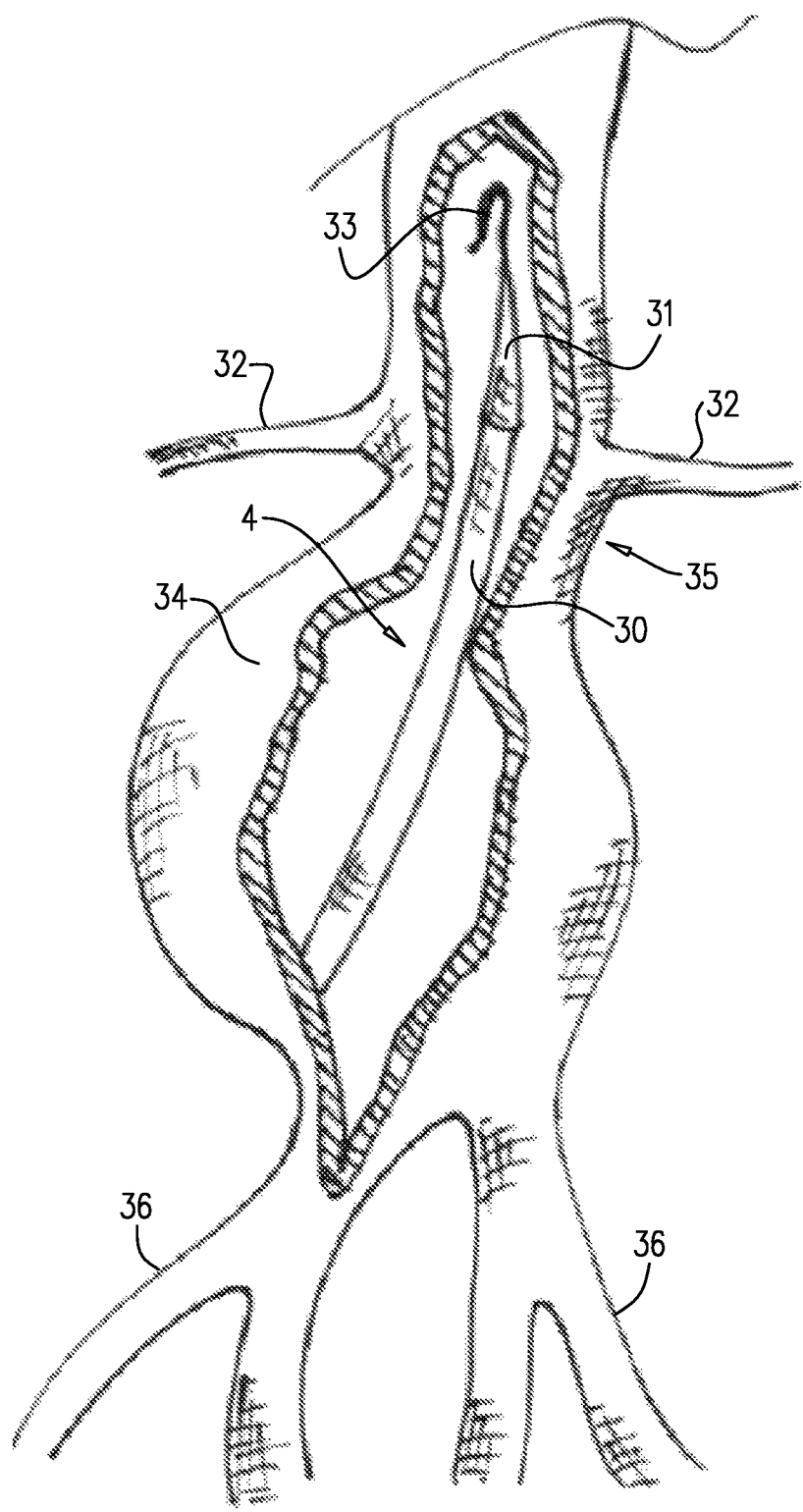
FIGS. 4A-D are schematic illustrations of an exemplary method of deploying the endovascular stent-graft of FIGS. 1 and 2 in a rostral end of an abdominal aortic aneurysm, in accordance with an application of the present invention.

FIGS. 4A-D are schematic illustrations of an exemplary method of deploying endovascular stent-graft 5 in a rostral end 35 of an abdominal aortic aneurysm 34, using an endovascular stent-graft delivery tool 4, in accordance with an application of the present invention. As shown in FIG. 4A, delivery tool 4 typically comprises a delivery catheter 30, a distal tip 31, and a guidewire 33. In order to implant endovascular stent-graft 5, the stent-graft is transvascularly (typically percutaneously) introduced into the aorta via one of iliac arteries 36, while the stent-graft is positioned in delivery catheter 30 in the radially-compressed state. Delivery catheter 30 and distal tip 31 are advanced over guidewire 33 until the distal tip is positioned slightly below renal arteries 32.

Figure 4B:
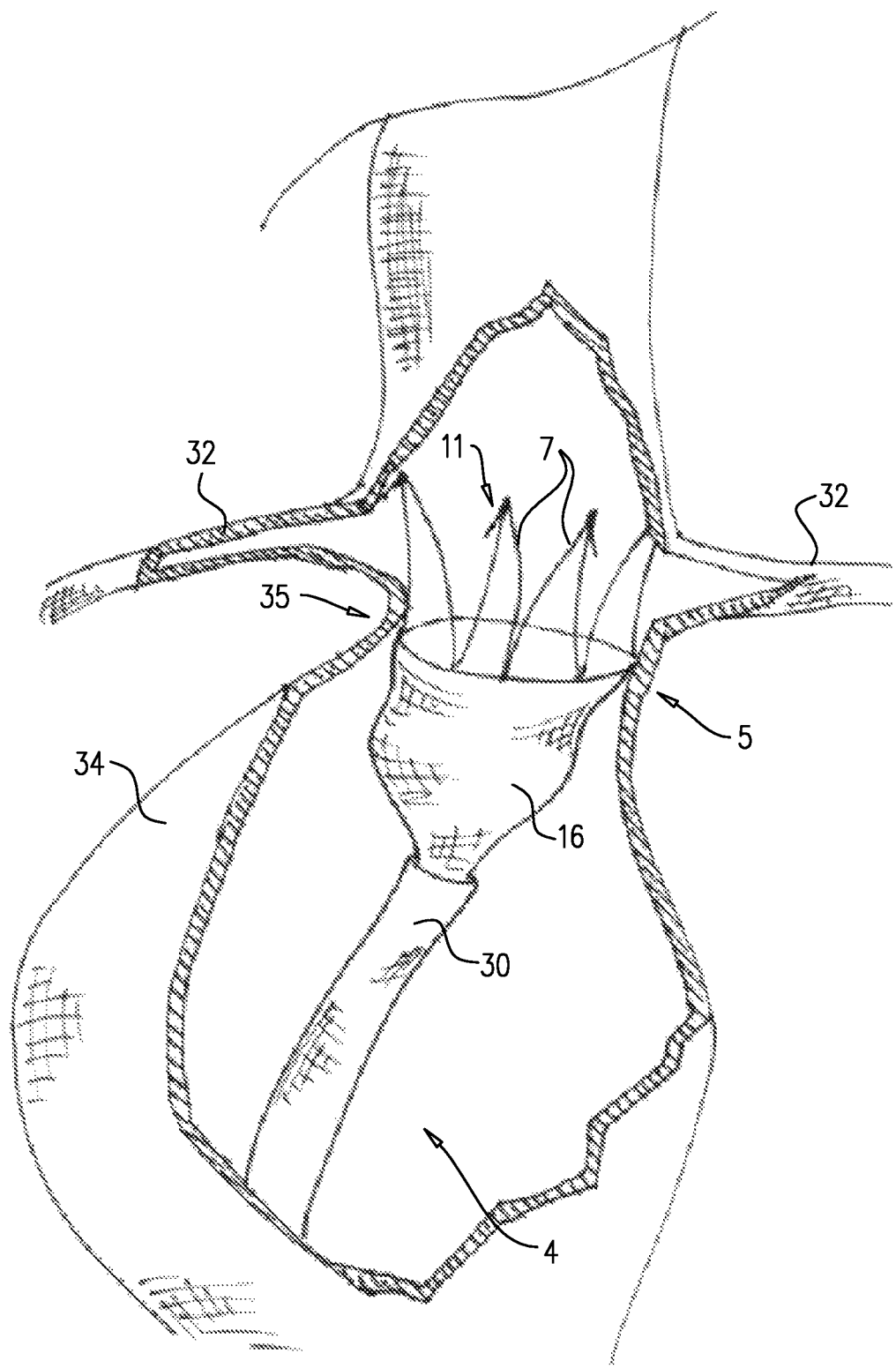

FIG. 4B shows rostral end 11 of structural member 10 in an early stage of release from delivery catheter 30. The stent-graft is positioned such that rostral anchoring elements 7 are disposed rostrally to renal arteries 32.

Figure 4C:
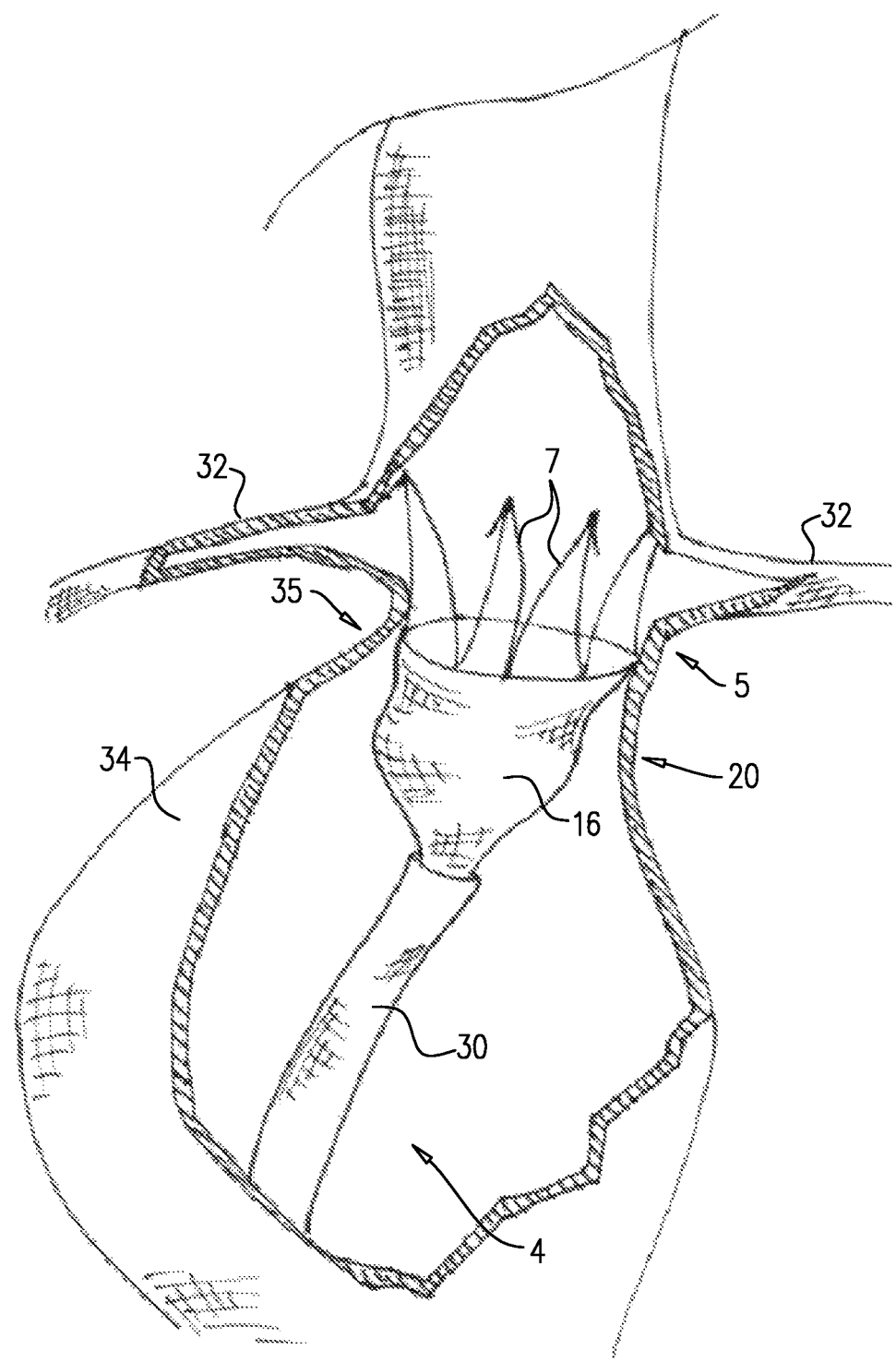

FIG. 4C shows the stent-graft in a subsequent phase of its deployment from delivery catheter 30, in which bulge 20 is disposed in rostral end 35 of aneurysm 34, and sealingly contacts the aortic wall, thereby preventing or reducing the risk of a current or a future a type I endoleak.

Figure 4D:
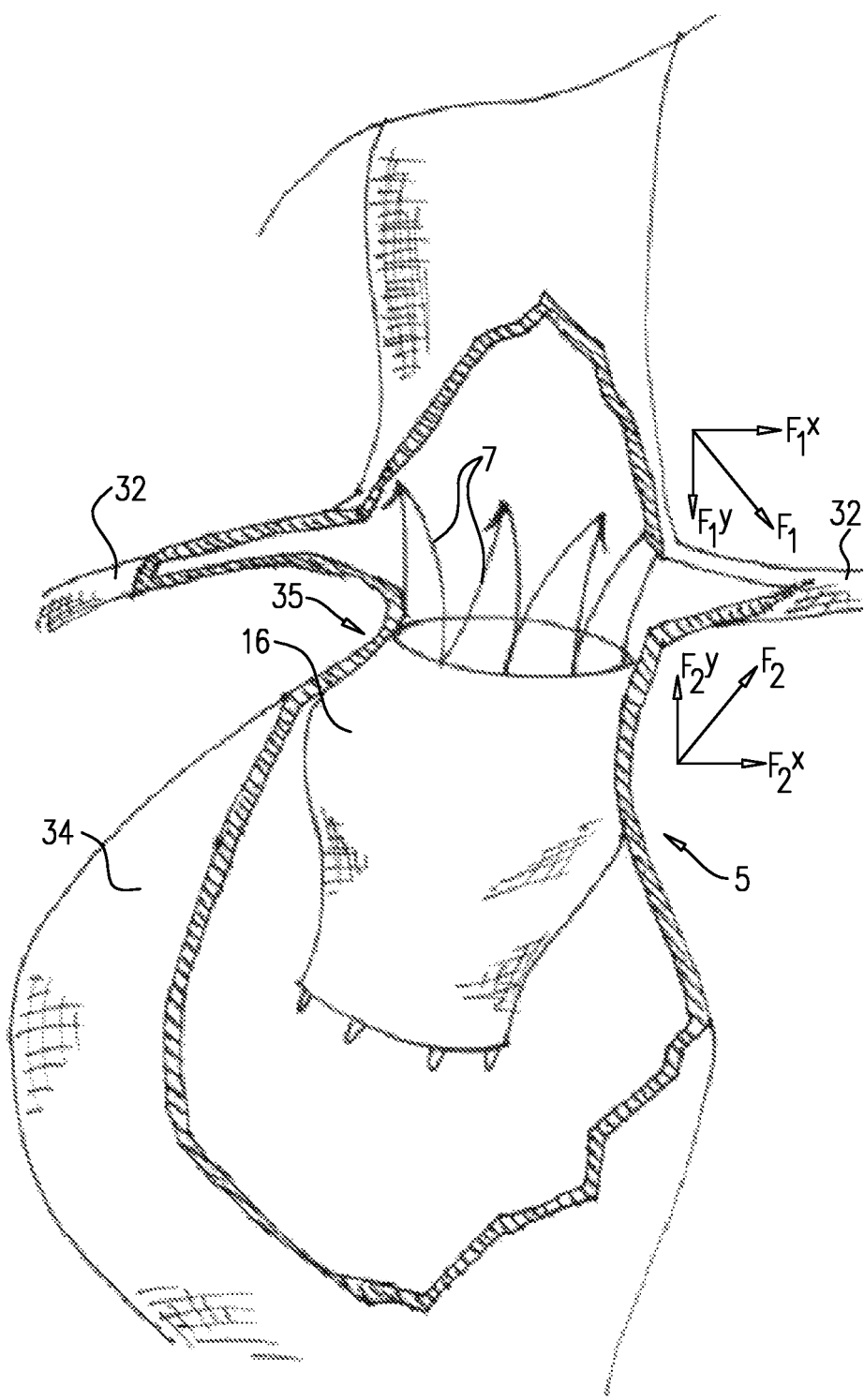

FIG. 4D shows the stent-graft in its fully deployed state, after delivery tool 4 has been removed from the subject's body. At least one additional primary stent-graft may be coupled to the caudal end of the stent-graft, such as using techniques described hereinbelow with reference to FIG. 9D, mutatis mutandis (for clarity of illustration, not shown in FIG. 4D). The primary stent-graft is structurally coupled to second subset 23 of structural elements 15, which do not define the bulge, and may define the internal structural lumen. Alternatively, at least one additional primary stent-graft may be integral to the stent-graft, such that the stent-graft is sufficiently long to reach the aorta-iliac bifurcation.

Bulge 20 exerts a force against the wall of the aorta, labeled in FIG. 4D as force vector $F_2$. Force vector $F_2$ has both vertical and horizontal components $F_2y$ and $F_2x$. Similarly, anchoring elements 7 exert a force against the wall of the aorta, labeled as force vector $F_1$. Force vector $F_1$ has both vertical and horizontal components $F_1y$ and $F_1x$. The vertical force components $F_1y$ and $F_2y$ are directed towards one another, so as to axially pinch the aortic wall between the neck of the aneurysm and the rostral end of the aneurysm, thereby enhancing the anchoring of the stent-graft to the wall of the aorta, and reducing the likelihood of loosening of the prosthesis which may result in a type I endoleak.

Figure 4E:
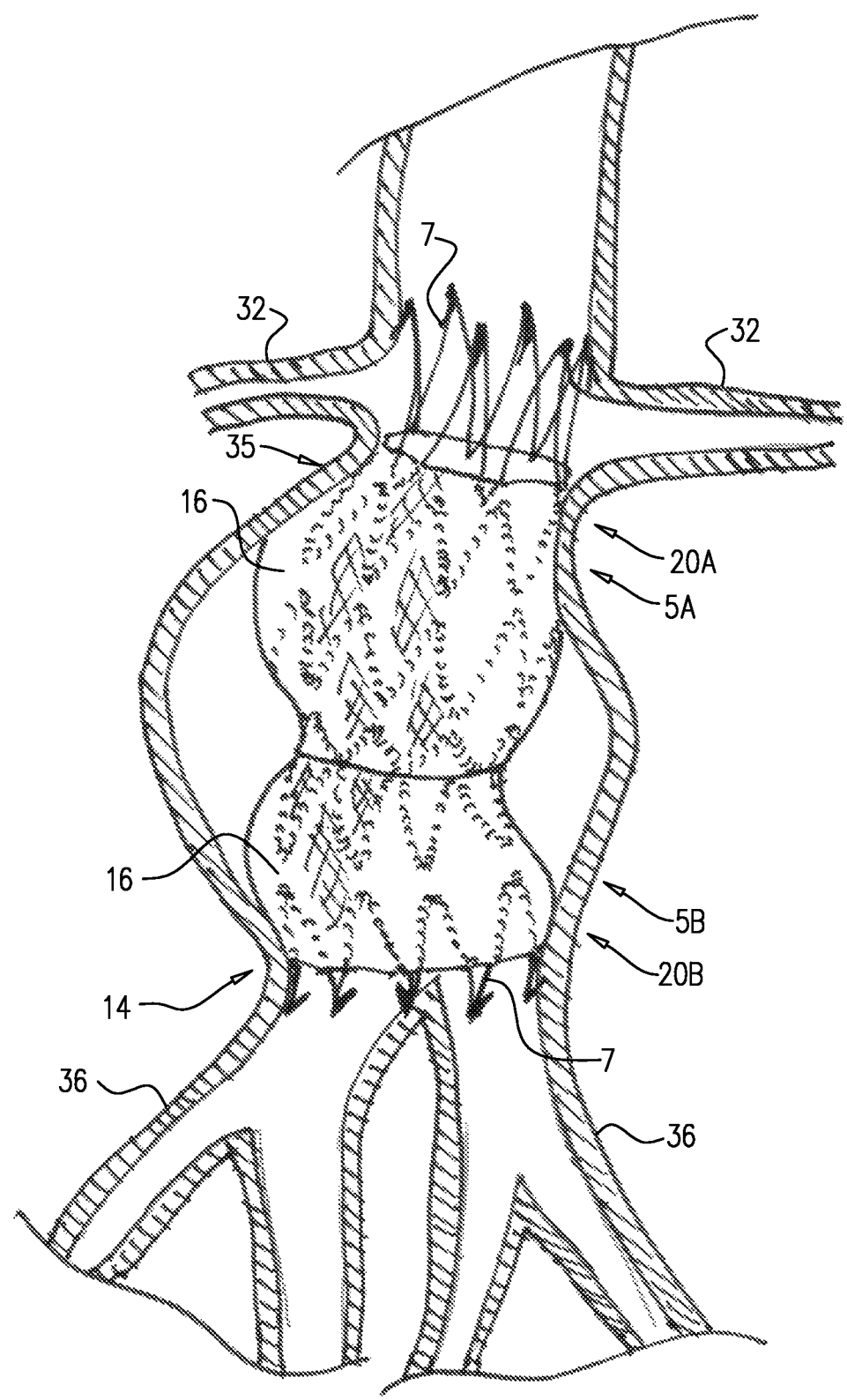
FIG. 4E schematically illustrates two of the stent-grafts of FIGS. 1 and 2 in their respective fully deployed states, in accordance with an application of the present invention.

FIG. 4E schematically illustrates two of stent-grafts 5A and 5B in their respective fully deployed states, in accordance with an application of the present invention. A first stent-graft 5A has its bulge 20A disposed in rostral end 35 of aneurysm 34, thereby preventing a current or a future a type I endoleak. A second stent-graft 5B is oriented in an axial direction opposite to that of first stent-graft 5A, and has its bulge 20B disposed in a caudal end 14 of aneurysm 34, near the bifurcation of the aorta into two iliac arteries 36, thereby preventing a current or a future a type endoleak at the aorto-iliac bifurcation. The caudal ends of the stent-grafts are deployed one inside the other, in order to provide fluid-tight coupling of the stent-grafts with each other. Optionally, anchoring elements 7 of second stent-graft 5B are positioned to engage an aorta-iliac bifurcation.

Endovascular Stent-Graft Having a Foldable Skirt

Figure 5A:
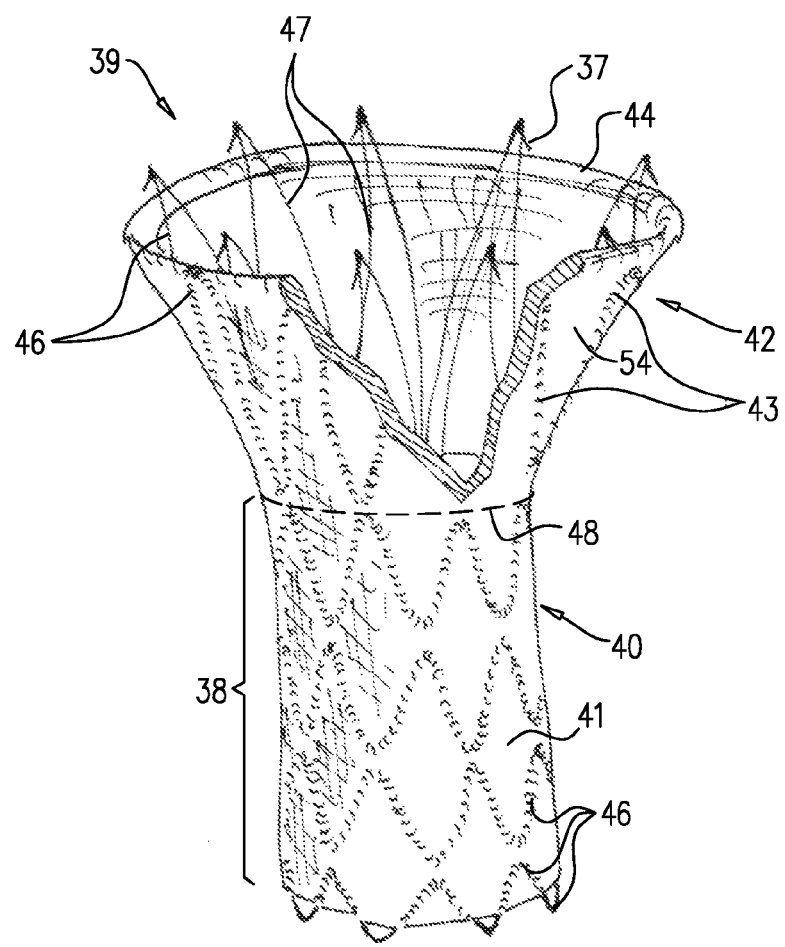
FIGS. 5A-B are schematic illustrations of an endovascular stent-graft comprising a foldable skirt, in accordance with an application of the present invention.
Figure 5B:
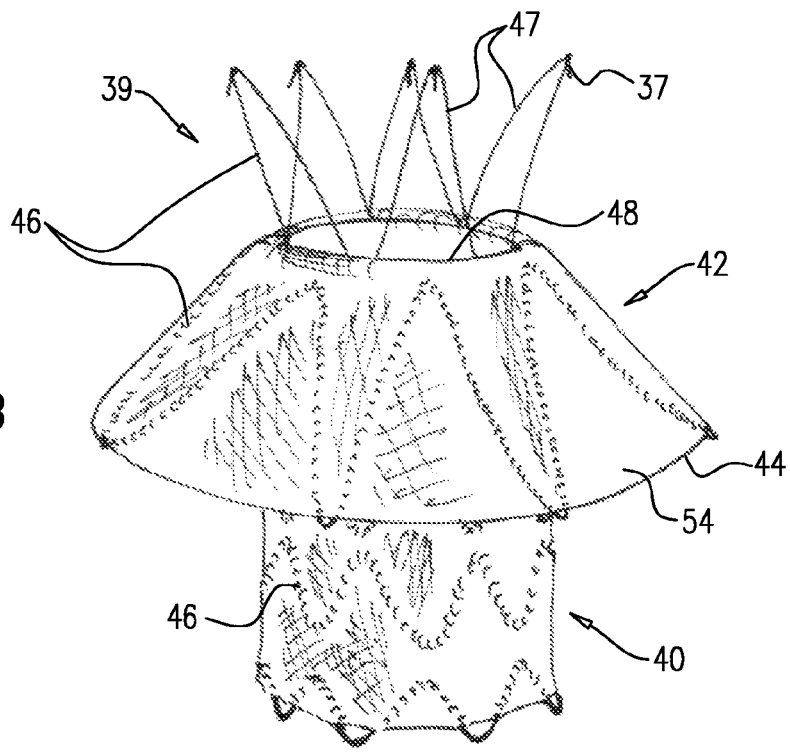

FIGS. 5A-B are schematic illustrations of an endovascular stent-graft 39 comprising a foldable skirt 42, in accordance with an application of the present invention. Endovascular stent-graft 39 is configured to initially be positioned in a delivery catheter in a radially-compressed state, as described hereinbelow with reference to FIG. 6A, and to assume a radially-expanded state upon being deployed from the delivery catheter, as described hereinbelow with reference to FIGS. 6B-D. FIGS. 5A-B show the endovascular stent-graft in the radially-expanded state.

Stent-graft 39 comprises a structural member 40 and a fluid flow guide 41. Structural member 40 comprises a plurality of structural stent elements 46. For some applications, at least some of, e.g., all of, the structural stent elements are interconnected (as shown in the figures), while for other applications, at least a portion of, e.g., all of, the structural stent elements are not interconnected (configuration not shown). (The structural stent elements, other than those that define anchoring elements 47, are not directly visible in the figures; however, the positioning of the structural stent elements is indicated by the stitching that couples fluid flow guide 41 to the flexible sheet of the skirt to the structural stent elements. This is also the case for other configurations shown with stitching in some of the other figures.) For some applications, a rostral-most first portion of structural stent elements 46 define a plurality of anchoring elements 47 that extend radially outwardly and rostrally when the stent-graft assumes the radially-expanded state, as shown in FIGS. 5A-B. The anchoring elements anchor the stent-graft to the vascular wall, helping prevent dislodgement. Optionally, one or more of anchoring elements 47 are shaped so as to define respective barbs 37. A second portion of structural stent elements 46 define a tubular body 38 when the stent-graft assumes the radially-expanded state. The second portion of members 46 are typically coupled to the first portion of members 46, and immediately caudal to the first portion.

Fluid flow guide 41 comprises at least one biologically-compatible substantially fluid-impervious flexible sheet, which is coupled to tubular body 38, either outside the body or within the body, such as by stitching, and covers either an external or an internal surface of at least a portion of the tubular body. Fluid flow guide 41 typically covers the entire tubular body, in order to define a fluid flow path through the body. The flexible sheet may comprise, for example, a polymeric material (e.g., polytetrafluoroethylene), a textile material (e.g., polyethylene terephthalate (PET)), natural tissue (e.g., saphenous vein or collagen), or a combination thereof. Optionally, a caudal end of structural member 40 extends beyond a caudal end of tubular body 38 and a caudal end of fluid flow guide 41, for example, slightly beyond, as shown in FIGS. 5A-B; tubular body 38 thus does not include a caudal-most portion of structural stent elements 46 that extend caudally beyond the caudal end of fluid flow guide 41. For some applications, a caudal end of the fluid flow guide is disposed within 5 cm of, at least 2 cm from, and/or between 2 and 5 cm of a caudal end of the structural member.

Stent-graft 39 further comprises rostrally-positioned foldable skirt 42, which comprises at least one biologically-compatible substantially fluid-impervious flexible sheet 54. (FIG. 5A shows a cut-out portion of skirt 42 to better show anchoring elements 47.) Skirt 42 extends from structural member 40 at a circumferential juncture 48 between anchoring elements 47 and tubular body 38, and terminates in a peripheral edge 44. Peripheral edge 44 has a greater circumference than that of circumferential juncture 48 when the stent-graft assumes the radially-expanded state. For example, when the stent-graft assumes the radially-expanded state, the circumference of circumferential juncture 48 may be at least 10 cm, no more than 18 cm, and/or between 10 and 18 cm, and the circumference of peripheral edge 44 may at least 120%, no more than 150%, and/or between 120% and 150% of the circumference of circumferential juncture 48. Typically, the circumference of peripheral edge 44 is greater than a circumference of all other elements of the stent-graft, when the stent-graft assumes the radially-expanded state. The skirt is typically sealingly coupled to a rostral end of fluid flow guide 41 around the entire circumferential juncture. Typically, the peripheral edge has a non-traumatic shape, e.g., rounded, so as to minimize tissue trauma when the tissue applies the caudally oriented force, as described hereinbelow with reference to FIG. 6C.

Flexible sheet 54 of skirt 42 is typically supported by a scaffold 43, which typically extends from at least a portion of juncture 48 to at least a portion of peripheral edge 44 of the skirt. For some applications, the juncture comprises a pivot, to which the scaffold is rotatably coupled so as to allow the skirt to transition from extending rostrally to extending caudally, as described below. For some applications, scaffold 43 comprises a self-expanding material, and/or a super-elastic alloy, such as Nitinol.

FIG. 5A shows skirt 42 extending rostrally from circumferential juncture 48. The skirt assumes this position when the stent-graft is initially positioned in the delivery catheter, as described hereinbelow with reference with reference to FIG. 6A, and retains this position initially upon being deployed from the catheter, as described hereinbelow with reference to FIG. 6B. In this position, skirt 42 is positioned radially surrounding anchoring elements 47. This rostrally-extending position facilitates low-profile mounting of the endovascular stent-graft in the radially-compressed state within the delivery catheter.

FIG. 5B shows skirt 42 extending caudally from circumferential juncture 48, in order to facilitate sealing of blood leakage around the stent-graft when it assumes the radially-expanded state. The skirt assumes this position upon application of a caudally-directed force to peripheral edge 44 of the skirt after deployment of the stent-graft from the delivery catheter, as described hereinbelow with reference to FIG. 6C.

Figure 6A:
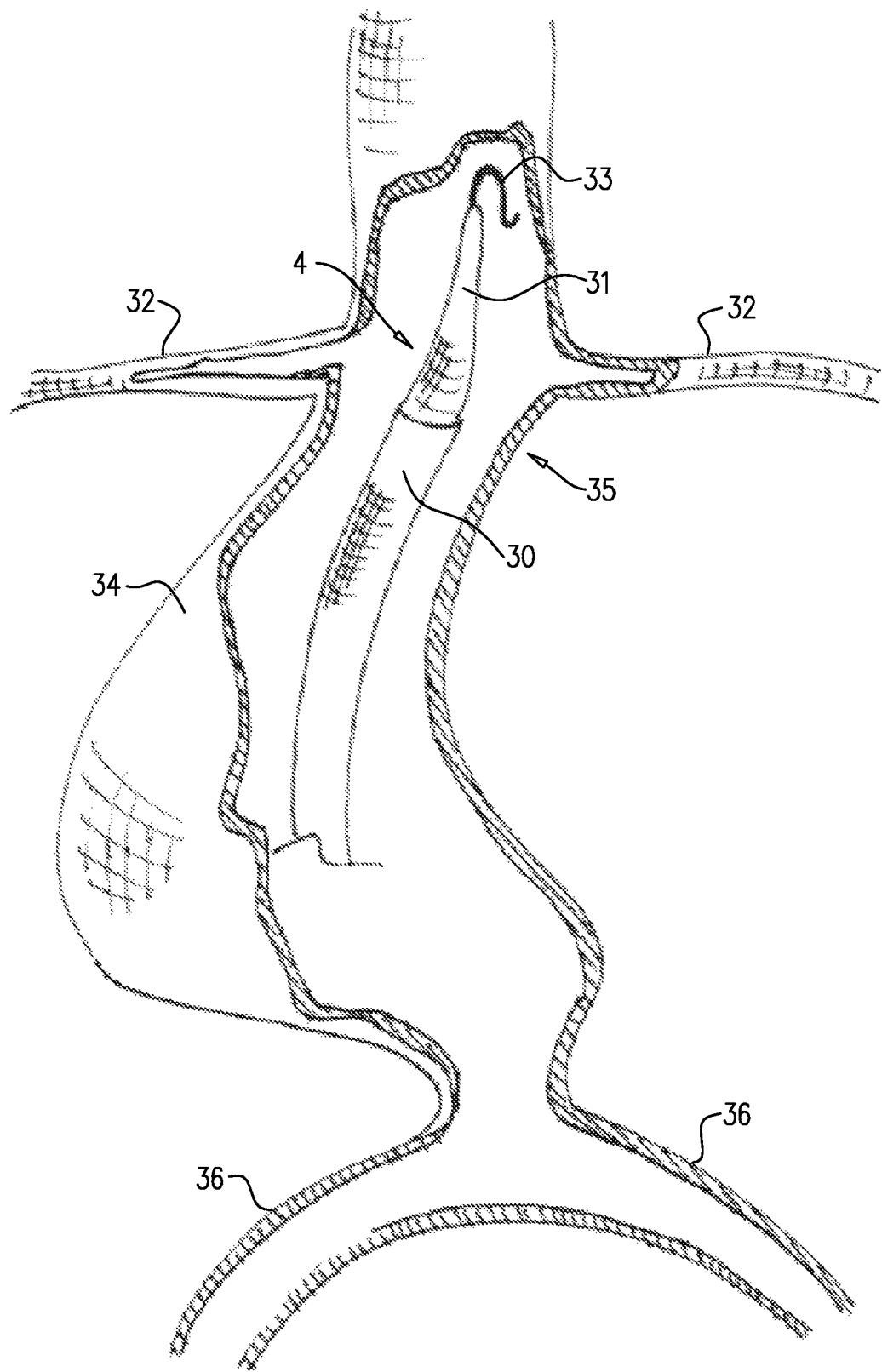
FIGS. 6A-D are schematic illustrations of an exemplary method of deploying the endovascular stent-graft of FIGS. 5A-B, in accordance with an application of the present invention.

FIGS. 6A-D are schematic illustrations of an exemplary method of deploying endovascular stent-graft 39 using endovascular stent-graft delivery tool 4, described hereinabove with reference to FIG. 4A, in accordance with an application of the present invention. As shown in FIG. 6A, in order to implant stent-graft 39, the stent-graft is transvascularly (typically percutaneously) introduced into the aorta via one of iliac arteries 36, while the stent-graft is positioned in delivery catheter 30 in the radially-compressed state. Delivery catheter 30 and distal tip 31 are advanced over guidewire 33 until the distal tip is positioned slightly below renal arteries 32.

Figure 6B:
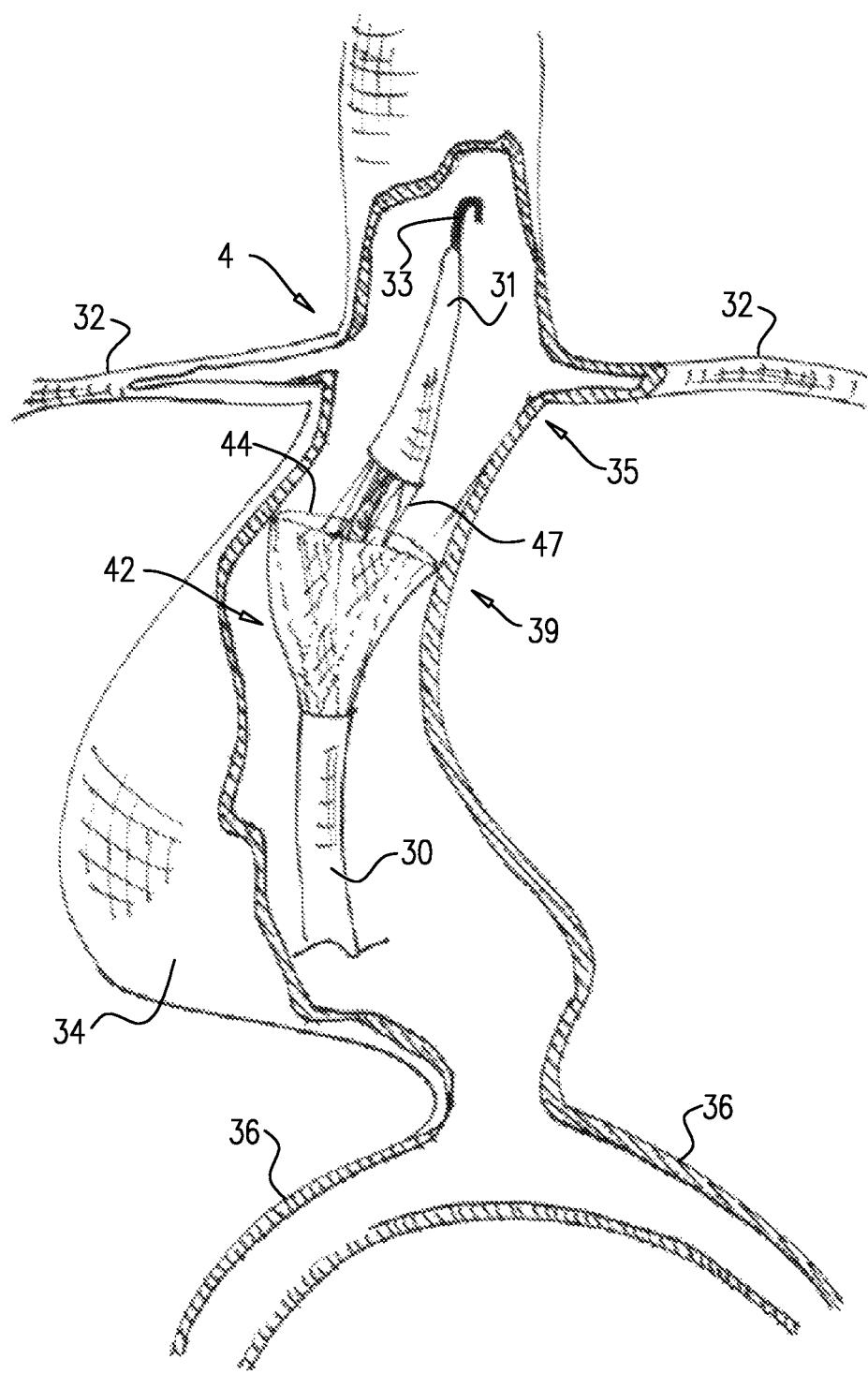

As shown in FIG. 6B, at least a portion of skirt 42, including peripheral edge 44, is deployed from catheter 30, such that the peripheral edge presses radially outward against the wall of the aorta a few centimeters into the aneurysm. Typically, at this stage of the method, anchoring elements 47 are still held in a radially-compressed state by distal tip 31 of the delivery tool. Subsequently, juncture 48 of skirt 42 is exposed.

Figure 6C:
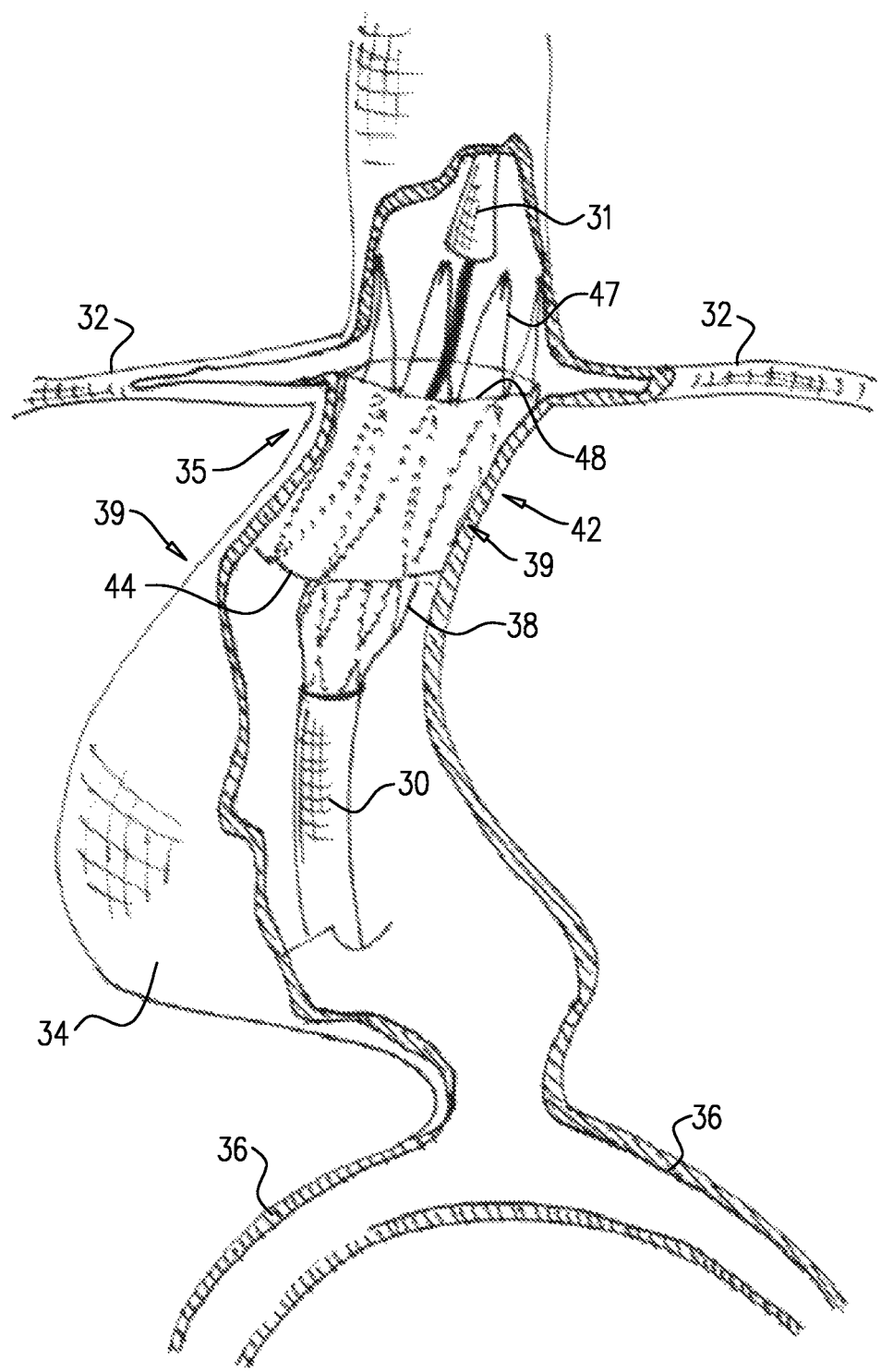

As shown in FIG. 6C, rostral advancement of the partially expanded skirt causes the wall of the aorta to apply a caudally-directed force to peripheral edge 44 of the skirt, causing the skirt to fold back, i.e., invert, in a caudal direction. The skirt extends caudally from the juncture in order to facilitate sealing of blood leakage around the stent-graft when it assumes the radially-expanded state. Circumferential juncture 48 between skirt 42 and tubular body 38 is disposed rostrally to peripheral edge 44 of skirt 42. Alternatively or additionally, the caudally-directed force is applied by one or more elongated members (e.g., cords) that are coupled to peripheral edge 44, and are pulled caudally in order to invert the skirt.

Figure 6D:
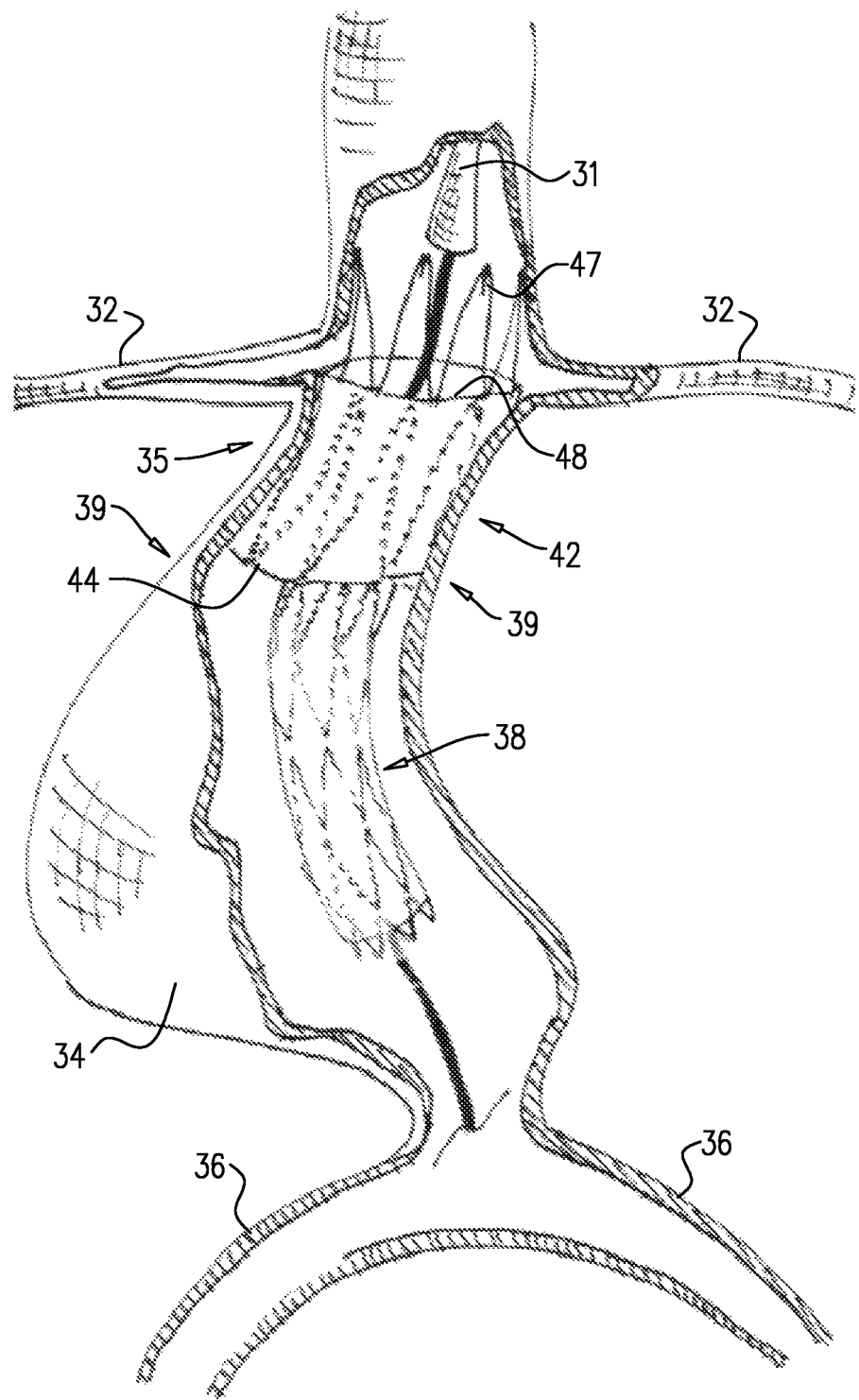

FIG. 6D shows the fully-deployed stent-graft system with skirt 42 positioned in rostral end 35 of aneurysm 34, thereby helping prevent a current or a future a type I endoleak. Delivery tool 4 is subsequently removed from the subject's body. One or more additional primary stent-grafts may be coupled to the caudal end of the stent-graft, such as using techniques described hereinbelow with reference to FIG. 9D, mutatis mutandis (for clarity of illustration, not shown in FIG. 6D). Alternatively, one or more additional primary stent-grafts may be integral to the stent-graft, such that the stent-graft is sufficiently long to reach the aorto-iliac bifurcation.

Endovascular Stent-Graft Having Tissue Engagement Members

Figure 7A:
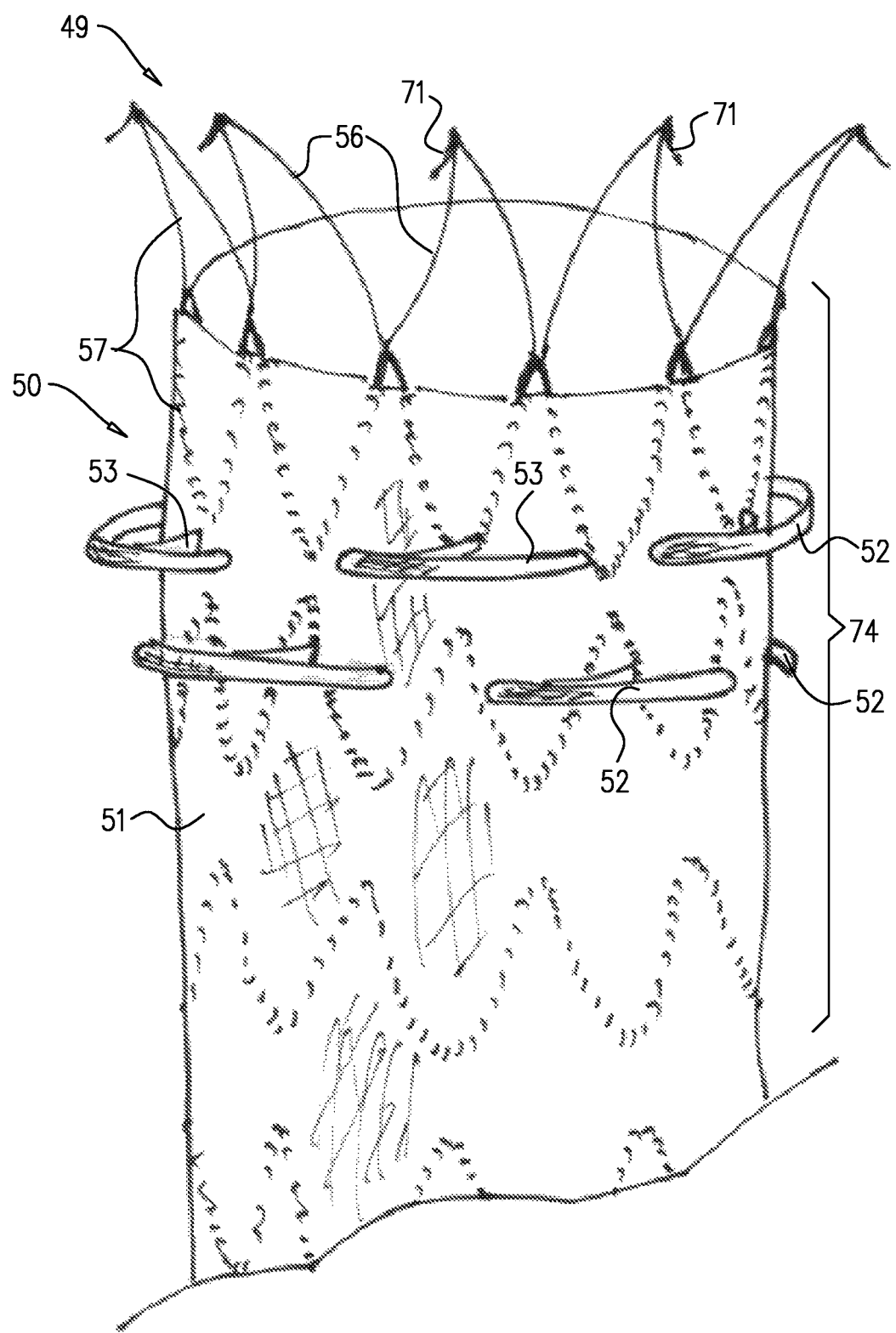
Figure 7B:
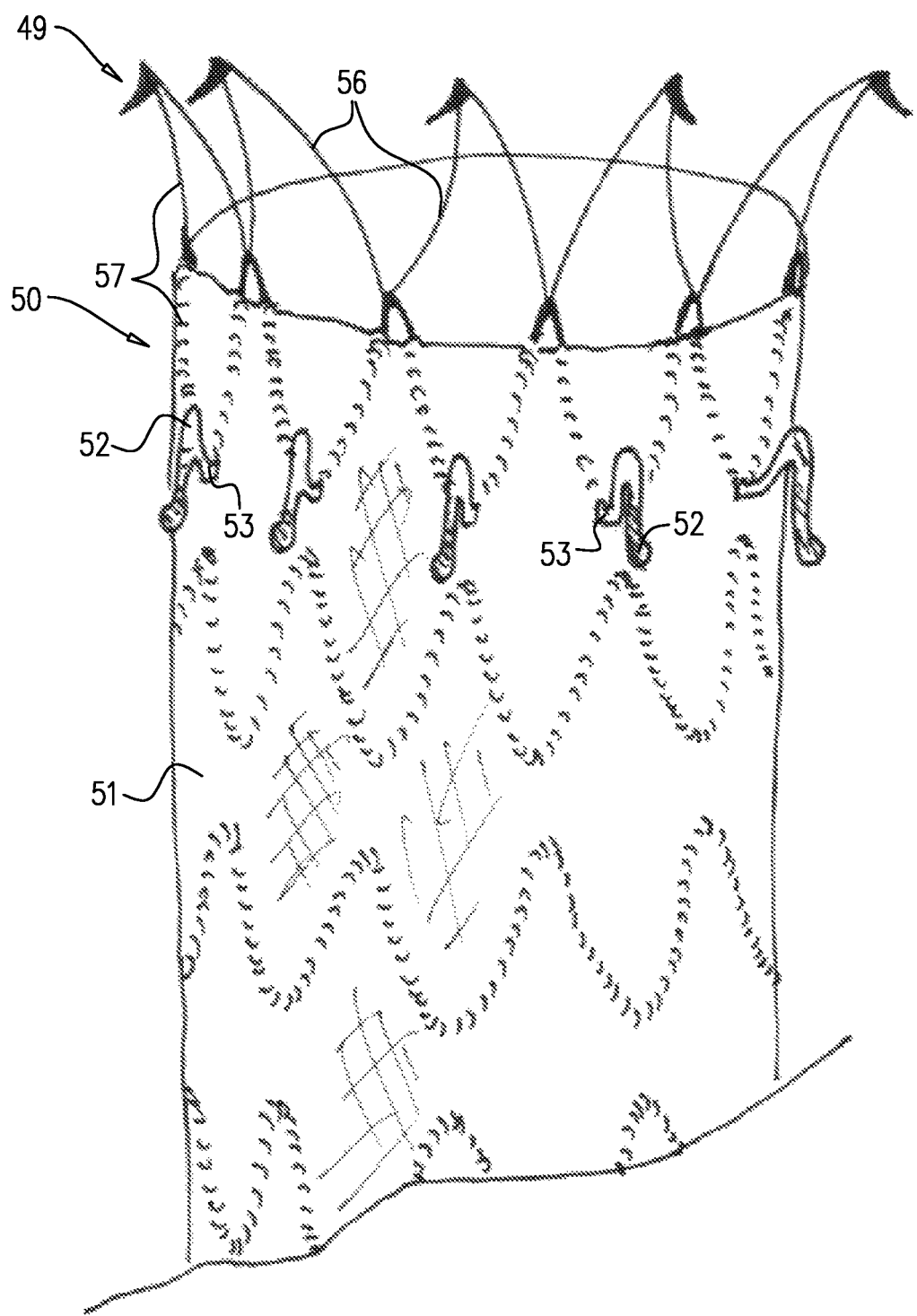

FIGS. 7A-C are schematic illustrations of an endovascular prosthesis 49 comprising a plurality of tissue engagement members 52, in accordance with respective applications of the present invention. Endovascular prosthesis 49 is configured to initially be positioned in a delivery catheter in a radially-compressed state, such as described hereinabove with reference to FIGS. 4A and 6A for stent-grafts 5 and 39, respectively, mutatis mutandis. Prosthesis 49 is configured to assume a radially-expanded state upon being deployed from the delivery catheter, such as described hereinabove with reference to FIGS. 4B-E and 6B-D for stent-grafts 5 and 39, respectively, mutatis mutandis. FIGS. 7A-C show the endovascular prosthesis in the radially-expanded state.

Endovascular prosthesis 49 comprises a structural member 50, a plurality of circumferentially disposed tissue engagement members 52, and a plurality of communicating members 53 that respectively connect structural member 50 to the tissue engagement members 52. For some applications, the prosthesis further comprises a fluid flow guide 51, similar to the fluid flow guides described hereinabove with reference to FIGS. 2 and 5A-B. Structural member 50 comprises a plurality of structural stent elements 57. For some applications, at least some of, e.g., all of, the structural stent elements are interconnected (as shown in the figures), while for other applications, a portion of, e.g., all of, the structural stent elements are not interconnected (configuration not shown). For some applications, a rostral-most first portion of structural stent elements 57 define a plurality of anchoring elements 56 that extend radially outwardly (and optionally rostrally or caudally) when the stent-graft assumes the radially-expanded state, as shown in FIGS. 7A-C. The anchoring elements immediately anchor the prosthesis to the vascular wall upon deployment, helping prevent dislodgement. Optionally, one or more of anchoring elements 56 are shaped so as to define respective barbs 71. A second portion of structural stent elements 57 define a stent body 74 when the stent-graft assumes the radially-expanded state. The second portion of members 57 are typically coupled to the first portion of members 57, and immediately caudal to the first portion. For some applications, structural member 50 comprises a metal. Alternatively or additionally, the structural member comprises a self-expanding material. Alternatively or additionally, the structural member comprises a super-elastic alloy, such as Nitinol.

Tissue engagement members 52 are disposed (typically, circumferentially) externally to stent body 74 when the prosthesis assumes the radially-expanded state. Communicating members 53 are generally radially-oriented when the prosthesis assumes the radially-expanded state. For example, when the prosthesis assumes the radially-expanded state, the communicating members may define an angle of between 20 and 90 degrees, such as between 50 and 70 degrees, with an external surface of stent body 74. Typically, the tissue engagement members are blunt, i.e., are not shaped so as to define any sharp elements that extend generally radially outward with respect to the stent body, such as spikes or barbs. As a result, the tissue engagement members cause low trauma to the wall of the aorta, and typically do not pierce the wall, thus allowing flexibility during deployment of the prosthesis. The tissue engagement members are typically heat-set to outwardly radially protrude, such that several weeks after placement of the prosthesis, the tissue engagement members become embedded in the wall of the aorta, thereby helping hold the prosthesis in place. The tissue engagement members typically have a larger surface area than conventional barbs, such as a surface area of at least 0.5 mm2, no more than 8 mm2, and/or between 0.5 and 8 mm2. Typically, each of the tissue engagement members extends in one or more directions generally parallel to a surface of stent body 74. Respective distances between the surface of stent body 74 and all locations of each of the tissue engagements members typically vary by less than 30%. For some applications, prosthesis 49 further comprises a plurality of connecting elements, which couple at least a portion of the tissue engagement members to respective adjacent ones of the tissue engagement members (configuration not shown).

For some applications, when the prosthesis assumes the radially-expanded state, a spring coefficient of each of the communicating members 53, measured during application of a radial force by a rigid circular disk, is at least 20% less than a spring coefficient of stent body 74, measured during application of the radial force by disk at a region around point on the stent body at which the communicating member is connected, wherein the disk has a radius equal to 50% of a radius of stent body at the point. This lesser spring coefficient may facilitate gradual penetration of the communicating members into adjacent vascular wall tissue, while allowing tight circumferential conformity between the stent body and the adjacent vascular wall tissue. For some applications, when the prosthesis assumes the radially-expanded state, the tissue engagement members radially protrude a distance of at least 1 mm, no more than 4 mm, and/or between 1 and 4 mm from the stent body.

In the configuration shown in FIG. 7A, tissue engagement members 52 are generally circumferentially arcuate and extend laterally around stent body 74. For some applications, the tissue engagement members are disposed as a circumferential and axial array around stent body 74.

In the configuration shown in FIG. 7B, tissue engagement members 52 are generally linear and extend axially along the stent body. For some applications, the tissue engagement members are arranged as an axial array along the stent body.

In the configuration shown in FIG. 7C, tissue engagement members 52 are polygonal, e.g., diamond-shaped, similar to the shape of standard stent closed cells.

Figure 8A:
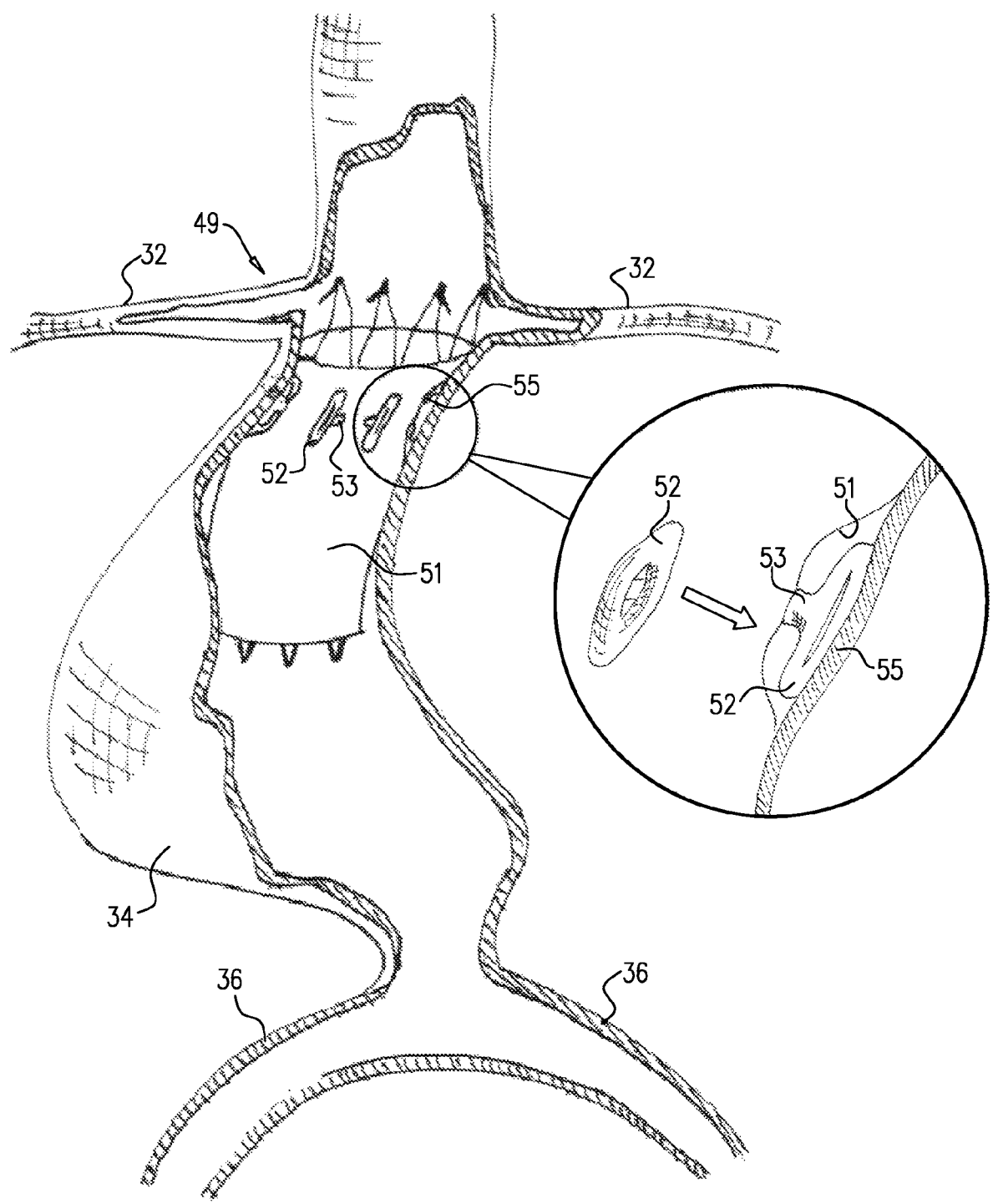
FIGS. 8A and 8B are schematic illustrations of the endovascular prosthesis of FIG. 7C, immediately following its deployment in the rostral portion of an aortic aneurysm and a few weeks following its deployment, respectively, in accordance with an application of the present invention.
Figure 8B:
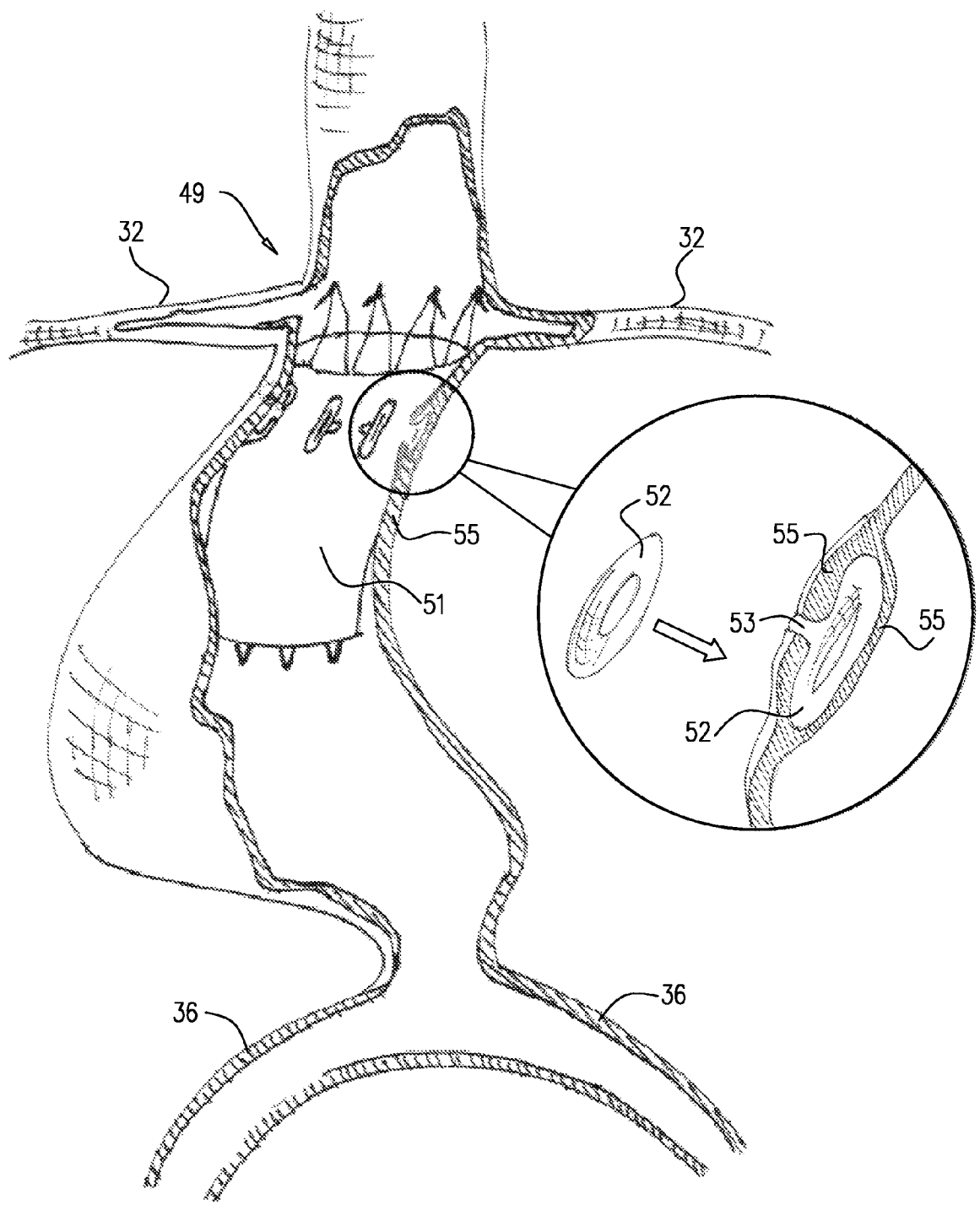

FIGS. 8A and 8B are schematic illustrations of endovascular prosthesis 49 with the configuration of FIG. 7C, immediately following its deployment in the rostral portion of aortic aneurysm 34 and a few weeks following its deployment, respectively, in accordance with an application of the present invention. Prosthesis 49 is typically transvascularly (typically percutaneously) introduced into the aorta using delivery tool 4, such as described hereinabove with reference to FIG. 4A, mutatis mutandis. In the state shown in FIG. 8A, tissue engagement member 52 is pressing against aortic wall 55, but not yet been incorporated into the aortic wall. In the state shown in FIG. 8B, the tissue engagement member and communicating member have been incorporated into aortic wall 55.

Doubly Flared Endovascular Stent-Graft

Figure 9A:
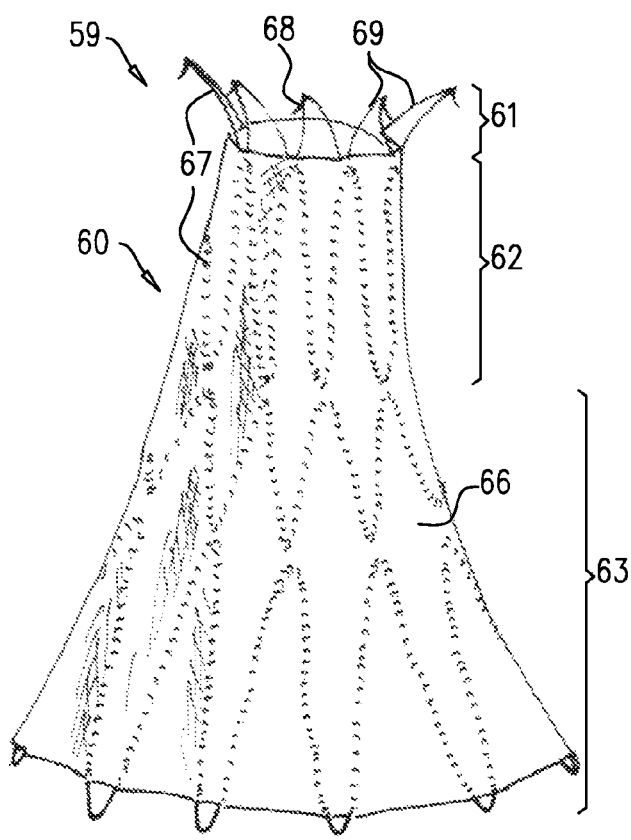
FIGS. 9A-B are schematic illustrations of a doubly-flared endovascular stent-graft prosthesis, in accordance with an application of the present invention.
Figure 9B:
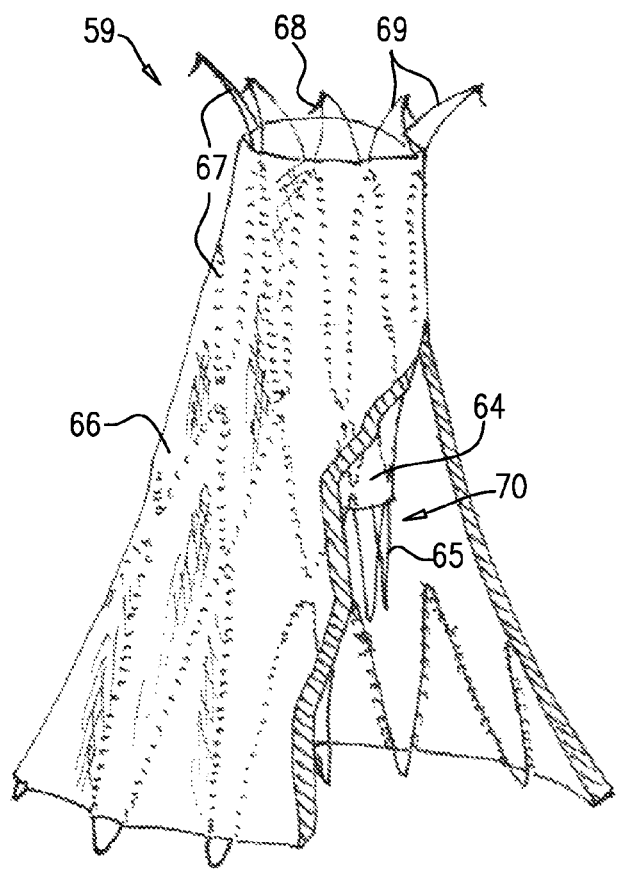

FIGS. 9A-B are schematic illustrations of a doubly-flared endovascular stent-graft prosthesis 59, in accordance with an application of the present invention. Endovascular prosthesis 59 is configured to initially be positioned in a delivery catheter in a radially-compressed state, such as described hereinabove with reference to FIGS. 4A and 6A for stent-grafts 5 and 39, respectively, mutatis mutandis. Prosthesis 59 is configured to assume a radially-expanded state upon being deployed from the delivery catheter, such as described hereinabove with reference to FIGS. 4B-E and 6B-D for stent-grafts 5 and 39, respectively, mutatis mutandis. FIGS. 9A-B show the endovascular prosthesis in the radially-expanded state.

Endovascular prosthesis 59 comprises a structural member 60. When the prosthesis assumes the radially-expanded state, structural member 60 is shaped so as to define:
- a flared rostral portion 61, which flares radially outward in a rostral direction (i.e., a cross-sectional area of portion 61 increases as one moves in the rostral direction);
- a flared caudal portion 63, which flares radially outward in a caudal direction (i.e., a cross-sectional area of portion 63 increases as one moves in the caudal direction); and
- optionally, a generally constant-diameter body portion 62, which is disposed longitudinally between the flared rostral and caudal portions, and has a diameter that varies by less than 15% along an entire length thereof, such as by less than 10%.

For some applications, structural member 60 comprises a plurality of structural stent elements 67. For some applications, at least some of, e.g., all of, the structural stent elements are interconnected (as shown in the figures), while for other applications, at least a portion of, e.g., all of, the structural stent elements are not interconnected (configuration not shown). For some applications, flared rostral portion 61 comprises a plurality of anchoring elements 69 that extend radially outwardly (and optionally rostrally or caudally) when the prosthesis assumes the radially-expanded state, as shown in FIGS. 9A-B. The anchoring elements help anchor the prosthesis to the vascular wall upon deployment, helping prevent dislodgement. Optionally, one or more of anchoring elements 69 are shaped so as to define respective barbs 68. For some applications, structural member 60 comprises a metal. Alternatively or additionally, the structural member comprises a self-expanding material. Alternatively or additionally, the structural member comprises a super-elastic alloy, such as Nitinol. For some applications, the structural member is woven or braided.

For some applications, a spring coefficient of flared caudal portion 63, measured during application of a radial force by a rigid circular disk at a region centered at a first point on the flared caudal portion that is furthest from a central longitudinal axis of the prosthesis, is (a) at least 20% less than a spring coefficient of body portion 62, measured during application of the radial force by the disk at a region centered at a second point on the body portion that is furthest from the axis of the prosthesis, and/or (b) at least 20% less than a spring coefficient of flared rostral portion 61, measured during application of the radial force by the disk at a region centered at a third point on the flared rostral portion that is furthest from the axis of the prosthesis, wherein the circular disk has a radius equal to 50% of a radius of the prosthesis at the first point. The low spring coefficient helps flared caudal portion 63 to maintain a tight seal with the wall of the aorta, thereby preventing current or future type I endoleaks. At the same time, flared caudal portion is configured to apply a radially-outward force that is sufficient to expand with the aortic wall, but insufficient to itself cause expansion of the aortic wall.

For some applications, the prosthesis further comprises a fluid flow guide 66, which comprises at least one biologically-compatible substantially fluid-impervious flexible sheet, such as described hereinabove with reference to FIGS. 2 and 5A-B. The fluid flow guide is coupled to at least body portion 62, and additionally to at least a portion of flared caudal portion 63. The portion of the fluid flow guide coupled to body portion 62 serves to define a lumen for blood flow. The portion of the fluid flow guide coupled to flared caudal portion 63 seals the prosthesis against the aortic wall. This latter portion does not necessarily define the lumen, such as for applications in which the prosthesis comprises stent-engagement member 70, as described hereinbelow with reference to FIG. 9B; for these applications, the lumen defined by the portion of the fluid flow guide coupled to body portion 62 is in fluid communication with the lumen defined by the stent-engagement member, and the portion of the fluid flow guide coupled to flared caudal portion 63 provides sealing with the aortic wall rather than fluid flow guiding. For some applications, a caudal end of the fluid flow guide is disposed within 4 cm of, at least 1 cm from, and/or between 1 and 4 cm of a caudal end of the structural member.

For some applications, an axial length of flared caudal portion 63 varies around a circumference of the flared caudal portion. In other words, the caudal end of the flared caudal portion is curved, such that if the prosthesis were to be placed on a flat surface, only a portion of the caudal end would touch the surface. For some applications, flared caudal portion 63 is externally concave (i.e., concave when viewed from outside of the prosthesis), as shown in the figures; for other applications, the flared caudal portion is externally convex (configuration not shown). For some applications, the flared caudal portion includes a rostral sub-portion that is externally concave, and a more caudal sub-portion that is externally convex.

For some applications, as can be seen in the cutout of FIG. 9B, prosthesis 59 further comprises a stent-engagement member 70, which, when the prosthesis assumes the radially-expanded state, is generally tubular. Stent-engagement member 70 is configured to be sealingly coupled to a primary stent-graft, as described hereinbelow with reference to FIG. 9D. Stent-engagement member 70 is disposed at least partially within at least one portion selected from the group consisting of: flared caudal portion 63, and body portion 62. Typically, the prosthesis further comprises a biologically-compatible substantially fluid-impervious flexible sheet 64, which at least partially covers the stent-engagement member. For some applications, stent-engagement member 70 comprises a scaffold 65, which is shown in FIG. 9B partially protruding in a caudal direction from flexible sheet 64. For some applications, the scaffold comprises a self-expanding material, and/or a super-elastic alloy, such as Nitinol. For some applications, scaffold 65 is constructed as a caudal continuation of body portion 62.

Figure 9C:
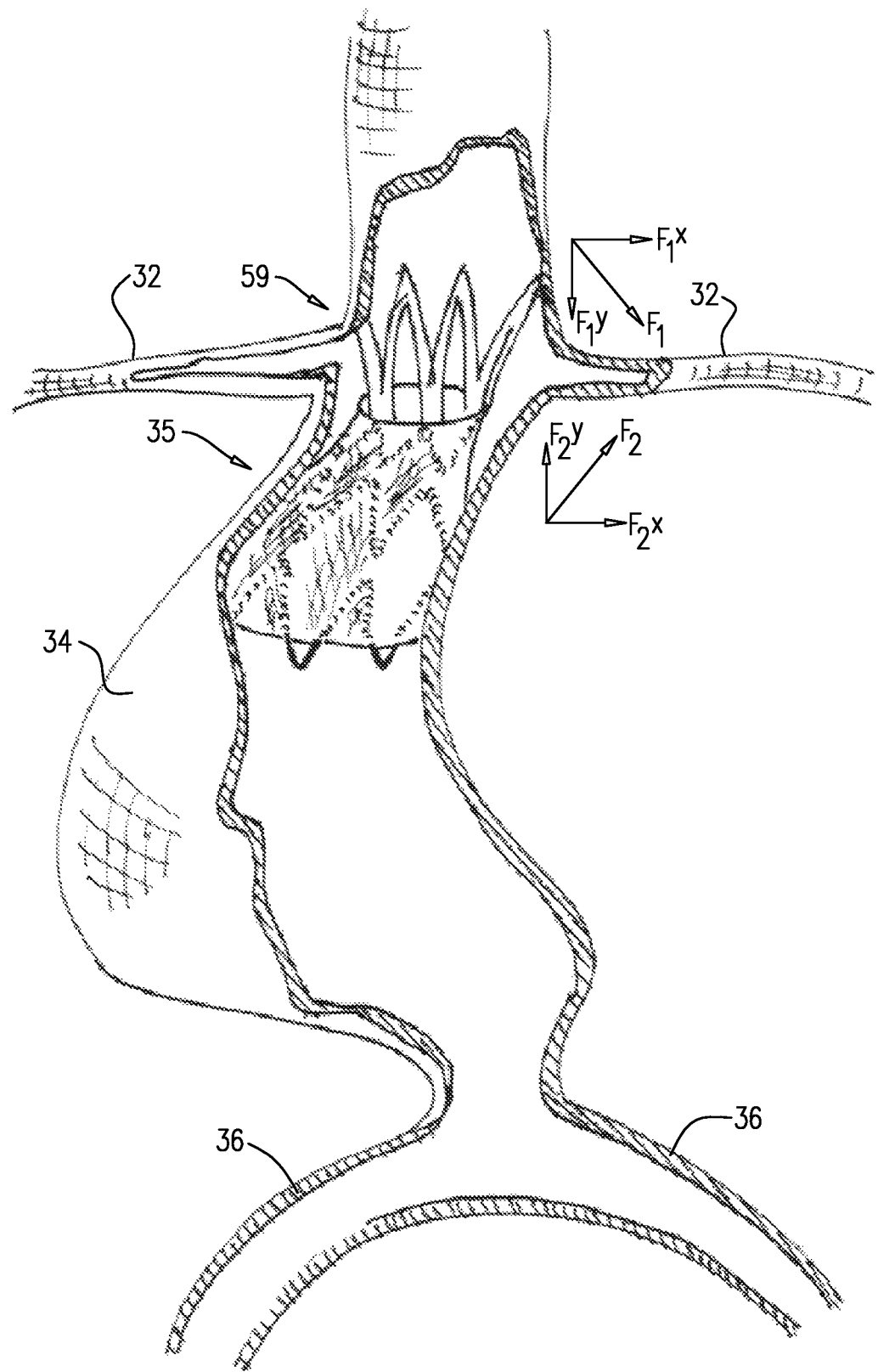
FIGS. 9C and 9D are schematic illustrations of the prosthesis of FIGS. 9A-B deployed in the vicinity of the renal arteries, in accordance with respective applications of the present invention.
Figure 9D:
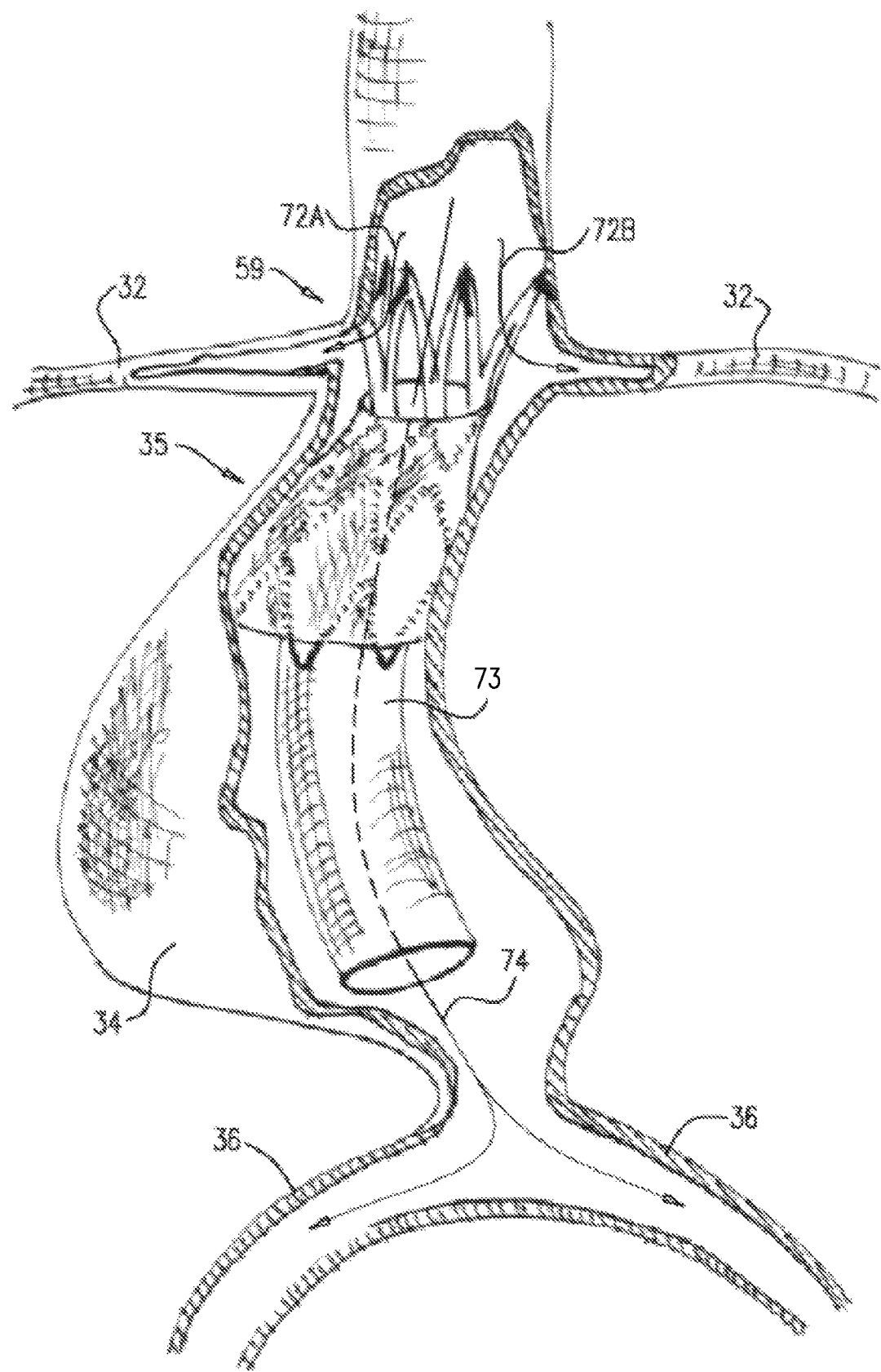

FIGS. 9C and 9D are schematic illustrations of prosthesis 59 deployed in the vicinity of renal arteries 32, in accordance with respective applications of the present invention. Prosthesis 59 is typically transvascularly (typically percutaneously) introduced into the aorta using delivery tool 4, such as described hereinabove with reference to FIG. 4A, mutatis mutandis. The prosthesis is positioned such that (a) flared caudal portion 63 is disposed in rostral end 35 of abdominal aortic aneurysm 34, caudal to both anastomoses of the renal arteries, (b) flared rostral portion 61 is disposed rostral to both of the anastomoses of the renal arteries, and (c) body portion 62, if provided, spans both the anastomoses of the renal arteries. The flare of the caudal portion seals the prosthesis to the rostral end of the aneurysm, thereby reducing a current or future risk for type I endoleak.

Prosthesis 59 is typically held in place at least by the combination of the following forces: (a) the radially outward force of anchoring elements 69, and (b) forces applied by flared rostral portion 61 and flared caudal portion 63. Flared caudal portion 63 exerts a force against the wall of the aorta, labeled in FIG. 9C as force vector $F_2$. Force vector $F_2$ has both vertical and horizontal components $F_2y$ and $F_2x$. Similarly, flared rostral portion 61, such as anchoring elements 69 thereof, exert a force against the wall of the aorta, labeled as force vector $F_1$. Force vector $F_1$ has both vertical and horizontal components $F_1y$ and $F_1x$. The vertical force components $F_1y$ and $F_2y$ are directed towards one another, so as to axially pinch the aortic wall between the neck of the aneurysm and the rostral end of the aneurysm, thereby enhancing the anchoring of the stent-graft to the wall of the aorta, and reducing the likelihood of loosening of the prosthesis which may result in a type I endoleak.

For some applications, a kit is provided that comprises a plurality of prostheses 59 having different dimensions. One of the prostheses is selected that has a diameter of the body portion that is at least 15% less than a diameter of the aorta between the renal arteries, and has a diameter of a caudal end of the structural member that is at least 20% larger than a diameter of the aorta immediately caudal to a more caudal one of the renal arteries.

Reference is again made to FIG. 9D, which additionally shows a tubular primary stent-graft 73, a rostral end of which is sealingly coupled to stent-engagement member 70 (not visible in FIG. 9D; see FIG. 9B). Typically, primary stent-graft 73 has a diameter is that 10-15% greater than that of the caudal end of stent-engagement member 70. When the primary stent-graft is inserted into the stent-engagement member, and transitioned to a radially-expanded state, the outward radial pressure applied by the primary stent-graft against the inside of the stent-engagement member sealingly couples the primary stent-graft to the stent-engagement member. Primary stent-graft 73 provides a fluid-impervious channel to both iliac arteries 36 (for clarity of illustration, primary stent-graft 73 is not shown extending all the way to iliac arteries 36; in actual practice, the primary stent-graft does extend to the iliac arteries). Aortic blood flow is schematically indicated by an arrow 74, while two arrows schematically indicate blood flowing externally to the prosthesis and into the right and left renal arteries, respectively. For some applications, primary stent-graft 73 includes a uni-lumen rostral end and bifurcated caudal end, which is configured to be deployed in both iliac arteries.

Barbed Self-Expanding Lumen-Engagement Member

Figure 10A:
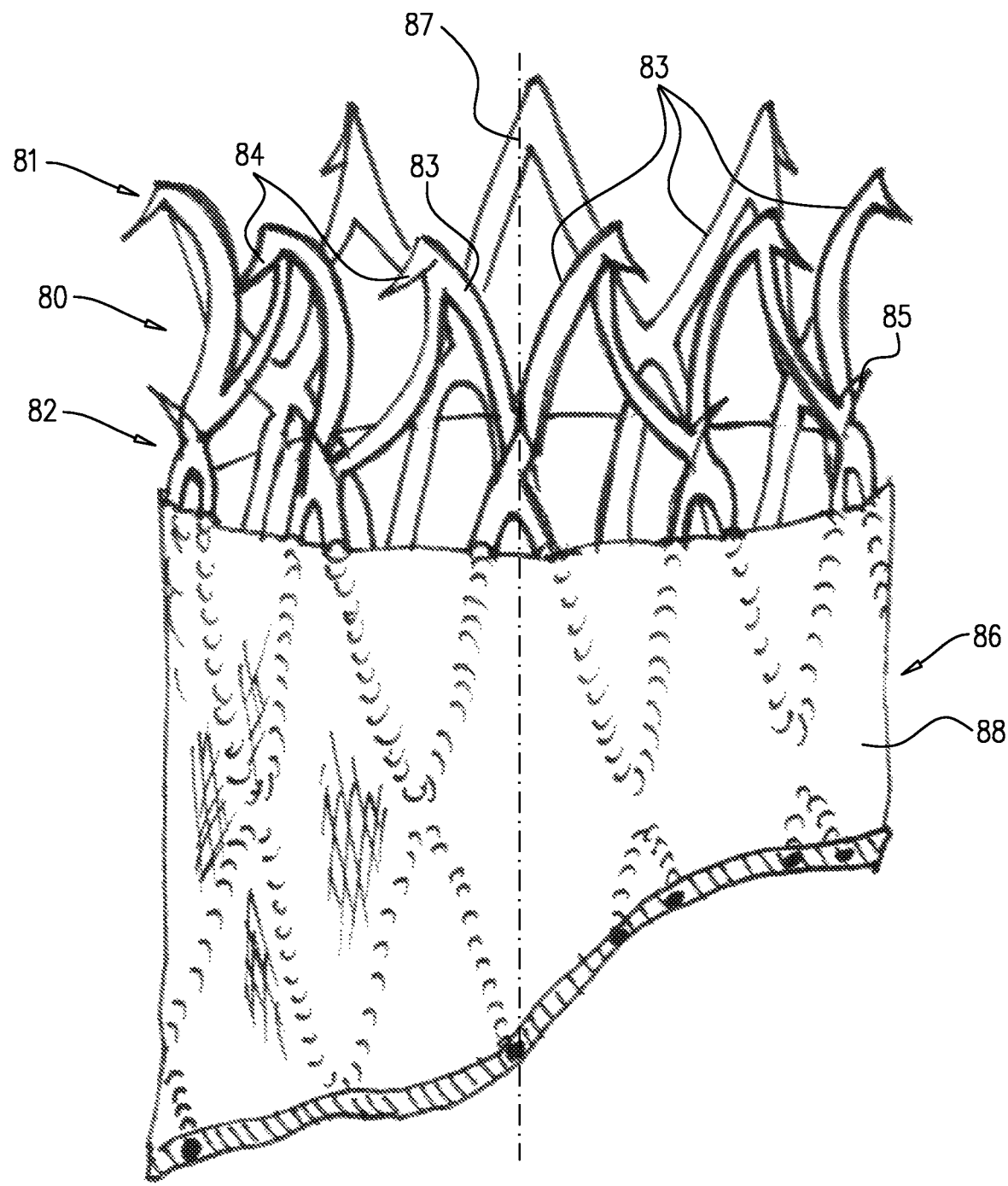
FIGS. 10A-B are schematic illustrations of a self-expanding lumen-engagement prosthesis member, in accordance with respective applications of the present invention.
Figure 10B:
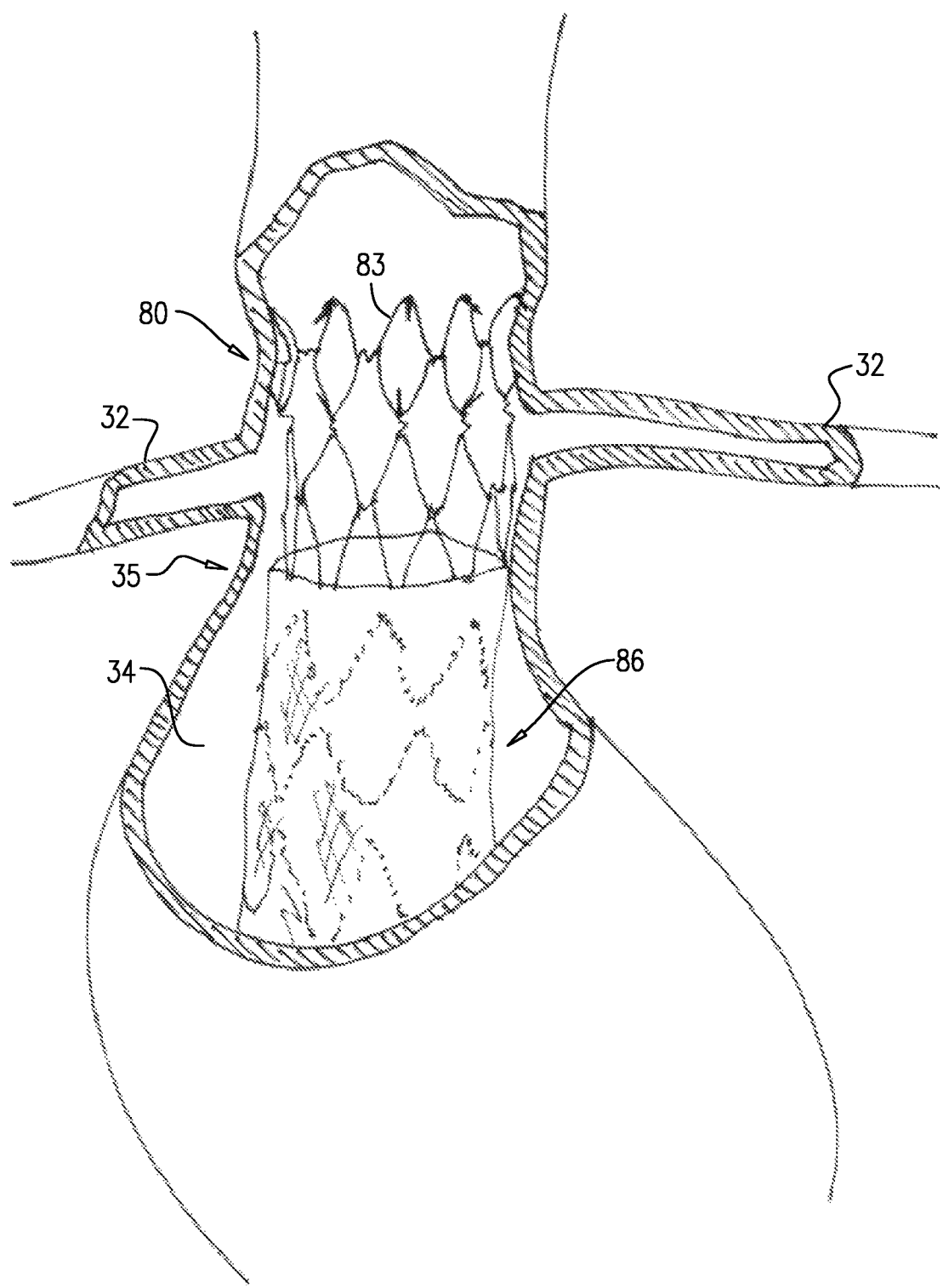

FIGS. 10A-B are schematic illustrations of a self-expanding lumen-engagement prosthesis member 80, in accordance with respective applications of the present invention. Prosthesis member 80 is configured to initially be positioned in a delivery catheter in a radially-compressed state, such as described hereinabove with reference to FIGS. 4A and 6A for stent-grafts 5 and 39, respectively, mutatis mutandis. Prosthesis member 80 is configured to assume a radially-expanded state upon being deployed from the delivery catheter, such as described hereinabove with reference to FIGS. 4B-E and 6B-D for stent-grafts 5 and 39, respectively, mutatis mutandis. FIGS. 10A-B show the prosthesis member in the radially-expanded state.

When prosthesis member 80 assumes the radially-expanded state, the prosthesis member is generally tubular, and defines a central longitudinal axis 87. The prosthesis member comprises a plurality of support members 83 distributed around a circumference of the prosthesis member, which are shaped so as to define respective curves having concavities that face radially outward. The support members have respective rostral and caudal ends 81 and 82. Prosthesis member 80 further comprises a plurality of rostral barbs 84 and a plurality of caudal barbs 85, disposed more caudally than the rostral barbs. When the prosthesis member assumes the radially-expanded state, rostral barbs 84 extend caudally and radially outwardly from respective ones of support members 83, and caudal barbs 85 extend rostrally and radially outward from respective ones of the support members. The rostral barbs are typically only slightly caudally oriented, such as at an angle of between 60 and 85 degrees with respect to the longitudinal axis, such as between 50 and 70 degrees, and the caudal barbs are typically only slightly rostrally oriented, such as at an angle of between 60 and 85 degrees with respect to the longitudinal axis, such as between 50 and 70 degrees. Typically, rostral and caudal barbs 84 and 85 are disposed at rostral and caudal ends 81 and 82 of support members 83, respectively. For some applications, prosthesis member 80 comprises an equal number of rostral and caudal barbs.

The oppositely-oriented rostral and caudal barbs axially pinch tissue of the aorta between the barbs, thereby anchoring prosthesis member 80 to the aorta. The concavity of the support members generally increases the axial forces applied by the barbs. For some applications, prosthesis member 80 is configured to longitudinally shorten as prosthesis member 80 transitions from the radially-compressed state to the radially-expanded state, thereby bringing rostral and caudal ends 81 and 82 of the support members 83 closer to each other, as an average diameter of the structural member increases.

For some applications, prosthesis member 80 is mounted at a rostral end of an endovascular stent-graft 86. For some applications, stent-graft 86 comprises a fluid flow guide 88, which comprises at least one biologically-compatible substantially fluid-impervious flexible sheet. For some applications, prosthesis member 80 is an element of an endovascular stent-graft system, configured to endoluminally treat an aortic aneurysm, such as one of the endovascular stent-graft systems described herein.

For some applications, the structural member comprises a metal. Alternatively or additionally, the structural member comprises self-expanding material, and/or a super-elastic alloy, such as Nitinol. Alternatively or additionally, the structural member comprises a braided or a woven material.

FIG. 10B shows prosthesis member 80 implanted in an aorta, mounted at a rostral end of endovascular stent-graft 86. In order to implant the prosthesis member, the prosthesis member is transvascularly (typically percutaneously) introduced into the aorta via one of iliac arteries 36, while the prosthesis member is positioned in a delivery catheter in the radially-compressed state. The prosthesis member is transitioned to the radially-expanded state by deploying the prosthesis member from the delivery catheter in the aorta within 2 cm of, at least 0.5 from, and/or between 0.5 and 2 cm of renal arteries 32, such that the prosthesis member engages the aortic wall. For some applications, as shown in FIG. 10B, prosthesis member 80 is disposed rostrally to renal arteries 32, while for other application (not shown), the prosthesis member is disposed caudally to the renal arteries. The prosthesis member is typically sized such that a diameter of structural member 83 when the prosthesis member assumes the radially-expanded state is greater than a diameter of the aorta at sites at which the prosthetic member engages the aortic wall. Typically, endovascular stent-graft 86 is positioned so as to engage and seal rostral end 35 of aneurysm 34.

Endovascular Stent-Graft Having Two Rostral Elongated Indentations

Figure 11A:
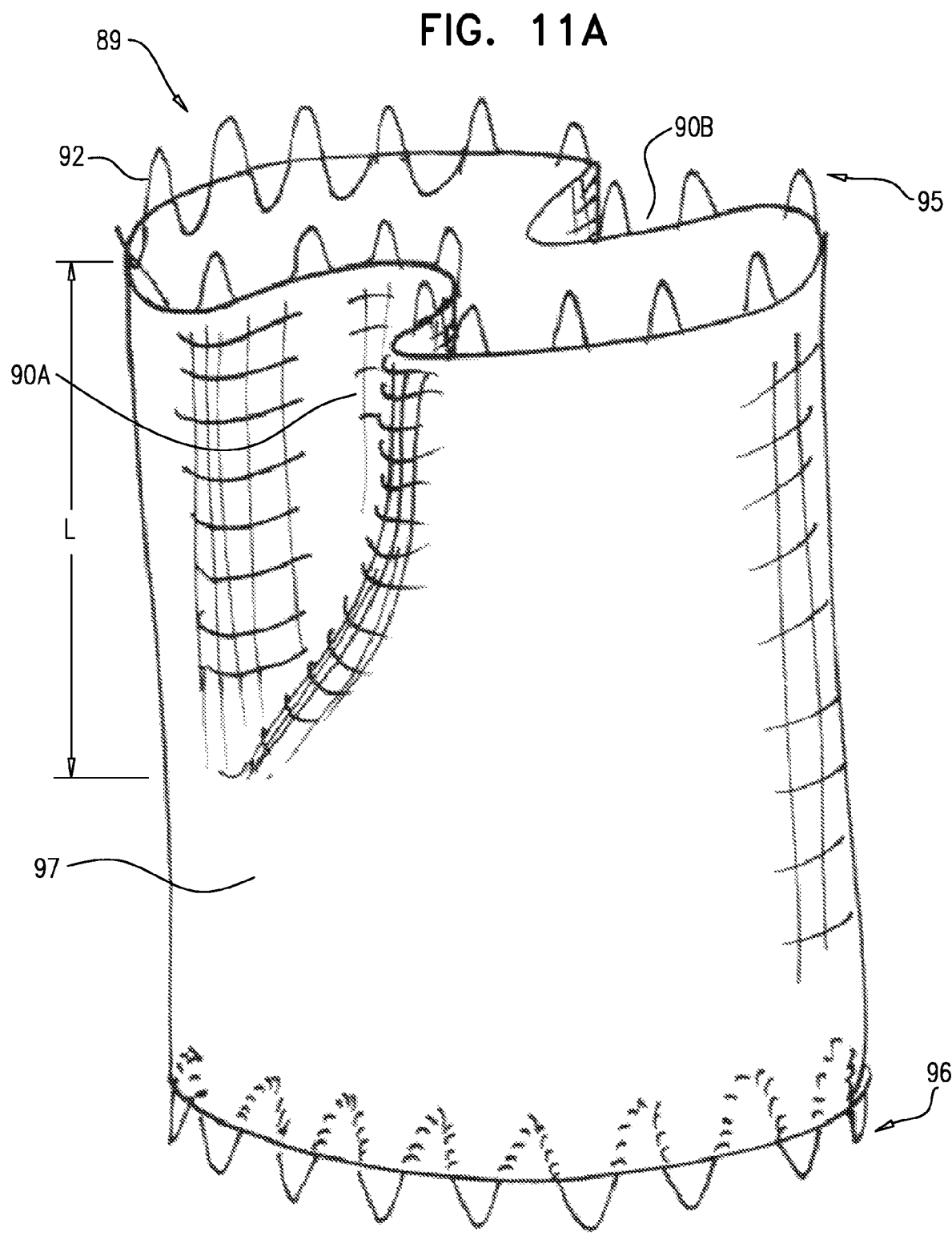
FIGS. 11A-C are schematic illustrations of a self-expandable endovascular sealing stent-graft, in accordance with an application of the present invention.
Figure 11B:
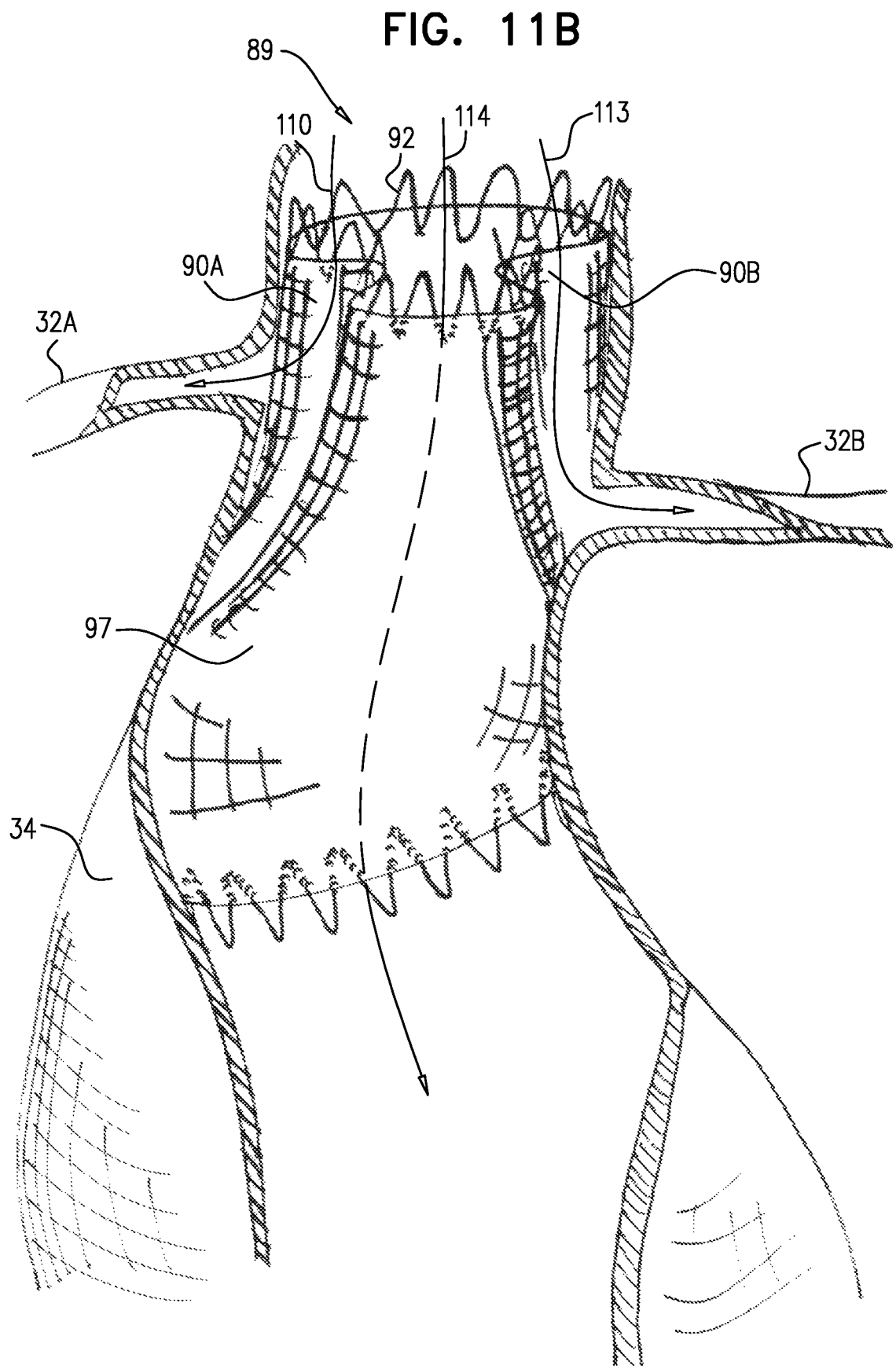
Figure 11C:
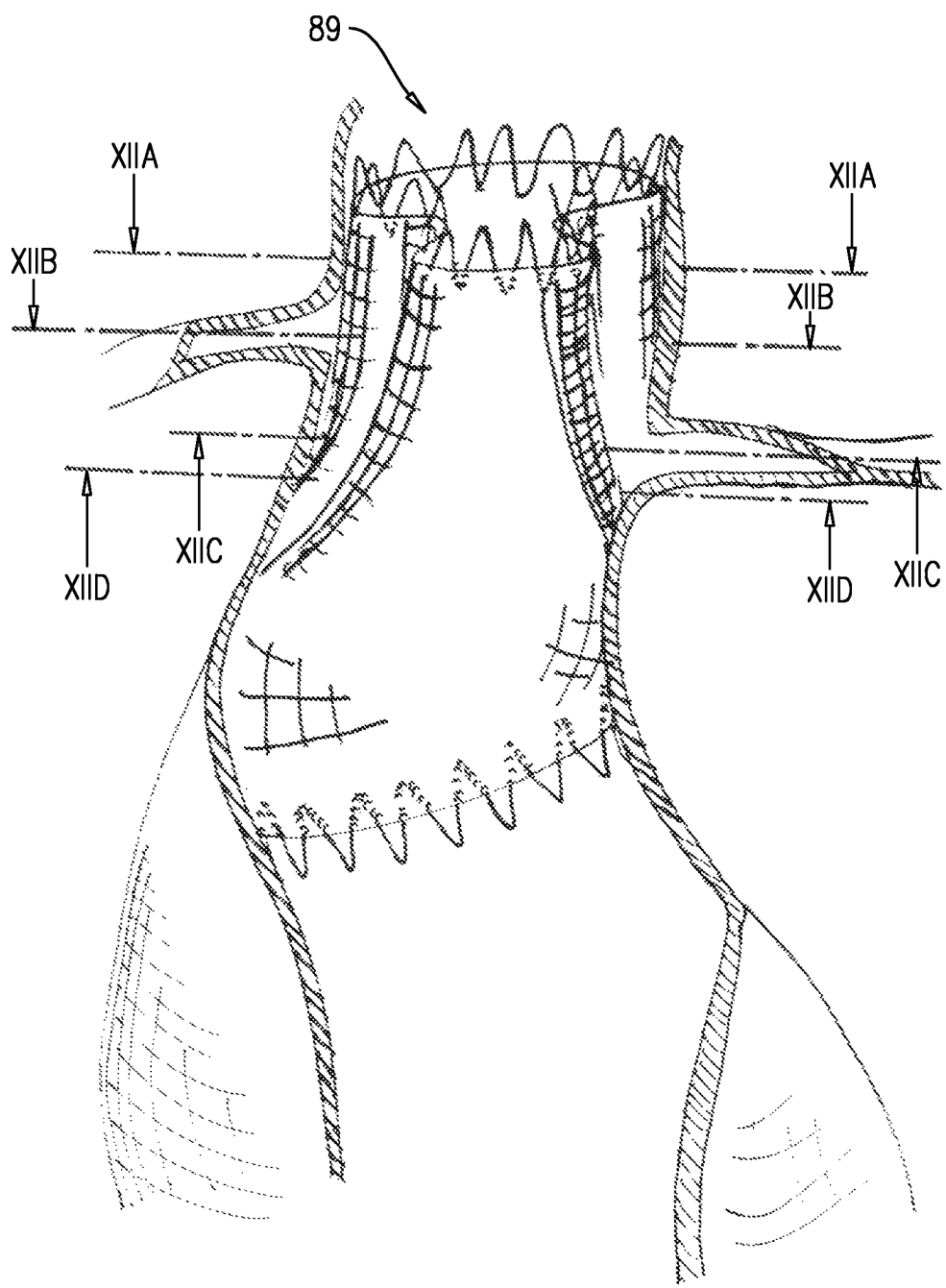

FIGS. 11A-C are schematic illustrations of a self-expandable endovascular sealing stent-graft 89, in accordance with an application of the present invention. Endovascular stent-graft 89 is configured to initially be positioned in a delivery catheter in a radially-compressed state, such as described hereinabove with reference to FIGS. 4A and 6A for stent-grafts 5 and 39, respectively, mutatis mutandis. Stent-graft 89 is configured to assume a radially-expanded state upon being deployed from the delivery catheter, such as described hereinabove with reference to FIGS. 4B-E and 6B-D for stent-grafts 5 and 39, respectively, mutatis mutandis. FIGS. 11A-12D show the endovascular stent-graft in the radially-expanded state.

Endovascular stent-graft 89 comprises a structural member 92, which extends along the entire axial length of the stent-graft, and a fluid flow guide 97, which is coupled to at least a portion of structural member. Typically, structural member 92 comprises a plurality of structural stent elements. For some applications, at least some of, e.g., all of, the structural stent elements are interconnected (as shown in the figures), while for other applications, at least a portion of, e.g., all of, the structural stent elements are not interconnected (configuration not shown). For some applications, a diameter of the structural member is between 2.5 and 3 cm, when the stent-graft assumes the radially-expanded state. For some applications, an axial length of the structural member is between 4 and 10 cm, such as between 4 and 7 cm, when the stent-graft assumes the radially-expanded state.

For some applications, stent-graft 89 further comprises a plurality of anchoring elements, which are generally radially oriented when the stent-graft assumes the radially-expanded state (configuration not shown). For example the anchoring elements may be similar to anchoring element 7, described hereinabove with reference to FIGS. 1 and 2, or tissue engagement members 52, described hereinabove with reference to FIGS. 7A-C.

Fluid flow guide 97 comprises at least one biologically-compatible substantially fluid-impervious flexible sheet, which is coupled to structural member 92, either outside or within the structural member, such as by stitching, and covers either an external or an internal surface of at least a portion of the structural member, in order to define a fluid flow path through the structural member. The flexible sheet may comprise, for example, a polymeric material (e.g., polytetrafluoroethylene), a textile material (e.g., polyethylene terephthalate (PET)), natural tissue (e.g., saphenous vein or collagen), or a combination thereof. For some applications, a rostral end of the fluid flow guide is disposed within 4 cm of, at least 1 cm from, and/or between 1 and 4 cm of a rostral end 95 of the structural member. For some applications, a caudal end of the fluid flow guide is disposed within 2 cm of, at least 0.5 cm from, and/or between 0.5 and 2 cm of a caudal end 96 of the structural member.

As can be seen in FIGS. 11A-C, structural member 92 has a generally tubular shape, e.g., a generally cylindrical shape. The structural member is shaped so as to define at least two elongated indentations 90A and 90B, each of which extends rostrally to rostral end 95 of structural member 92, and is tapered in a caudal direction until the indentation converges with the generally tubular shape of structural member 92. Fluid flow guide 97 covers at least a portion of each of the elongated indentations. Elongated indentations 90A and 90B serve to direct blood flow toward the renal arteries. Structural member 92 typically provides an outwardly-directed radial force against the aorta other than at the elongated indentations. The outwardly-directed radial force is typically provided by:

a portion of the structural member rostral to the renal arteries;

a portion of the structural member at the same height as the renal arteries, but at radial directions other than the elongated indentations; and a portion of the structural member caudal to the renal arteries.

The outwardly-directed force serves to anchor the stent-graft in the aorta and/or to push the fluid flow guide sealingly against the aorta, thereby preventing current or future type I endoleaks.

Typically, each of the elongated indentations has an axial length L of at least 2 cm, no more than 4 cm, and/or between 2 and 4 cm, when the stent-graft assumes the radially-expanded state. For some applications, the structural member comprises a metal. Alternatively or additionally, the structural member comprises a self-expanding material. Alternatively or additionally, the structural member comprises a super-elastic alloy, such as Nitinol.

FIGS. 11B-C are schematic illustrations of stent-graft 89 positioned caudal to aortic aneurysm 34 in a vicinity of right and left renal arteries 32A and 32B. The stent-graft is percutaneously and endovascularly introduced into the aorta, via one of iliac arteries, into a vicinity of renal arteries 32A and 32B, while positioned in a delivery catheter in the radially-compressed state. The stent-graft is transitioned to the radially-expanded state by deploying the stent-graft from the delivery catheter in the aorta, such that two of elongated indentations 90A and 90B are radially aligned with renal arteries 32A and 32B, respectively, with rostral ends of the elongated indentations rostral to the renal arteries, respectively, and caudal ends of the elongated indentations caudal to the renal arteries, respectively. To enable this proper rotational orientation, the stent-graft may comprise, for example, one or more radiopaque markers, such as exactly one radiopaque marker that the physician rotationally aligns with a predetermined anatomical feature. Alternatively or additionally, one or more radiopaque markers are coupled to the delivery catheter, or another portion of the delivery tool.

For some applications, the stent-graft is provided in a kit as one of a plurality of stent-grafts having different, respective angles of offset between two of the elongated indentations (as described hereinbelow with reference to FIG. 12B). In order to select the most appropriate stent-graft from the kit, the physician assesses an angle between renal arteries 32A and 32B, and selects one of the stent-grafts having an angle of offset closest to the assessed angle between the renal arteries. For example, the physician may assess the angel using a three-dimensional reconstruction of a CT angiography or MRA image.

Reference is again made to FIG. 11B. Flow indication arrows 110 and 113 schematically indicate blood flow into right and left renal arteries 32A and 32B, respectively, via right and left elongated indentations 90A and 90B, respectively. A flow indication arrow 114 schematically indicates blood flow through the lumen of stent-graft 89.

FIGS. 12A-D are four schematic axial cross-sections of stent-graft 89 in the abdominal aorta in a vicinity of renal arteries 32A and 32B, in accordance with an application of the present invention. The cross-sections correspond to the planes labeled in FIG. 11C. Right elongated indentation 90A is shown disposed generally opposing left elongated indentation 90B. Section XIIA-XIIA (FIG. 12A) is an axial cross-section of the stent-graft rostral to both renal arteries 32A and 32B. Section XIIB-XIIB (FIG. 12B) is an axial cross-section of the stent-graft at the level of right renal artery 32A, which is shown to be fed blood via right elongated indentation 90A. Section XIIC-XIIC is an axial cross-section of the stent-graft at the level of left renal artery 32B, which is shown to be fed blood via left elongated indentation 90B. Section XIID-XIID is an axial cross-section of the stent-graft at a level caudal to both renal arteries 32A and 32B.

Figure 12A:
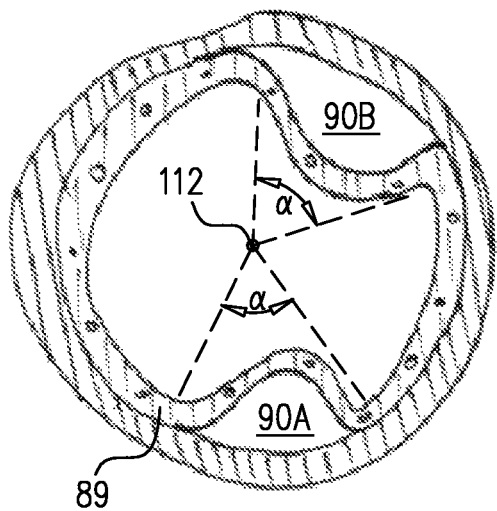
FIGS. 12A-D are four schematic axial cross-sections of the stent-graft of FIGS. 11A-C in the abdominal aorta in a vicinity of the renal arteries, in accordance with an application of the present invention.
Figure 12B:
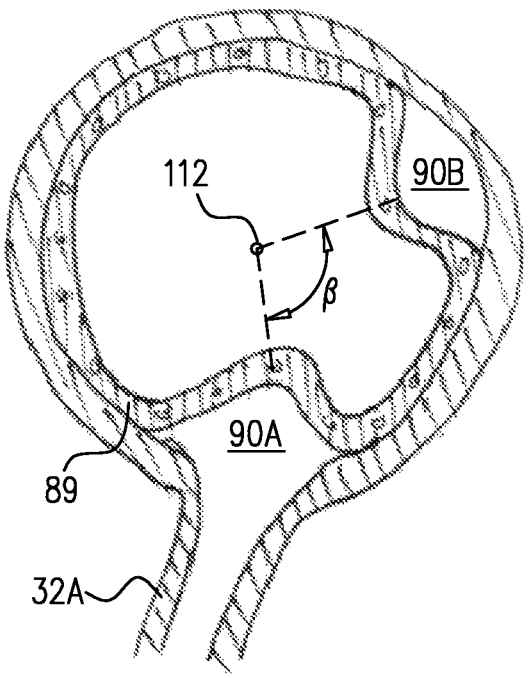
Figure 12C:
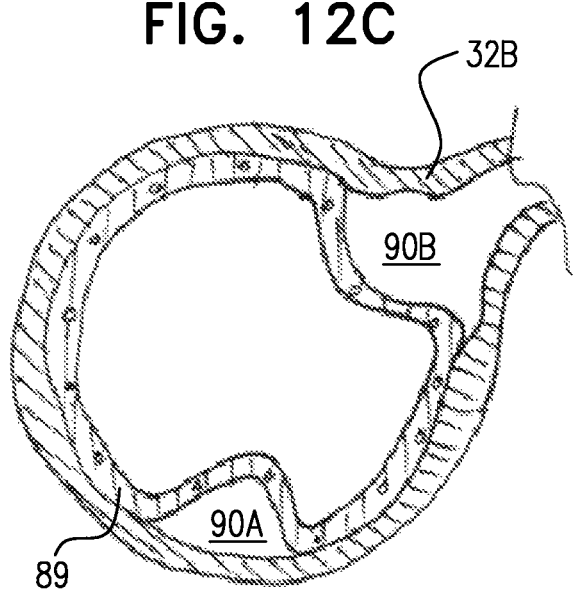
Figure 12D:
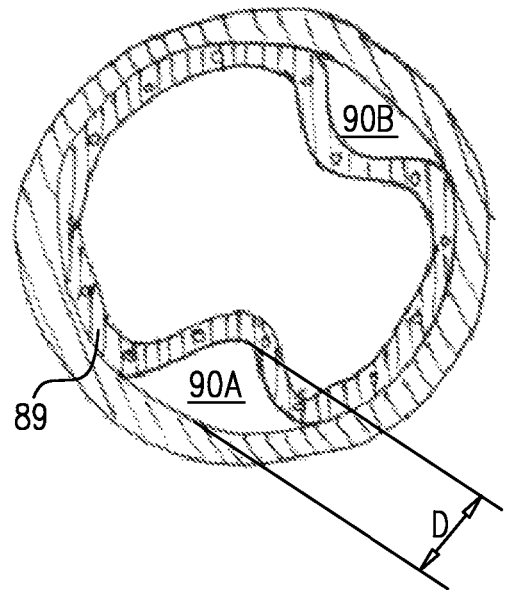

Typically, a rostral end of each of the elongated indentations spans an arc a (alpha) of between 10 and 40 degrees, such as 15 degrees, as indicated in FIG. 12A, when stent-graft 89 assumes the radially-expanded state. Typically, when the stent-graft assumes the radially-expanded state, centers of two of the elongated indentations 90A and 90B are offset by an angle β (beta) of between 70 and 220 degrees, such as between 150 and 170 degrees, e.g., 160 degrees, as measured with respect to a central longitudinal axis 112 of the structural member, as indicated in FIG. 12B. Typically, when the stent-graft assumes the radially-expanded state, a rostral end of each of the elongated indentations is indented a distance D of between 0.5 and 1 cm from the generally tubular shape of the structural member, as indicated in FIG. 12D. (It is noted that although FIG. 12D does not actually show the rostral end of the elongated indentations, the indicated method of measuring distance D applies equally well the rostral end.)

Unilumen Endovascular Stent-Graft

Figure 13:
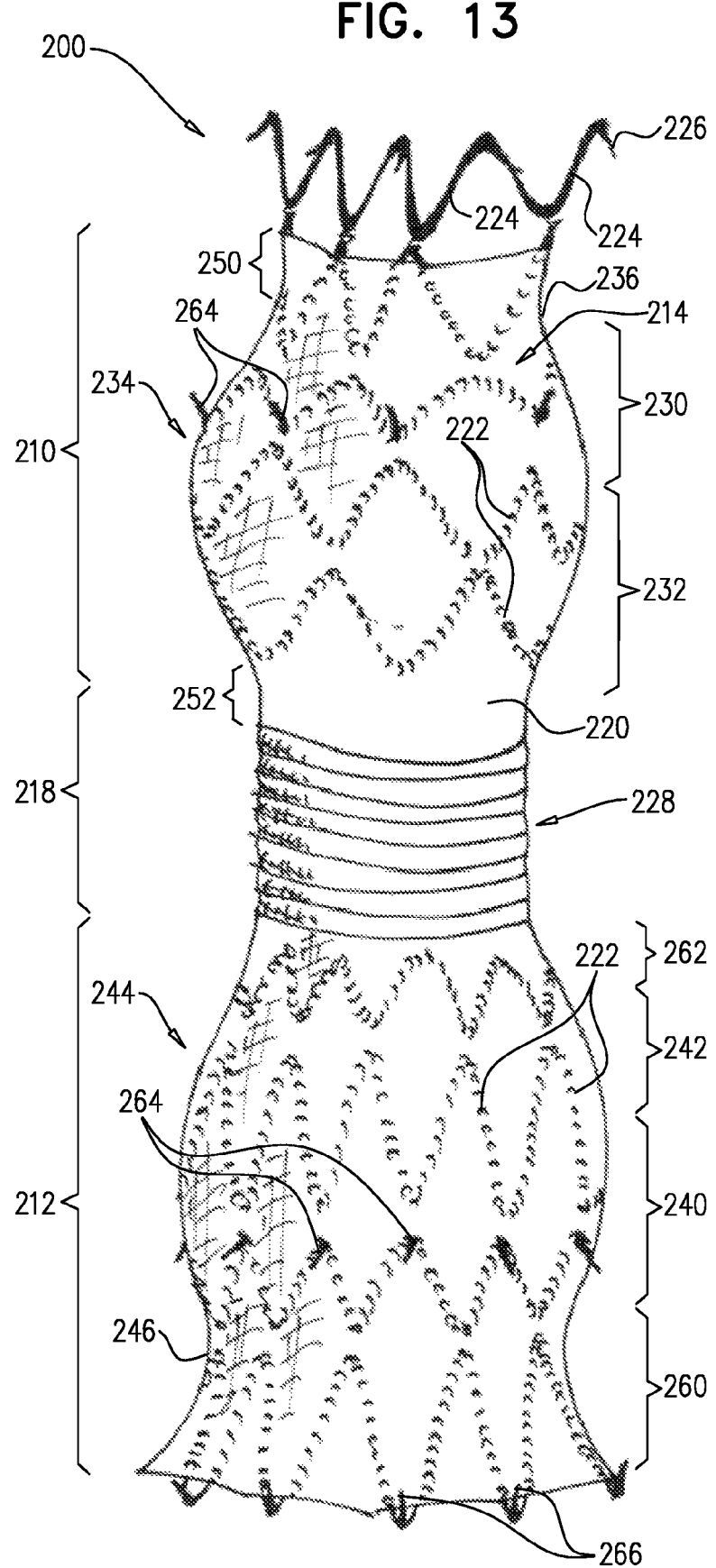
FIG. 13 is a schematic illustration of a unilumen endovascular stent-graft, in accordance with an application of the present invention.
Figure 14A:
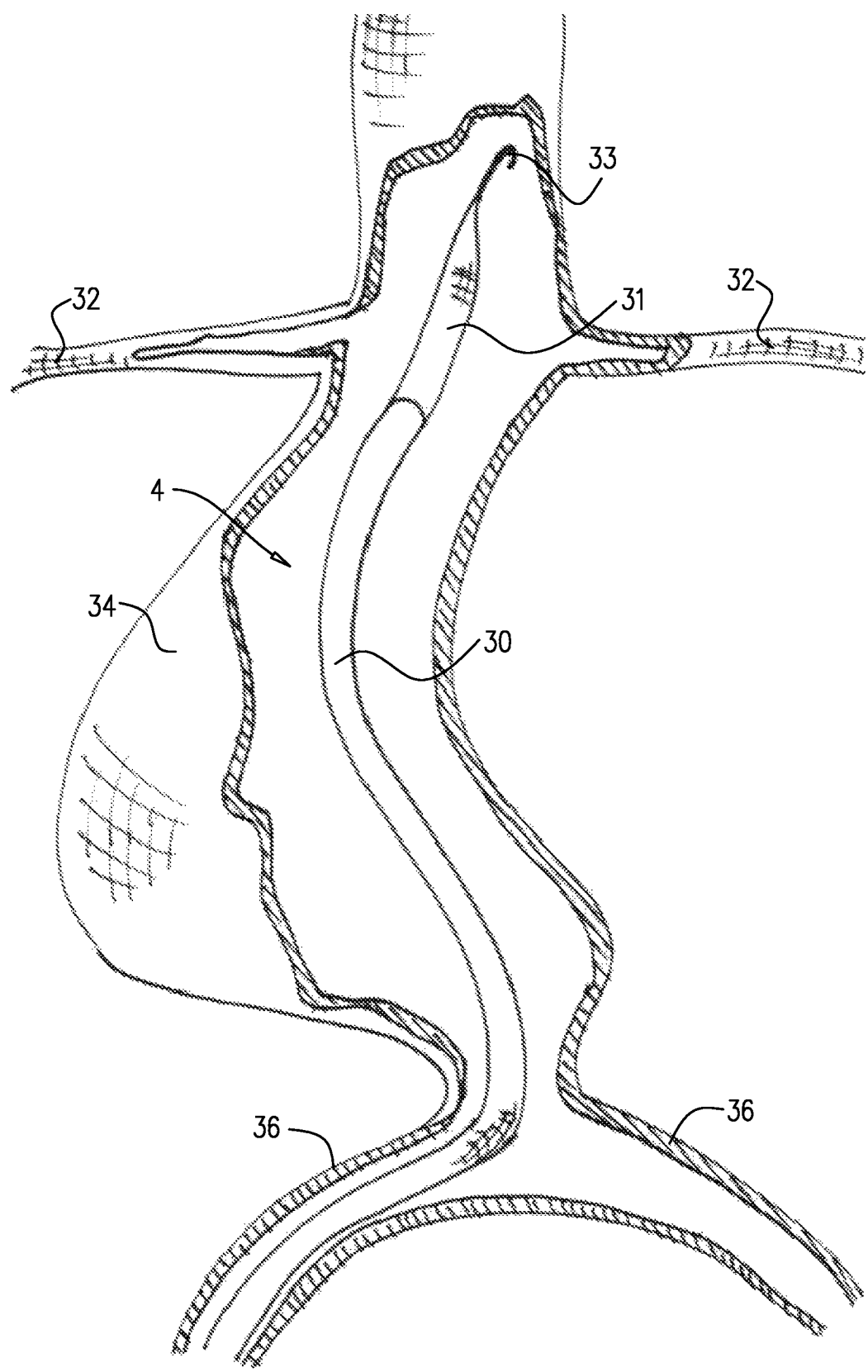
FIGS. 14A-E are schematic illustrations of an exemplary method of deploying the endovascular stent-graft of FIG. 13 in an aneurysmatic abdominal aorta, in accordance with an application of the present invention.

FIG. 13 is a schematic illustration of a unilumen endovascular stent-graft 200, in accordance with an application of the present invention. Endovascular stent-graft 200 is configured to initially be positioned in a delivery catheter in a radially-compressed state, as described hereinbelow with reference to FIG. 14A, and to assume a radially-expanded state upon being deployed from the delivery catheter, as described hereinbelow with reference to FIGS. 14B-D. FIG. 13 shows the endovascular stent-graft in the radially-expanded state.

Stent-graft 200 comprises rostral and caudal body portions 210 and 212, which comprise rostral and caudal structural members 214 and 216, respectively. Stent-graft 200 also comprises a middle body portion 218, disposed longitudinally between rostral and caudal body portions 210 and 212. Stent-graft 200 further comprises a unilumen fluid flow guide 220. For some applications, middle body portion 218 comprises a middle structural member, which comprises a plurality of structural stent elements, and which is integrally joined to rostral and caudal structural members 214 and 216 (not shown in FIG. 13). For some applications, at least some of, e.g., all of, the structural stent elements are interconnected (as shown in the figures), while for other applications, at least a portion of, e.g., all of, the structural stent elements are not interconnected (configuration not shown). Alternatively, middle body portion 218 is not structurally supported by any structural stent elements. Typically, each of rostral and caudal structural members 214 and 216, and the middle structural member, if provided, comprise a plurality of structural stent elements 222. For some applications, at least some of, e.g., all of, the structural stent elements are interconnected (as shown in the figures), while for other applications, at least a portion of, e.g., all of, the structural stent elements are not interconnected (configuration not shown). For some applications, the structural members comprise a metal. Alternatively or additionally, the structural members comprises a self-expanding material. Alternatively or additionally, the structural members comprise a super-elastic alloy, such as Nitinol. For some applications in which the middle structural member is provided, at least a portion of the middle structural member is configured to be axially expandable. For example, the middle structural member may comprise one or more generally helical wire helices. Optionally, at least one of the helices is a right-handed helix, and at least another of the helices is a left-handed helix. Alternatively, for example, the structural member may comprise a warp lock knitted structure, comprising, for example, polyester (such as the Gelseal™ vascular graft, distributed by Vascutek/Terumo, Scotland, UK). Optionally, fluid flow guide 220 is sparsely attached to the middle structural member.

For some applications, stent-graft 200 further comprises a plurality of rostral anchoring elements 224 that extend radially outwardly when the stent-graft assumes the radially-expanded state, the anchoring elements disposed rostral to rostral body portion 210. The anchoring elements anchor the stent-graft to the vascular wall, helping prevent dislodgement. Optionally, one or more of anchoring elements 224 are shaped so as to define respective barbs 226. Alternatively, for some applications, stent-graft 200 comprises prosthesis member 80, described hereinabove with reference to FIGS. 10A-B, which is coupled to the rostral end of the stent-graft.

Fluid flow guide 220 comprises at least one biologically-compatible substantially fluid-impervious flexible sheet, which is coupled to rostral and caudal structural members 214 and 216, either outside or within the structural members, such as by stitching, and at least partially covers either an external or an internal surface of both of the structural members. A middle portion 228 of fluid flow guide 220 extends longitudinally along an entire length of middle body portion 218. The flexible sheet may comprise, for example, a polymeric material (e.g., polytetrafluoroethylene), a textile material (e.g., polyethylene terephthalate (PET)), natural tissue (e.g., saphenous vein or collagen), a polyester, or a combination thereof. Optionally, a rostral end of rostral structural member 214 extends beyond a rostral end of fluid flow guide 220, for example, slightly beyond, as shown in FIG. 13. Optionally, a caudal end of caudal structural member 216 extends beyond a caudal end of fluid flow guide 220, for example, slightly beyond, as shown in FIG. 13. For some applications, the rostral end of the fluid flow guide is disposed within 4 cm of the rostral end of rostral structural member 214. For some applications, the caudal end of the fluid flow guide is disposed within 20 cm of the caudal end of caudal structural member 216.

Fluid flow guide 220 defines a single, non-bifurcated lumen, so as to define a single fluid flow path through the stent-graft. The single lumen is configured to entirely span the abdominal aorta between the renal arteries and the aorto-iliac bifurcation, and not to substantially extend into the aorto-iliac bifurcation, i.e., to extend into the aorto-iliac bifurcation less than 1 cm, or not at all.

Typically, at least a portion of middle portion 228 of fluid flow guide 220 is axially expandable. For example, the portion may be pleated, e.g., accordion-pleated, or may comprise a longitudinally elastic material. For some applications, the stent-graft is configured such that an axial length of the stent-graft between a rostral end of the rostral body portion and a caudal end of the caudal body portion is variable between a minimum length and a maximum length, the minimum length between 2 and 5 cm, and the maximum length between 10 and 20 cm. For some applications, the stent-graft is configured such that an axial length of axially-expandable portion of the middle portion is variable up to a maximum length change, which maximum length change is between 2 and 20 cm.

For some applications, at least a portion of middle portion 228 of the fluid flow guide 220 is kink-resistant. For example, the portion may comprise a wrap-knit accordion structure, rings periodically attached thereto, a wire helix attached thereto, or a stiff material, and/or other techniques known in the art for providing kink-resistance may be used. For some applications, when the stent-graft assumes the radially-expanded state, middle portion 228 of fluid flow guide 220 is generally tubular, such as generally cylindrical.

For some applications, when the stent-graft assumes the radially-expanded state, a rostral portion of fluid flow guide 220 that at least partially covers rostral structural member 214 is shaped so as to define rostral radially-diverging and radially-converging portions 230 and 232, which portions together define a rostral bulge 234 that extends radially outward, which bulge has a greatest cross-sectional area that is equal to at least 120% e.g., at least 180%, of a cross-sectional area of a narrowest portion 236 of the rostral body portion rostral to the bulge (the rostral body portion may have an even narrower portion caudal to the bulge). When the stent-graft assumes the radially-expanded state, a caudal portion of fluid flow guide 220 that at least partially covers caudal structural member 216 is shaped so as to define caudal radially-diverging and radially-converging portions 240 and 242, which portions together define a caudal bulge 244 that extends radially outward, which bulge has a greatest cross-sectional area that is equal to at least 120% e.g., at least 180%, of a cross-sectional area of a narrowest portion 246 of the caudal body portion caudal to the bulge (the caudal body portion may have an even narrower portion rostral to the bulge). Rostral and caudal bulges 234 and 234 help to prevent a current or a future type I endoleak at a rostral end and a caudal end of an aortic aneurysm, respectively. Typically, when the stent-graft assumes the radially-expanded state, a site on rostral bulge 234 that has the greatest cross-section area is within 10 cm of the rostral end of fluid flow guide 220, and a site on caudal bulge 244 that has the greatest cross-section area is within 10 cm of the caudal end of fluid flow guide 220.

Typically, the stent-graft is configured such that bulges 234 and 244 expand radially as the rostral end and caudal end of the aneurysm enlarge, respectively, in order to maintain a tight seal with the wall of the aorta, thereby preventing current or future type I endoleaks. At the same time, the stent-graft is configured to apply a radially-outward force that is sufficient to cause the bulges to expand with the aortic wall, but insufficient to itself cause expansion of the aortic wall. For some applications, structural members 214 and/or 216 are configured such that, when the stent-graft assumes the radially-expanded state, bulges 234 and/or 244 each applies a radially-outward force that is less than a radially-outward force applied by anchoring elements 224. For example, the radially-outward force applied by each of the bulges may be between 25% and 50% of the radially-outward force applied by the anchoring elements. For example, the anchoring elements may be configured to apply more than half a newton, no more than five newton, or between half a newton and five newton to the aortic wall. Rostral bulge 234 and anchoring elements 224 exert respective forces against the wall of the aorta, as described hereinabove regarding bulge 20 and anchoring elements 7, with reference to FIG. 4D.

For some applications, first and second subsets of structural stent elements 222 are configured to cause fluid flow guide 220 to define bulges 234 and/or 244, such as described hereinabove with reference to FIGS. 1 and 2, regarding bulge 20 of stent-graft 5. Stent-graft 200 may implement one or more of the described features of first and second subsets 22 and 23, which may have one or more of the described properties (e.g., spring coefficients).

For some applications, when the stent-graft assumes the radially-expanded state, rostral structural member 214 is shaped so as to define a generally cylindrical subportion 250 rostral to rostral bulge 234. For some applications, when the stent-graft assumes the radially-expanded state, rostral structural member 214 is shaped so as to define a generally cylindrical subportion 252 caudal to the rostral bulge. For some applications, a spring coefficient of rostral bulge 234, measured during application of a radial force by a rigid circular disk at a region centered at a first point of the rostral bulge that is furthest from a central longitudinal axis of the stent-graft, is: (a) at least 20% less than a spring coefficient of generally cylindrical subportion 250, measured during application of the radial force by the disk at a region centered at a second point of subportion 250 that is furthest from the axis, (b) at least 20% less than a spring coefficient of generally cylindrical subportion 252, measured during application of the radial force by the disk at a region centered at a third point of subportion 252 that is furthest from the axis, and/or (c) at least 25% less than a spring coefficient of rostral anchoring elements 224, measured during application of the radial force by the disk at a region centered at a fourth point of the anchoring elements that is furthest from the axis, wherein the circular disk has a radius equal to 50% of a radius of the stent-graft at the first point.

For some applications, when the stent-graft assumes the radially-expanded state, caudal structural member 216 is shaped so as to define a radially-outwardly flared subportion 260 caudal to caudal bulge 244. For some applications, when the stent-graft assumes the radially-expanded state, caudal structural member 216 is shaped so as to define a generally cylindrical subportion 262 rostral to caudal bulge 244. For some applications, a spring coefficient of caudal bulge 244, measured during application of a radial force by a rigid circular disk at a region centered at a first point of the caudal bulge that is furthest from a central longitudinal axis of the stent-graft, is: (a) at least 25% less than a spring coefficient of flared subportion 260, measured during application of the radial force by the disk at a region centered at a second point of flared subportion 260 that is furthest from the axis, and/or (b) at least 20% less than a spring coefficient of generally cylindrical subportion 262, measured during application of the radial force by the disk at a region centered at a third point of subportion 262 that is furthest from the axis, wherein the circular disk has a radius equal to 50% of a radius of the stent-graft at the first point. For some applications, a caudal end of the caudal structural member has a shape of a non-circular ellipse or a peanut shell shape (double-lobed) (which widens at each iliac artery, and narrows in the middle).

For some applications, rostral body portion 210 and/or caudal body portion 212 comprise a plurality of anchoring elements 264 that extend radially outward, and assist with anchoring stent-graft 200 to the aortic wall. For some applications, the anchoring element comprises barbs, as shown in FIG. 13. The barbs of rostral body portion 210 may be disposed on radially-converging portion 230, and may extend radially outward in a rostral direction. The barbs of caudal body portion 212 may be disposed on radially-diverging portion 240, and may extend radially outward in a caudal direction. The barbs of the rostral body portion and the barbs of the caudal body portion may thus extend in generally opposite axial directions, in addition to extending radially outward. For other applications, anchoring elements 264 comprise tissue engagement members 52, described hereinabove with reference to FIGS. 7A-C. For some applications, anchoring elements 264 of rostral body portion 210, which may comprise barbs, together with barbs 226 of anchoring elements 224, which may extend radially outwardly and caudally, together pinch tissue therebetween.

For some applications, stent-graft 200 comprises a plurality of barbs 266 disposed at the caudal end of the stent-graft (as shown in FIG. 13) and/or at the rostral end of the stent-graft (not shown). Barbs 266 typically extend radially outward and rostrally toward middle portion 228 of the stent-graft. For some applications, stent-graft 200 comprises both barbs 266 and anchoring elements 264, described above. For some applications, anchoring elements 264 of caudal body portion 212, which may comprise barbs, together with barbs 266, axially pinch tissue therebetween.

FIGS. 14A-D are schematic illustrations of an exemplary method of deploying endovascular stent-graft 200 in an aneurysmatic abdominal aorta, using endovascular stent-graft delivery tool 4, described hereinabove with reference to FIG. 4A, in accordance with an application of the present invention. In order to implant endovascular stent-graft 200, the stent-graft is transvascularly (typically percutaneously) introduced into the aorta via one of iliac arteries 36, while the stent-graft is positioned in delivery catheter 30 in the radially-compressed state. Delivery catheter 30 and distal tip 31 of delivery tool 4 are advanced over guidewire 33 until the distal tip is positioned slightly below renal arteries 32.

Figure 14B:
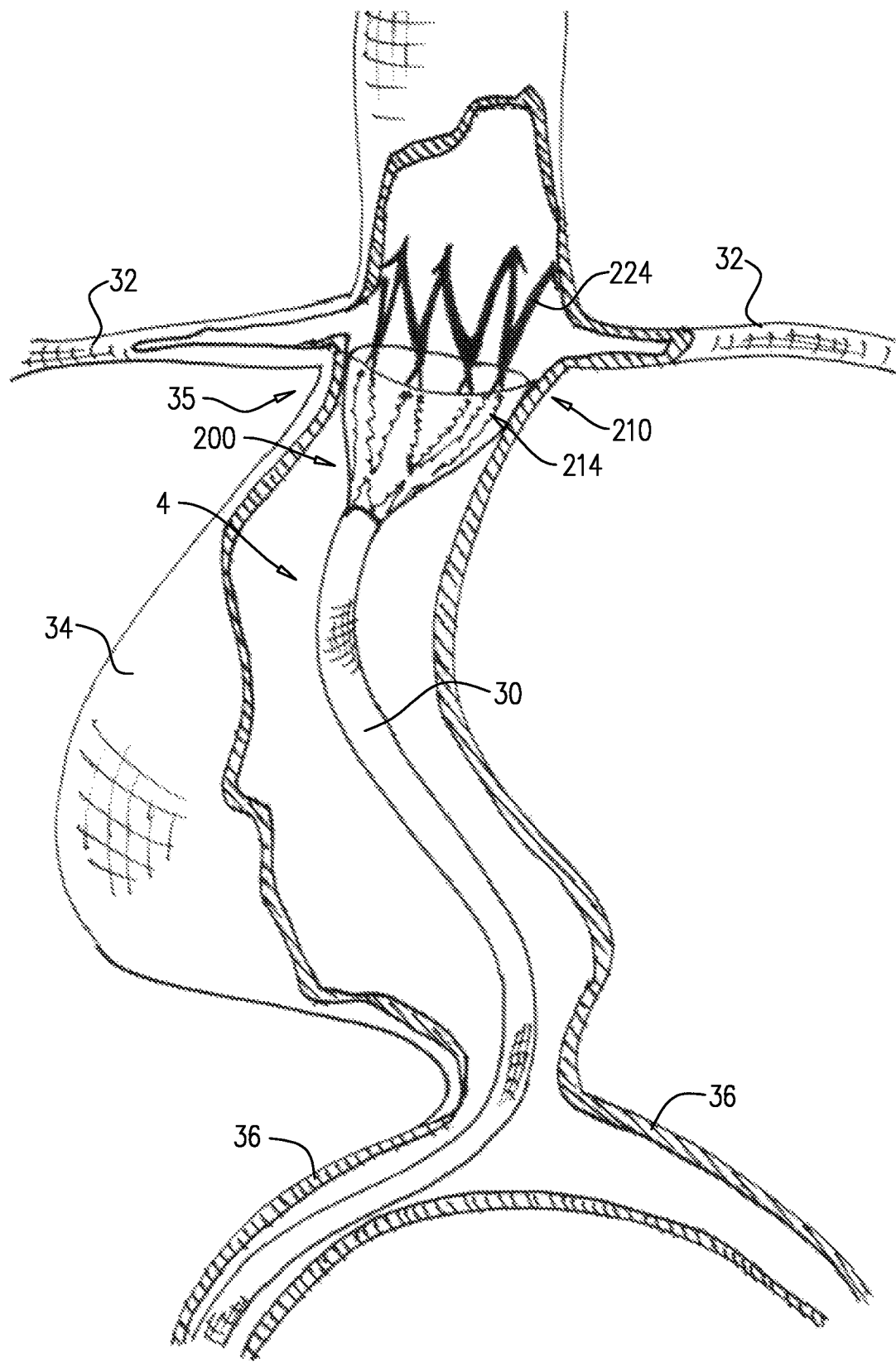

FIG. 14B shows rostral body portion 210 in an early stage of release from delivery catheter 30. The rostral body portion is positioned near rostral end 35 of aneurysm 34. For applications in which rostral anchoring element 224 are provided, the stent-graft is positioned such that the rostral anchoring elements are disposed rostrally to renal arteries 32.

Figure 14C:
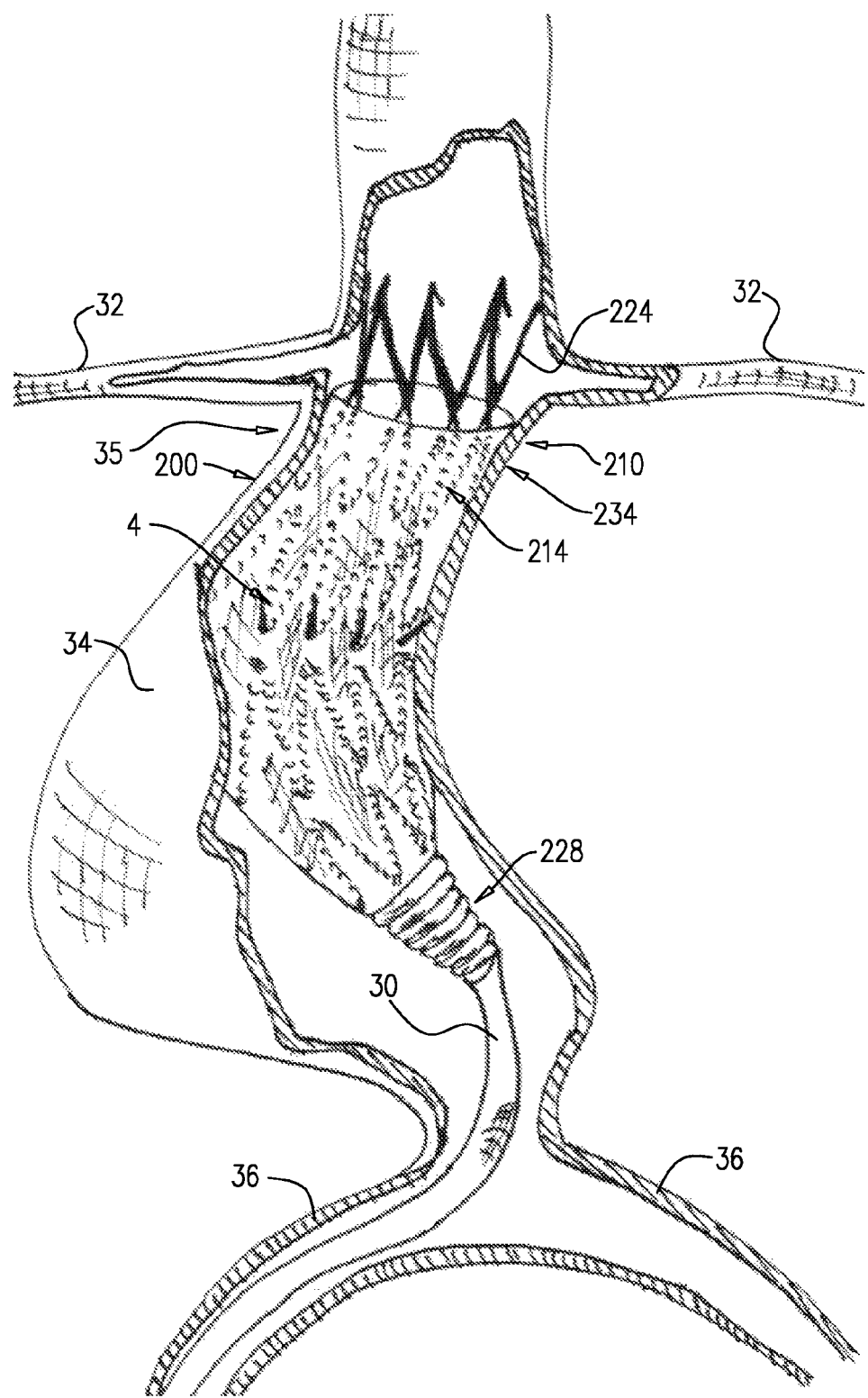

FIG. 14C shows the stent-graft in a subsequent phase of its deployment from delivery catheter 30, in which rostral bulge 234 is disposed in rostral end 35 of aneurysm 34, and sealingly contacts the aortic wall, thereby preventing or reducing the risk of a current or a future a type I endoleak. Middle portion 228 has also been partially deployed from the delivery catheter.

Figure 14D:
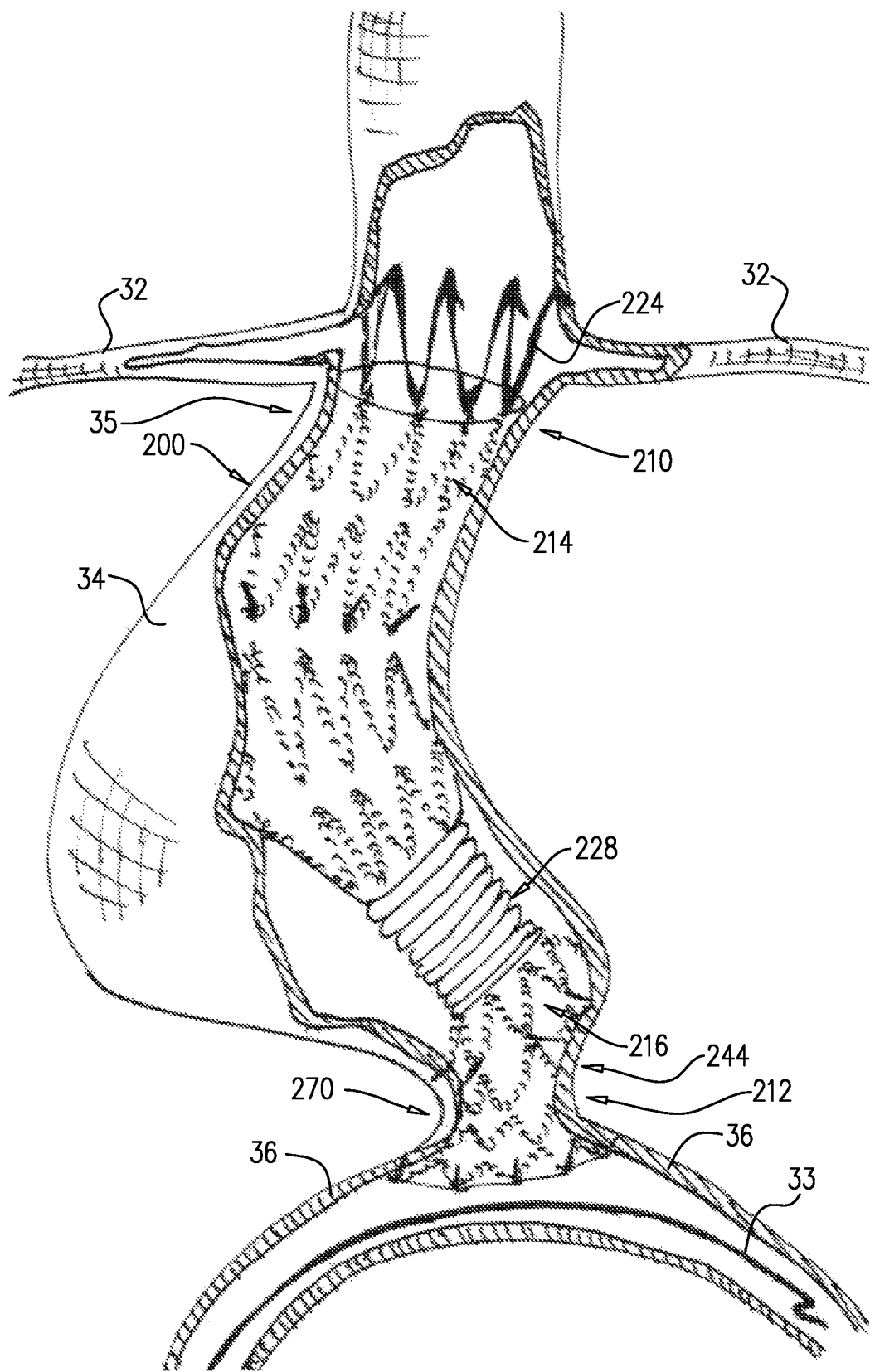

FIG. 14D shows the stent-graft in its fully deployed state, after delivery tool 4 has been removed from the subject's body. Caudal bulge 244 of caudal portion 212 is disposed in a caudal end 270 of aortic aneurysm 34, and sealingly contacts the aortic wall, thereby preventing or reducing the risk of a current or a future a type I endoleak. Middle portion 228 has axially expanded as necessary such that the single lumen of the stent-graft entirely spans the abdominal aorta between renal arteries 32 and an aorto-iliac bifurcation.

Figure 14E:
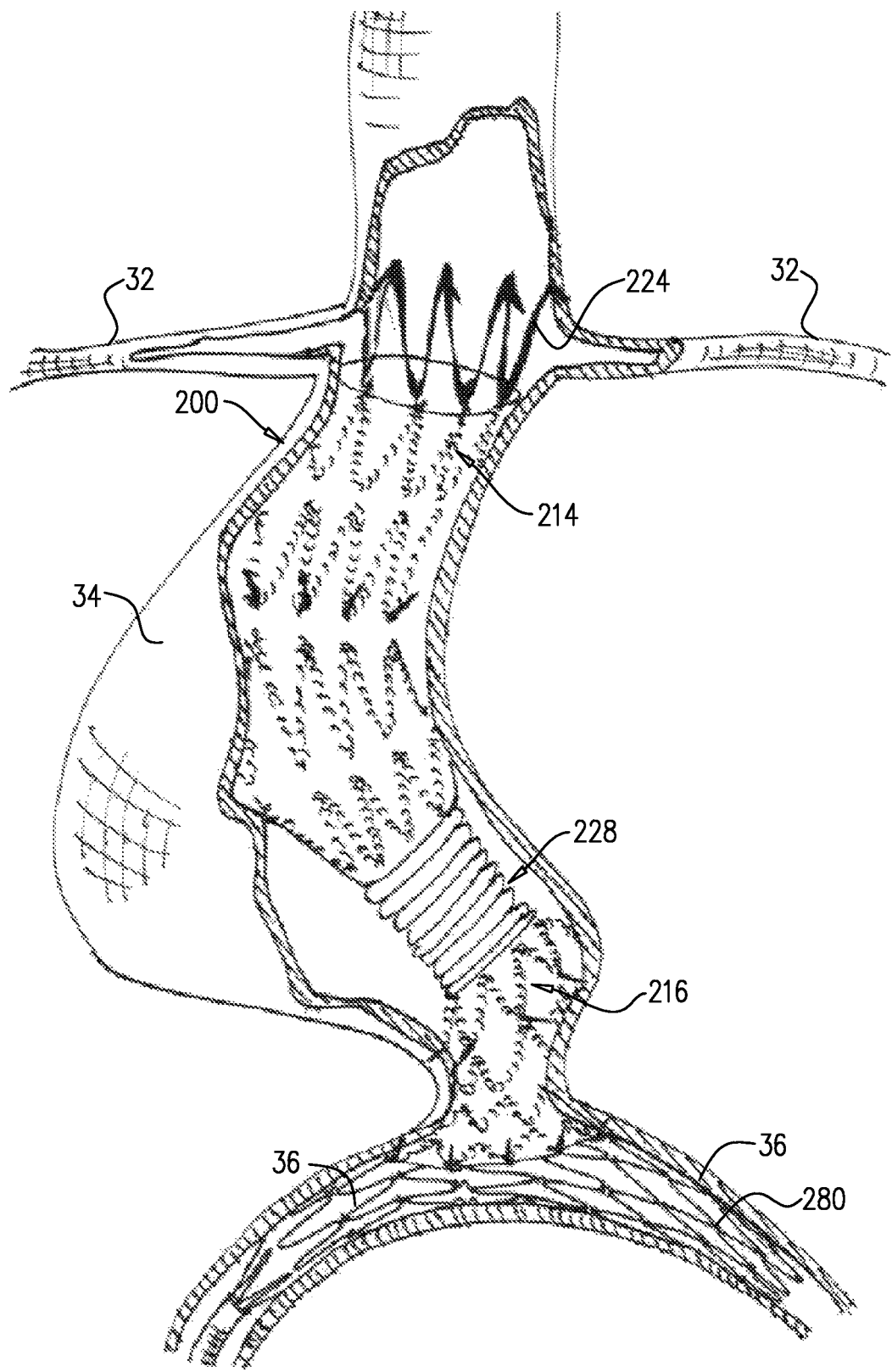

FIGS. 14D-E show an optional portion of the implantation procedure, in which a bi-iliac self-expandable stent 280 is deployed in the iliac arteries, in order to facilitate improved long-term anchoring of stent-graft 200 at the aorto-iliac bifurcation. FIG. 14D shows the introduction of guidewire 33 or another endovascular guidewire, from an entry-point in iliac artery 36A to a contralateral iliac artery 36B. FIG. 14E shows the deployment of bi-iliac stent 280 over the guidewire into both iliac arteries. Optionally, a balloon (e.g., an angioplasty balloon) may subsequently be inflated within the bi-iliac stent, so as to crush caudal flared subportion 260 of stent-graft 200 toward the aorto-iliac neck (not shown).

Figure 15C:
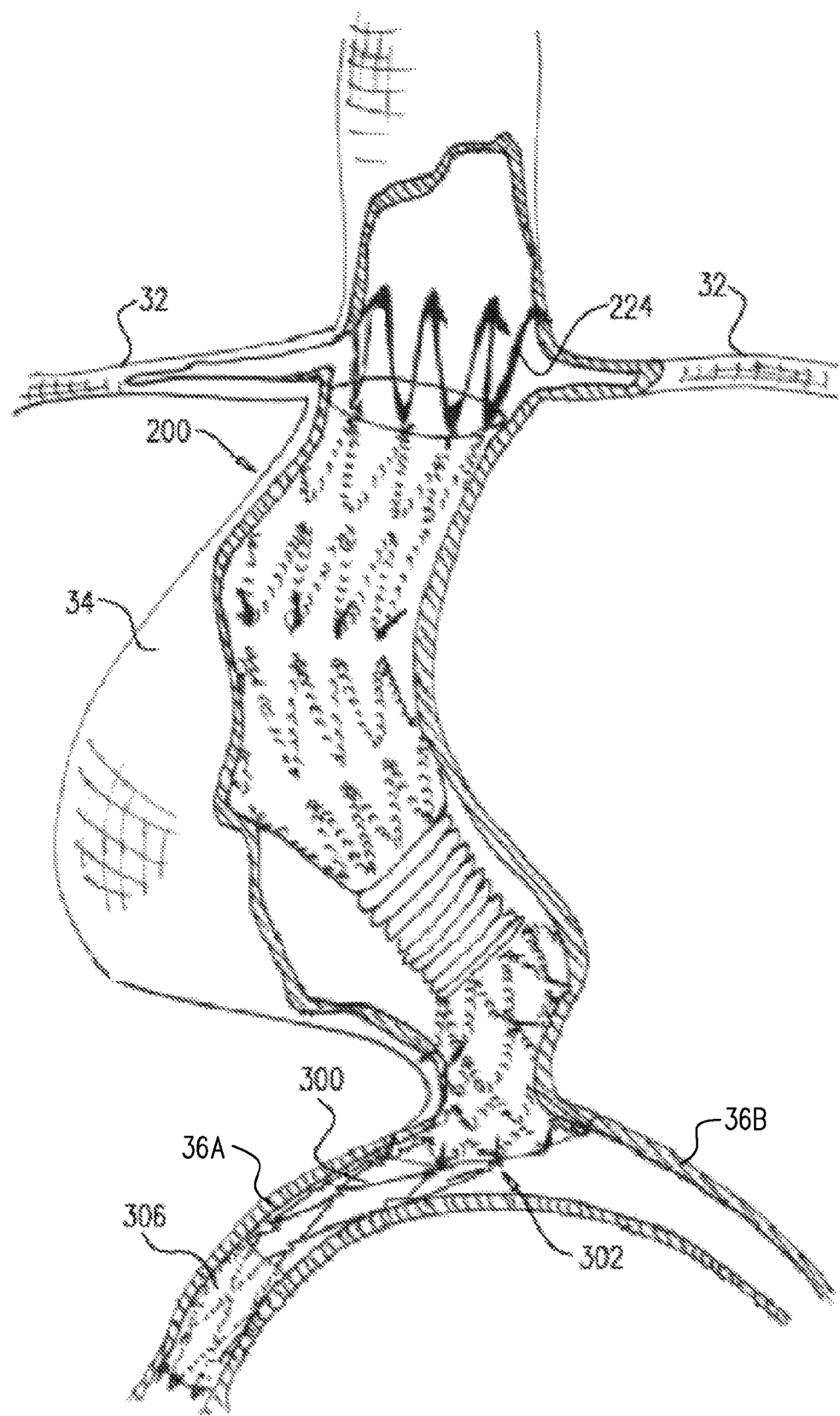

FIGS. 15A-C are schematic illustrations of stent-graft 200 coupled to a uni-iliac self-expandable extension stent 300, in accordance with respective applications of the present invention. A rostral end of uni-iliac extension stent 300 is coupled to a caudal end of caudal body portion 212 of stent-graft 200 along a portion of a circumference of the caudal end, such as less than 40 degrees of the circumference. Uni-iliac extension stent 300 is shaped such that a rostral portion thereof defines a lateral opening 302 therethrough, defined by a discontinuity of stent cells along a portion of the circumference of the extension stent, such as more than 320 degrees of the circumference. After deployment of stent-graft 200 in the aorta and uni-iliac stent 300 in one of the iliac arteries, a bi-iliac stent (not shown) is advanced through the iliac artery in which uni-iliac stent 300 is positioned, passed through opening 302, and then into the other iliac artery. The bi-iliac stent and uni-iliac stent 300 help hold stent-graft 200 anchored in place, especially in the aorto-iliac bifurcation. For some applications, the uni-iliac extension stent is bare, i.e., a fluid flow guide is not coupled to the extension stent.

For some applications, the bi-iliac stent comprises a super-elastic alloy, such as Nitinol. For some applications, a portion of the uni-iliac stent that is positioned in the other iliac artery comprises an extension fluid flow guide, for treating an iliac aneurysm of the other iliac artery. The extension fluid flow guide comprises at least one biologically-compatible substantially fluid-impervious flexible sheet, and covers at least a portion of the uni-iliac extension stent. For some applications, the uni-iliac extension stent comprises a super-elastic alloy, such as Nitinol. For some applications, at least one radiopaque marker is provided for aiding in achieving a desired rotational orientation of the stent-graft and the uni-iliac extension stent. The at least one radiopaque marker is disposed on at least one of: the stent-graft, the uni-iliac extension stent, and the delivery catheter.

For some applications, as shown in FIG. 15B, a portion 304 of uni-iliac stent-graft 300 caudal to opening 302 comprises a fluid flow guide 306, which comprises at least one biologically-compatible substantially fluid-impervious flexible sheet, and which is coupled to a stent body of the uni-iliac stent-graft. The fluid flow guide may help treat an iliac aneurysm.

FIG. 15C is a schematic illustration of the configuration of stent-graft 200 of FIG. 15B deployed in an aneurysmatic aorta, in accordance with an application of the present invention. Uni-iliac stent 300 is deployed in right iliac artery 36A. (The bi-iliac stent which is subsequently deployed is not shown in the figure.)

Figure 16:
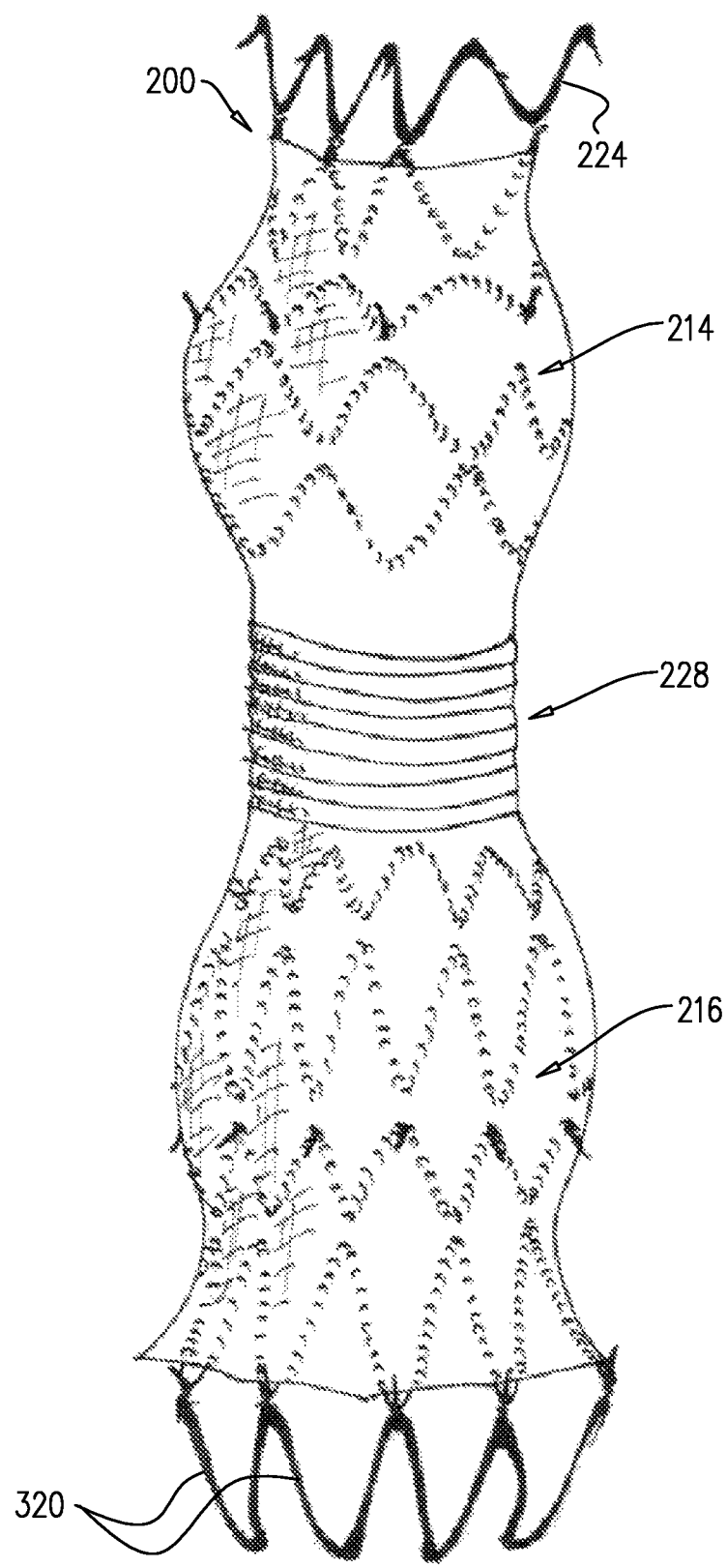
FIG. 16 is a schematic illustration of a configuration of the unilumen endovascular stent-graft of FIG. 13 further comprising a plurality of circumferentially-disposed, axially-oriented engagement members, in accordance with an application of the present invention.

FIG. 16 is a schematic illustration of a configuration of stent-graft 200 further comprising a plurality of circumferentially-disposed, axially-oriented engagement members 320, coupled to a caudal end of caudal structural member 216, in accordance with an application of the present invention. Engagement members 320 are configured to prevent down-migration of stent-graft 200 through the aorto-iliac bifurcation, which might obstruct the bifurcation.

For some applications, a self-expandable bi-iliac stent is further provided (not shown). The bi-iliac stent comprises a bi-iliac stent body, and, optionally, a fluid flow guide, which comprises at least one biologically-compatible substantially fluid-impervious flexible sheet, and which is coupled to the bi-iliac stent body. The bi-iliac stent is (a) advanced through one of the iliac arteries, (b) passed through engagement members 320, such that at least a portion of engagement members 320 and the bi-iliac stent-body engage each other (e.g., interlock with each other), and then (c) into the other iliac artery. The bi-iliac stent helps hold stent-graft 200 anchored in place.

Figure 17:
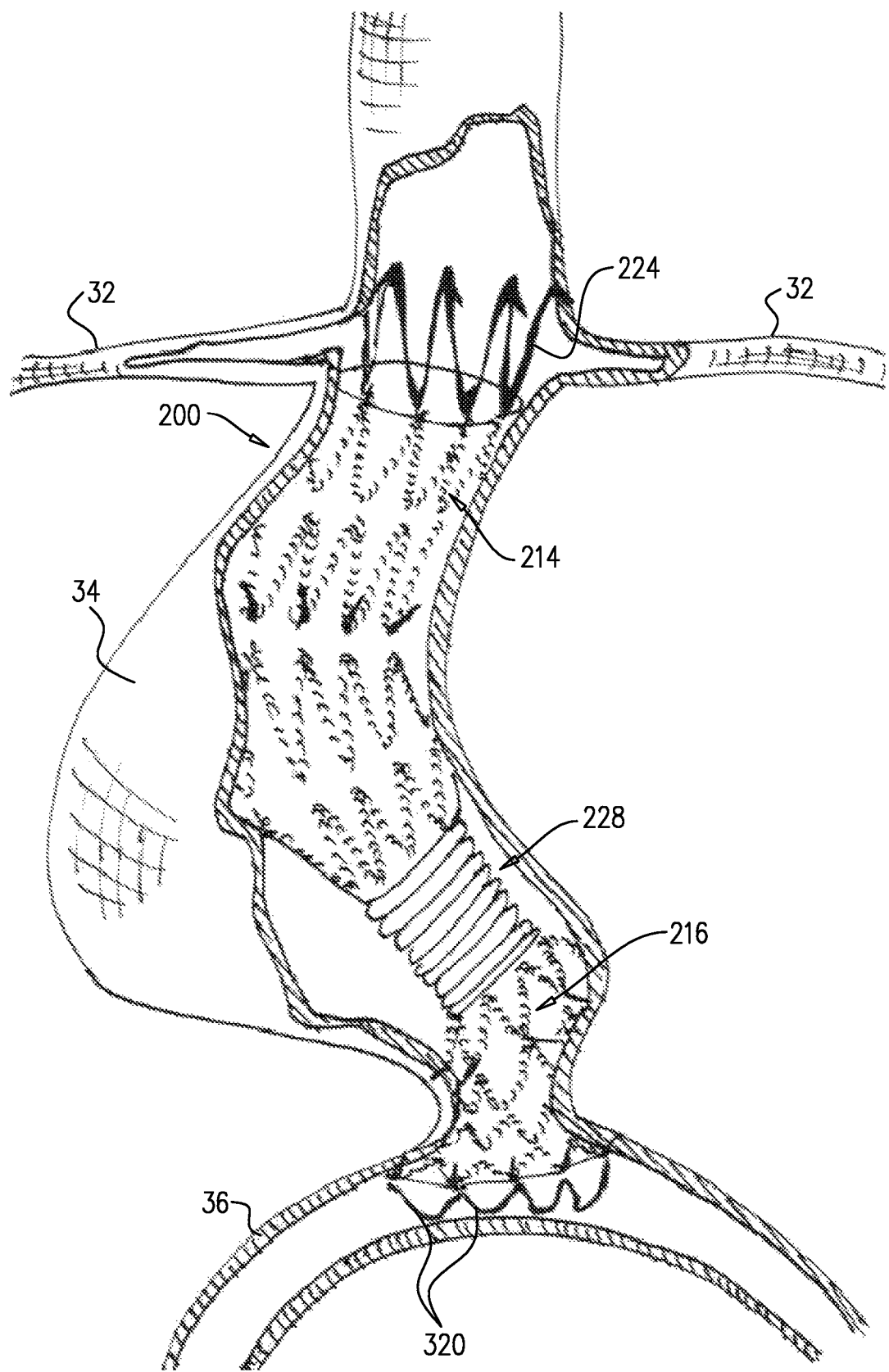
FIG. 17 is a schematic illustration of the configuration of the stent-graft of FIG. 16 deployed in an aneurysmatic aorta, in accordance with an application of the present invention.
Figure 20A:
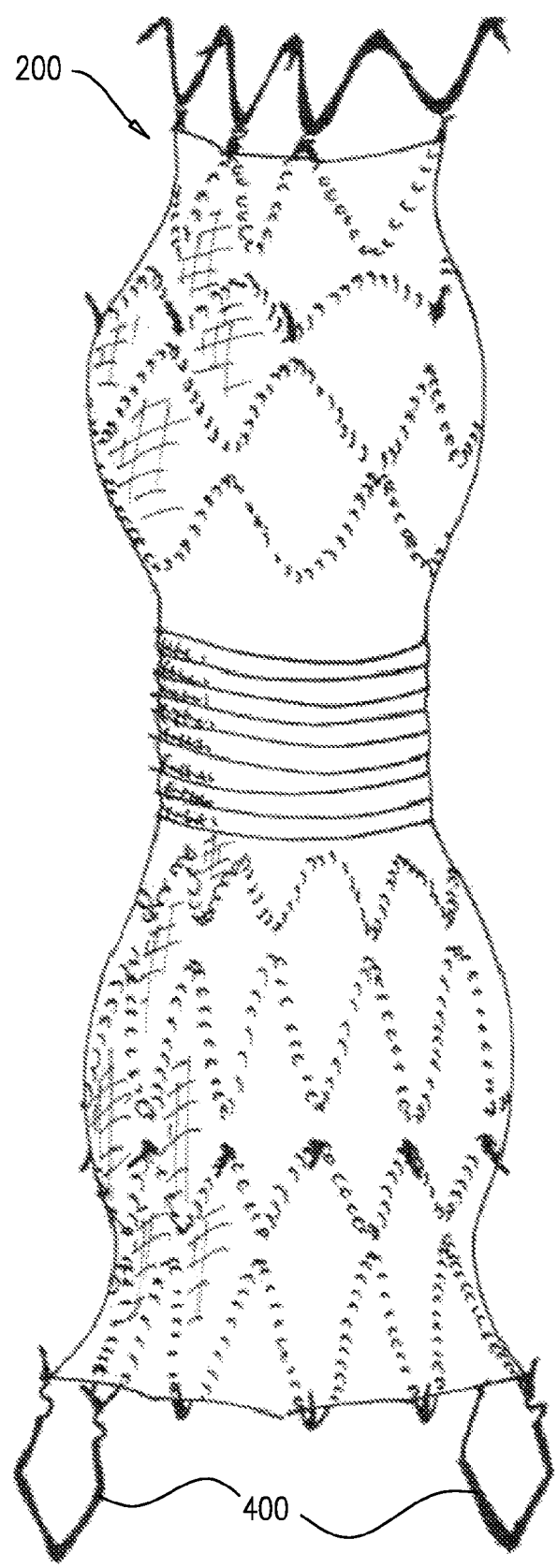
FIGS. 20A-B are schematic illustrations of a configuration of the unilumen endovascular stent-graft of FIG. 13 further comprising at least two iliac engagement members, in accordance with an application of the present invention.
Figure 20B:
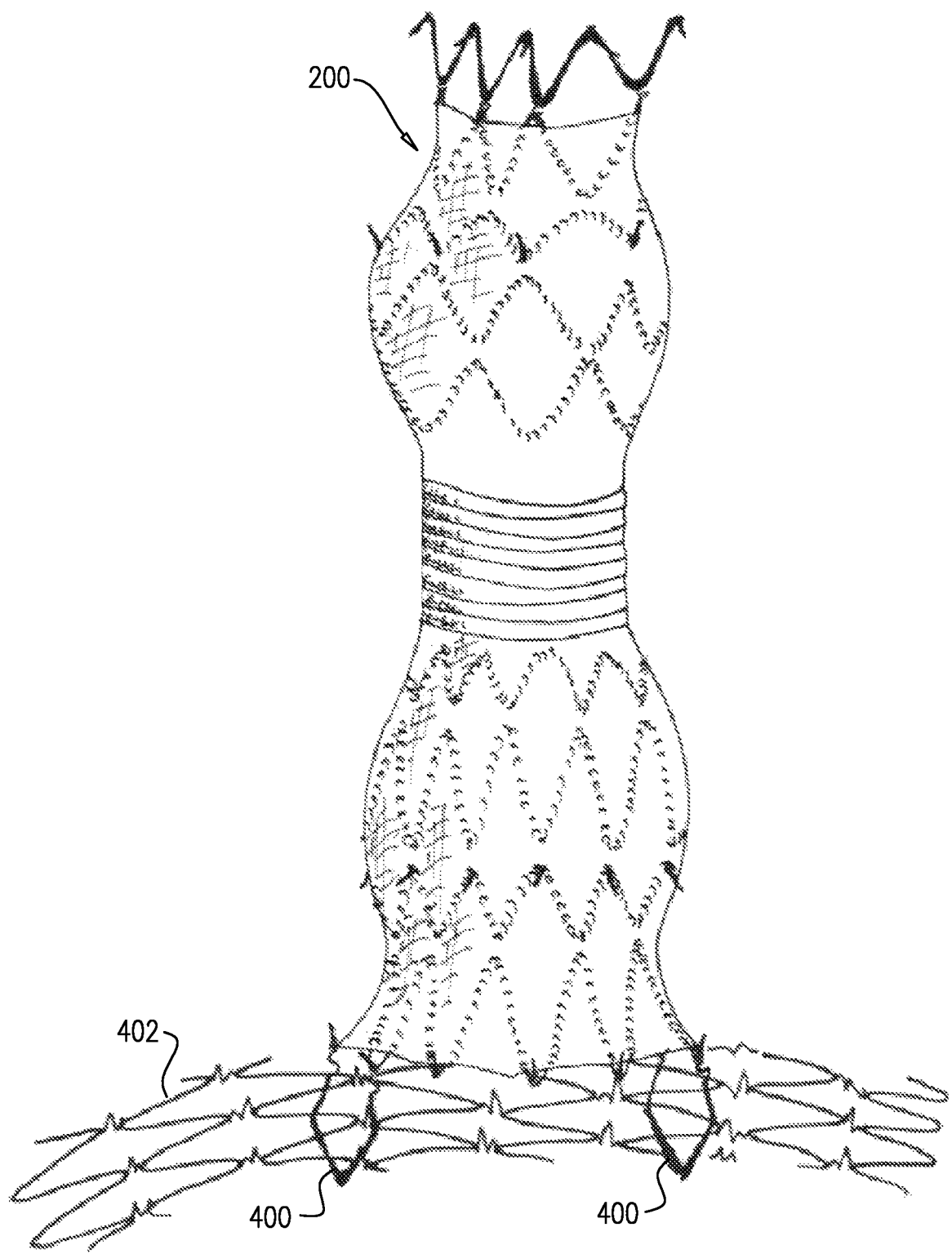

FIG. 17 is a schematic illustration of the configuration of stent-graft 200 of FIG. 16 deployed in an aneurysmatic aorta, in accordance with an application of the present invention. The bi-iliac stent is not shown.

FIG. 18 is a schematic illustration of a configuration of stent-graft 200 further comprising a self-expandable uni-iliac extension stent 340, in accordance with an application of the present invention. In this configuration, a rostral end of uni-iliac extension stent 340 is coupled within caudal body portion 212 of stent-graft 200, typically at or near a caudal end of caudal bulge 244, such that the rostral end of uni-iliac extension stent 340 passes through the caudal end of caudal body portion 212 and into an interior of the caudal body portion. Uni-iliac extension stent 340 may help anchor stent-graft 200 in place in the aorta, as well as treat an iliac aneurysm, in some applications. Stent-graft 200 and iliac extension stent 340 serve in combination as an aorto-uni-iliac stent-graft.

For some applications, a rostral portion 342 of the uni-iliac extension stent is shaped so as to provide a lateral opening 344 therethrough, defined by a discontinuity of stent cells along a portion of the circumference of the aorto-uni-iliac stent, such as more than 320 degrees of the circumference. After deployment of stent-graft 200 in the aorta and uni-iliac extension stent 340 in one of the iliac arteries, a bi-iliac stent (not shown) is advanced through the iliac artery in which uni-iliac stent 340 is positioned, passed through opening 344, and then into the other iliac artery. The bi-iliac stent and the aorto-uni-iliac stent help hold stent-graft 200 anchored in place.

For some applications, a caudal portion 346 of uni-iliac extension stent 340 comprises a fluid flow guide 348, which comprises at least one biologically-compatible substantially fluid-impervious flexible sheet, and which is coupled to a stent body of the uni-iliac stent. Fluid flow guide 348 may help treat an iliac aneurysm.

FIG. 19 is a schematic illustration of stent-graft 200 coupled to a uni-iliac self-expandable stent 360, in accordance with an application of the present invention. A rostral end of uni-iliac stent 300 is coupled to a caudal end of stent-graft 200. Uni-iliac stent 360 is similar to uni-iliac stent 300, described hereinabove with reference to FIG. 15, except that a rostral portion of stent 360 does not lack any stent cells to particularly define a lateral opening therethrough. Instead, after deployment of stent-graft 200 in the aorta and uni-iliac stent 360 in one of the iliac arteries, a bi-iliac stent (not shown) is advanced through the iliac artery in which uni-iliac stent 300 is positioned, passed through one of the cells of stent 360, and then into the other iliac artery. Because the passages through the cells are smaller than opening 302 of stent 300, the bi-iliac stent in this configuration must have a smaller cross-section when the uni-iliac stent assumes a radially-compressed state during delivery of the stent, than in the configuration of FIG. 15. The bi-iliac stent and uni-iliac stent 300 help hold stent-graft 200 anchored in place.

For some applications, a caudal portion of uni-iliac stent-graft 360 comprises a fluid flow guide, which comprises at least one biologically-compatible substantially fluid-impervious flexible sheet, and which is coupled to a stent body of the uni-iliac stent-graft. The fluid flow guide may help treat an iliac aneurysm. Although not shown in FIG. 19, the fluid flow guide is similar to fluid flow guide 348, described hereinabove with reference to FIG. 18.

Figure 21A:
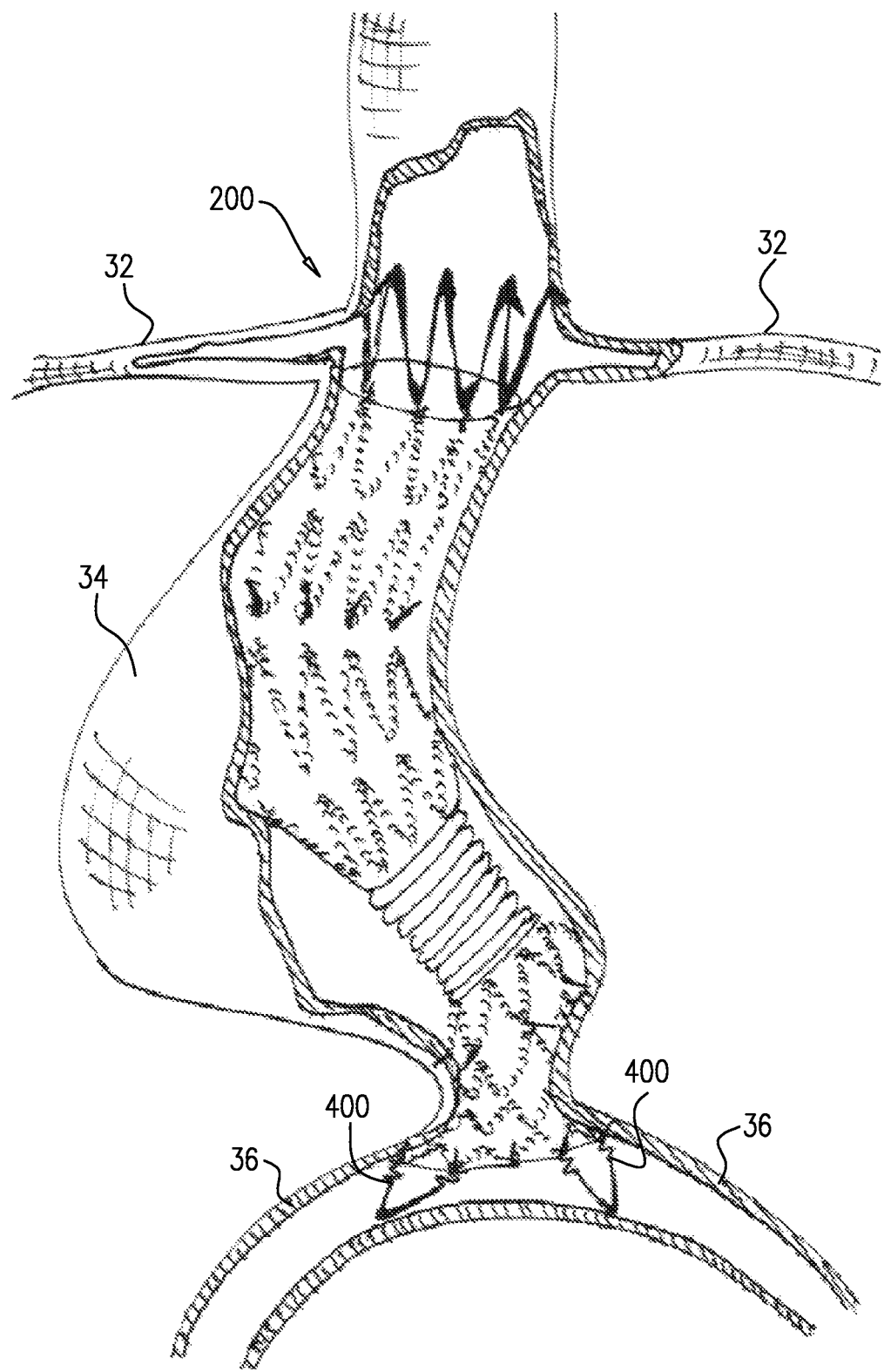
FIGS. 21A-B are schematic illustrations of the configuration of the unilumen stent-graft of FIGS. 20A-B deployed in an aneurysmatic aorta, in accordance with an application of the present invention.
Figure 21B:
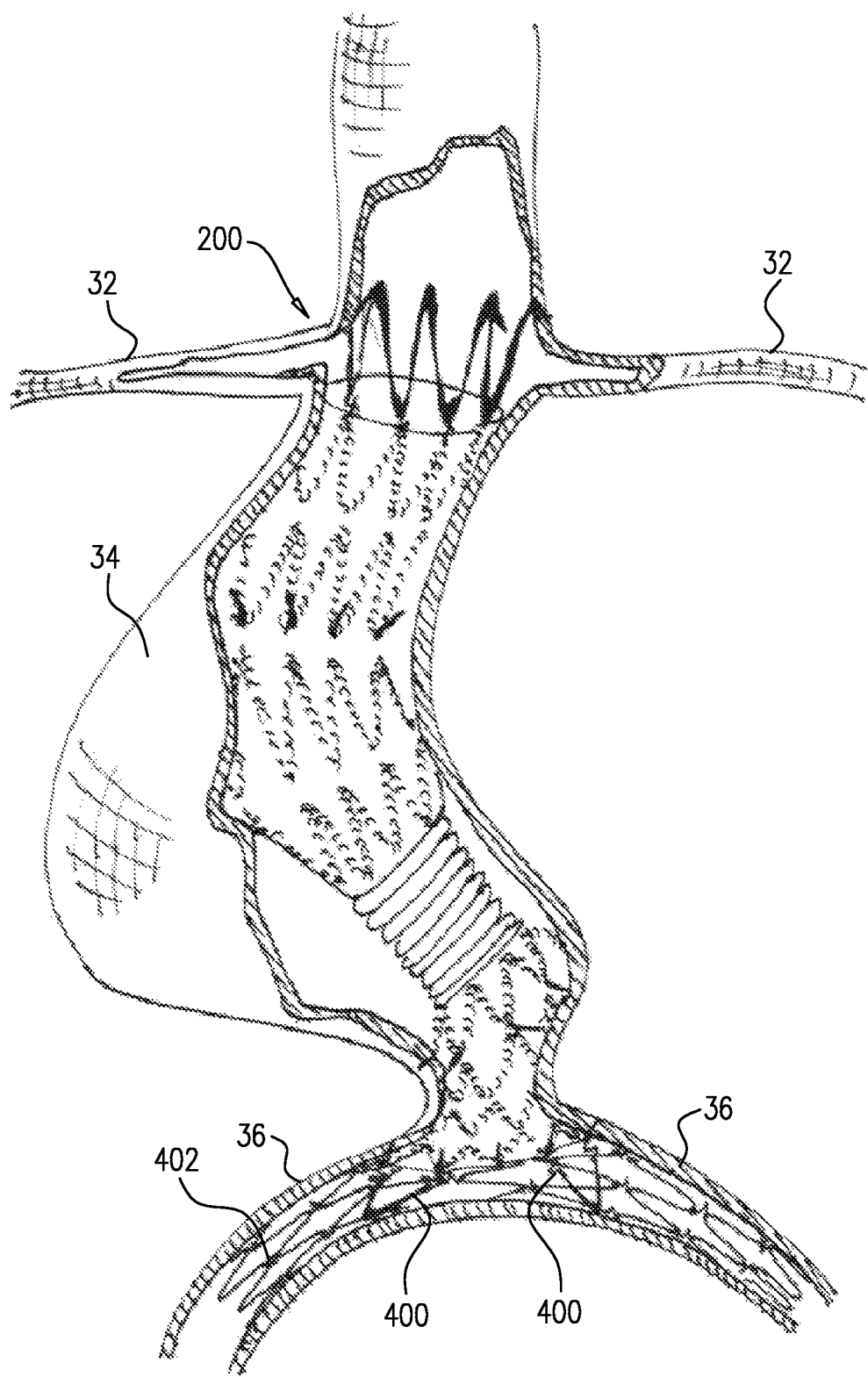

FIGS. 20A-21B are schematic illustrations of a configuration of stent-graft 200 further comprising at least two (e.g., exactly two) iliac engagement members 400, in accordance with an application of the present invention. Iliac engagement members 400 are coupled to a caudal end of caudal structural member 216, typically on opposites sides of the caudal end. Optionally, the engagement members are radially outwardly flared in a caudal direction (configuration not shown). As shown in FIGS. 20B and 21B, a self-expandable bi-iliac stent 402 is further provided. The bi-iliac stent comprises a bi-iliac stent body. For some applications, the bi-iliac stent further comprises a fluid flow guide, which comprises at least one biologically-compatible substantially fluid-impervious flexible sheet, and which is coupled to the bi-iliac stent body (configuration not shown).

FIGS. 21A-B show two steps of an implantation procedure. FIG. 21A shows stent-graft 200 deployed in an aneurysmatic aorta, as described hereinabove with reference to FIGS. 14A-D. Iliac engagement members 400 extend caudally into iliac arteries 36. As shown in FIG. 21B, bi-iliac stent 402 is (a) advanced through one of the iliac arteries, (b) passed through iliac engagement members 400, such that engagement members 400 and the bi-iliac stent-body engage each other (e.g., interlock with each other), and then (c) into the other iliac artery. The bi-iliac stent helps hold stent-graft 200 anchored in place.

In the present application, including in the claims, the term "rostral" means closer to the heart via the aortic vasculature, and the term "caudal" means further from the heart via the aortic vasculature. For example, the renal arteries are "rostral" to the aorto-iliac bifurcation. The terms "upstream" and "downstream" may be used interchangeably with the terms "rostral" and "caudal," respectively, and refer to the orientation of the apparatus with respect to the direction of blood flow.

Although the endovascular prostheses described herein are generally described as being deployed via an iliac artery and the aorto-iliac bifurcation, for some applications, the prostheses are instead deployed via a subclavian artery.

The scope of the present invention includes embodiments described in the following applications, which are assigned to the assignee of the present application and are incorporated herein by reference. In an embodiment, techniques and apparatus described in one or more of the following applications are combined with techniques and apparatus described herein:

PCT Application PCT/IL2008/000287, filed Mar. 5, 2008, which published as PCT Publication WO 2008/107885 to Shalev et al.

U.S. application Ser. No. 12/529,936, which published as US Patent Application Publication 2010/0063575 to Shalev et al.

U.S. Provisional Application 60/892,885, filed Mar. 5, 2007
U.S. Provisional Application 60/991,726, filed Dec. 2, 2007
U.S. Provisional Application 61/219,758, filed Jun. 23, 2009
U.S. Provisional Application 61/221,074, filed Jun. 28, 2009

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus for use with a delivery catheter, the apparatus comprising an endovascular stent-graft, which is configured to initially be positioned in the delivery catheter in a radially-compressed state, and to assume a radially-expanded state upon being deployed from the delivery catheter, and which comprises:
   a structural member, which comprises a plurality of structural stent elements, at least a portion of which define a stent body when the stent-graft assumes the radially-expanded state; and
   a fluid flow guide, which comprises at least one biologically-compatible substantially fluid-impervious flexible sheet, and which is coupled to the stent body,
   wherein, when the stent-graft assumes the radially-expanded state:
      a first subset of the structural stent elements of the stent body are configured to cause the stent body and the fluid flow guide to define a bulge that extends radially outward, which has a greatest cross-sectional area that is equal to at least 120% of a cross-sectional area of a narrowest portion of the stent-graft rostral to the bulge,
      the fluid flow guide is shaped so as to define radially-diverging and radially-converging portions, which together define the bulge, wherein the radially-diverging portion is rostral to the radially-converging portion,
      a second subset of the structural stent elements of the stent body are not configured to cause the fluid flow guide to define the bulge, and
      the structural stent elements of the first subset overlap the structural stent elements of the second subset lengthwise along the entire radially-diverging portion.

2. The apparatus according to claim 1, wherein, when the stent-graft assumes the radially-expanded state, the fluid flow guide, including a bulging portion thereof that defines the bulge, defines a fluid flow path through the stent body.

3. The apparatus according to claim 1, wherein the structural stent elements comprise a metal, and wherein the structural stent elements of the first subset contact at least a portion of the structural stent elements of the second subset, when the stent-graft assumes the radially-compressed state.

4. The apparatus according to claim 1, wherein a spring coefficient of the first subset, measured during application of a radial force by a rigid circular disk at a region centered at a first point of the first subset that is furthest from a central longitudinal axis of the stent-graft, is at least 20% less than a spring coefficient of the second subset, measured during application of a radial force by the disk at a region centered at a second point of the second subset that is axially aligned with the first point, wherein the circular disk has a radius equal to 50% of a radius of the stent body at the first point.

5. The apparatus according to claim 1, wherein the structural stent elements of the second subset are shaped so as to define a substantially tubular structure, when the stent-graft assumes the radially-expanded state.

6. The apparatus according to claim 5, wherein the substantially tubular structure is a constant diameter cylinder, when the stent-graft assumes the radially-expanded state.

7. The apparatus according to claim 5, wherein the substantially tubular structure is a flared cylinder, when the stent-graft assumes the radially-expanded state.

8. The apparatus according to claim 1, wherein, when the stent-graft assumes the radially-expanded state, the structural stent elements of the first subset are shaped so as to define a plurality of arms that extend radially outward, and are configured to cause the fluid flow guide to define the bulge.

9. The apparatus according to claim 8, wherein the arms extend radially outward in a caudal direction, when the stent-graft assumes the radially-expanded state.

10. The apparatus according to claim 1, wherein the first and second subsets are mutually exclusive.

11. The apparatus according to claim 1, wherein the first and second subsets share at least one of the structural stent elements.

12. The apparatus according to claim 1, wherein the structural stent elements of the first subset are interconnected.

13. The apparatus according to claim 1, wherein the structural stent elements of the second subset are interconnected.

14. The apparatus according to claim 1, wherein a third subset of the structural stent elements of the stent body connect the structural stent elements of the first subset with the structural stent elements of the second subset.

15. The apparatus according to claim 14, wherein the structural stent elements of the third subset are substantially radially oriented, when the stent-graft assumes the radially-expanded state.

16. The apparatus according to claim 1, wherein the structural stent elements of the first subset are concentric with the structural stent elements of the second subset, when the stent-graft assumes the radially-expanded state.

17. The apparatus according to claim 1, wherein the structural stent elements of the first subset radially converge with the structural elements of the second subset at respective rostral ends of the first and second subsets.

18. The apparatus according to claim 1, wherein the structural stent elements of the first subset radially converge with the structural elements of the second subset at respective caudal ends of the first and second subsets.

19. The apparatus according to claim 1, wherein, when the stent-graft assumes the radially-expanded state, the structural stent elements of the first subset are grouped into a plurality of axially-disposed arrays of the structural stent elements, each of the arrays generally circumscribing at least a 360-degree arc, each of the arrays being substantially morphologically deformable independently of the axially adjacent arrays.

20. The apparatus according to claim 19, wherein at least a portion of the arrays are structurally connected to the axially adjacent arrays.

21. The apparatus according to claim 19, wherein at least a portion of the arrays are not structurally connected to the axially adjacent arrays.

22. The apparatus according to claim 1, wherein the bulge is adapted to apply an axial force vector in a rostral direction.

23. The apparatus according to claim 1, further comprising the delivery catheter.

24. The apparatus according to claim 1, wherein a site on the bulge that has the greatest cross-section area is within 5 cm of a rostral end of the fluid flow guide, when the stent-graft assumes the radially-expanded state.

25. The apparatus according to claim 1,
wherein the at least a portion of the structural stent elements is a first portion of the structural stent elements, and wherein a rostral-most second portion of the structural stent elements define a plurality of anchoring elements that extend radially outwardly when the stent-graft assumes the radially-expanded state, and
wherein the structural member is configured such that the bulge applies a radially-outward force that is less than a radially-outward force applied by the anchoring elements, when the stent-graft assumes the radially-expanded state.

26. The apparatus according to claim 1, wherein, when the stent-graft assumes the radially-expanded state, the structural stent elements of the first subset overlap the structural stent elements of the second subset lengthwise along the entire radially-diverging portion and along the entire radially-converging portion.

27. Apparatus for use with a delivery catheter, the apparatus comprising an endovascular stent-graft, which is configured to initially be positioned in the delivery catheter in a radially-compressed state, and to assume a radially-expanded state upon being deployed from the delivery catheter, and which comprises:
a structural member, which comprises a plurality of structural stent elements, at least a portion of which define a stent body when the stent-graft assumes the radially-expanded state; and
a fluid flow guide, which comprises at least one biologically-compatible substantially fluid-impervious flexible sheet, and which is coupled to the stent body,
wherein, when the stent-graft assumes the radially-expanded state:
a first subset of the structural stent elements of the stent body are configured to cause the stent body and the fluid flow guide to define a bulge that extends radially outward, which has a greatest cross-sectional area that is equal to at least 120% of a cross-sectional area of a narrowest portion of the stent-graft rostral to the bulge, and
a second subset of the structural stent elements of the stent body (a) are not configured to cause the fluid flow guide to define the bulge, and (b) are shaped so as to define a substantially tubular structure that overlaps the structural stent elements of the first subset lengthwise along the stent body.

28. The apparatus according to claim 27, wherein, when the stent-graft assumes the radially-expanded state, the fluid flow guide is shaped so as to define radially-diverging and radially-converging portions, which together define the bulge, wherein the radially-diverging portion is rostral to the radially-converging portion.

29. The apparatus according to claim 28, wherein, when the stent-graft assumes the radially-expanded state, the substantially tubular structure overlaps the structural stent elements of the first subset overlap the structural stent elements of the second subset lengthwise along the entire radially-diverging portion.

30. The apparatus according to claim 27, wherein, when the stent-graft assumes the radially-expanded state, the structural stent elements of the first subset are shaped so as to define a plurality of arms that extend radially outward, and are configured to cause the fluid flow guide to define the bulge.

31. A method comprising:
providing an endovascular stent-graft, which is configured to assume a radially-compressed state and a radially-expanded state, and which includes (a) a structural member, which includes a plurality of structural stent elements, at least a portion of which define a stent body when the stent-graft assumes the radially-expanded state, and (b) a fluid flow guide, which includes at least one biologically-compatible substantially fluid-impervious flexible sheet, and which is coupled to the stent body, wherein, when the stent-graft assumes the radially-expanded state, (a) a first subset of the structural stent elements of the stent body are configured to cause the stent body and the fluid flow guide to define a bulge that extends radially outward, which has a greatest cross-sectional area that is equal to at least 120% of a cross-sectional area of a narrowest portion of the stent-graft rostral to the bulge, (b) the fluid flow guide is shaped so as to define radially-diverging and radially-converging portions, which together define the bulge, wherein the radially-diverging portion is rostral to the radially-converging portion, (c) a second subset of the structural stent elements of the stent body are not configured to cause the fluid flow guide to define the bulge, and (d) the structural stent elements of the first subset overlap the structural stent elements of the second subset lengthwise along the entire radially-diverging portion;
transvascularly introducing the stent-graft into an aorta of a human subject, while the stent-graft is positioned in a delivery catheter in the radially-compressed state; and
deploying the stent-graft from the delivery catheter at least partially in the aorta such that the bulge extends radially outward against and sealingly contacts a rostral portion of an abdominal aortic aneurysm in the aorta when the stent-graft assumes the radially-expanded state.

32. The method according to claim 31, wherein when the stent-graft assumes the radially-expanded state, the fluid flow guide, including a bulging portion thereof that defines the bulge, defines a fluid flow path through the stent body.

33. The method according to claim 31, wherein, when the stent-graft assumes the radially-expanded state, the structural stent elements of the first subset overlap the structural stent elements of the second subset lengthwise along the entire radially-diverging portion and along the entire radially-converging portion.

34. A method comprising:

providing an endovascular stent-graft, which is configured to assume a radially-compressed state and a radially-expanded state, and which includes (a) a structural member, which includes a plurality of structural stent elements, at least a portion of which define a stent body when the stent-graft assumes the radially-expanded state, and (b) a fluid flow guide, which includes at least one biologically-compatible substantially fluid-impervious flexible sheet, and which is coupled to the stent body, wherein, when the stent-graft assumes the radially-expanded state, (a) a first subset of the structural stent elements of the stent body are configured to cause the stent body and the fluid flow guide to define a bulge that extends radially outward, which has a greatest cross-sectional area that is equal to at least 120% of a cross-sectional area of a narrowest portion of the stent-graft rostral to the bulge, and (b) a second subset of the structural stent elements of the stent body (i) are not configured to cause the fluid flow guide to define the bulge, and (ii) are shaped so as to define a substantially tubular structure that overlaps the structural stent elements of the first subset lengthwise along the stent body;

transvascularly introducing the stent-graft into an aorta of a human subject, while the stent-graft is positioned in a delivery catheter in the radially-compressed state; and deploying the stent-graft from the delivery catheter at least partially in the aorta such that the bulge extends radially outward against and sealingly contacts a rostral portion of an abdominal aortic aneurysm in the aorta when the stent-graft assumes the radially-expanded state.

35. The method according to claim 34, wherein, when the stent-graft assumes the radially-expanded state, the fluid flow guide is shaped so as to define radially-diverging and radially-converging portions, which together define the bulge, wherein the radially-diverging portion is rostral to the radially-converging portion.

36. The method according to claim 35, wherein, when the stent-graft assumes the radially-expanded state, the substantially tubular structure overlaps the structural stent elements of the first subset overlap the structural stent elements of the second subset lengthwise along the entire radially-diverging portion.

37. The method according to claim 34, wherein, when the stent-graft assumes the radially-expanded state, the structural stent elements of the first subset are shaped so as to define a plurality of arms that extend radially outward, and are configured to cause the fluid flow guide to define the bulge.

* * * * *